US012797057B2

(12) United States Patent
Thommen et al.

(10) Patent No.: US 12,797,057 B2
(45) Date of Patent: *Nov. 17, 2026

(54) SURGICAL INSTRUMENT CONNECTORS AND RELATED METHODS

(71) Applicant: Medos International Sàrl, Le Locle (CH)

(72) Inventors: Daniel Thommen, Liestal (CH); Eric Buehlmann, Duxbury, MA (US); Joern Richter, Kandern (DE); Peter Senn, Waldenberg (CH); Veronique Christine Zollmann, Gebenstorf (CH); Thomas Gamache, Westport, MA (US); Roman Lomeli, Plymouth, MA (US); Nicholas Pavento, North Attleboro, MA (US); J. Riley Hawkins, Cumberland, RI (US); Jae Stelzer, Norton, MA (US)

(73) Assignee: Medos International Sarl, Le Locle (CH)

( * ) Notice: Subject to any disclaimer, the term of this patent is extended or adjusted under 35 U.S.C. 154(b) by 95 days.

This patent is subject to a terminal disclaimer.

(21) Appl. No.: 18/951,589

(22) Filed: Nov. 18, 2024

(65) Prior Publication Data

US 2025/0152158 A1 May 15, 2025

Related U.S. Application Data

(63) Continuation of application No. 17/884,523, filed on Aug. 9, 2022, now Pat. No. 12,150,636, which is a (Continued)

(51) Int. Cl.

*A61B 17/02* (2006.01)
*A61B 17/34* (2006.01)
(Continued)

(52) U.S. Cl.

CPC ...... *A61B 17/0218* (2013.01); *A61B 17/3421* (2013.01); *A61B 17/7049* (2013.01); (Continued)

(58) Field of Classification Search

CPC ..... A61B 17/02; A61B 17/0218; A61B 17/34; A61B 17/3421; A61B 17/70; (Continued)

(56) References Cited

U.S. PATENT DOCUMENTS 4,132,227 A 1/1979 Ibe
4,318,401 A 3/1982 Zimmerman
(Continued)

FOREIGN PATENT DOCUMENTS

CN 2659368 Y 12/2004
CN 1735380 A 2/2006
(Continued)

OTHER PUBLICATIONS

Japanese Notice of Reasons for Refusal for Application No. JP 2024-001761 dated Feb. 10, 2025 (8 pages).
(Continued)

*Primary Examiner* — Christopher J Beccia
(74) *Attorney, Agent, or Firm* — Flaster Greenberg PC

(57) ABSTRACT

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. The connector can have an unlocked state, in which the position and orientation of the access device can be adjusted relative to the support, and a locked state in which movement of the access device relative to the support is prevented or limited. Locking the
(Continued)

connector can also be effective to clamp or otherwise attach the connector to the access device and the support, or said attachment can be independent of the locking of the connector.

20 Claims, 33 Drawing Sheets

Related U.S. Application Data continuation of application No. 16/362,497, filed on Mar. 22, 2019, now Pat. No. 11,439,380, which is a continuation-in-part of application No. 15/786,923, filed on Oct. 18, 2017, now Pat. No. 10,869,659, which is a continuation-in-part of application No. 15/437,792, filed on Feb. 21, 2017, now Pat. No. 10,874,425, which is a continuation-in-part of application No. 15/254,877, filed on Sep. 1, 2016, now Pat. No. 10,987,129.

(60) Provisional application No. 62/468,475, filed on Mar. 8, 2017, provisional application No. 62/214,297, filed on Sep. 4, 2015.

(51) Int. Cl.

| | |
|---|---|
| ***A61B 17/70*** | (2006.01) |
| ***A61B 17/88*** | (2006.01) |
| ***A61B 90/50*** | (2016.01) |
| ***A61B 90/57*** | (2016.01) |
| ***A61C 8/00*** | (2006.01) |
| *A61B 17/00* | (2006.01) |
| *A61B 90/00* | (2016.01) |
| *A61B 90/30* | (2016.01) |

(52) U.S. Cl.

CPC ........ *A61B 17/7074* (2013.01); *A61B 17/708* (2013.01); *A61B 17/88* (2013.01); *A61B 90/50* (2016.02); *A61B 90/57* (2016.02); *A61C 8/0096* (2013.01); *A61B 2017/00314* (2013.01); *A61B 2017/00389* (2013.01); *A61B 2017/00407* (2013.01); *A61B 2017/00477* (2013.01); *A61B 2017/00858* (2013.01); *A61B 2017/00946* (2013.01); *A61B 2017/00951* (2013.01); *A61B 2017/0256* (2013.01); *A61B 17/8861* (2013.01); *A61B 90/30* (2016.02); *A61B 2090/3983* (2016.02); *A61B 2090/508* (2016.02)

(58) Field of Classification Search

CPC ............ A61B 17/7049; A61B 17/7074; A61B 17/708; A61C 8/0096

See application file for complete search history.

(56) References Cited

U.S. PATENT DOCUMENTS

| | | | |
|---|---|---|---|
| 4,573,448 A | | 3/1986 | Kambin |
| 4,646,738 A | | 3/1987 | Trott |
| 4,678,459 A | | 7/1987 | Onik et al. |
| 4,807,593 A | | 2/1989 | Ito |
| 4,863,430 A | | 9/1989 | Klyce et al. |
| 4,874,375 A | | 10/1989 | Ellison |
| 4,888,146 A | | 12/1989 | Dandeneau |
| 5,080,662 A | | 1/1992 | Paul |
| 5,195,541 A | | 3/1993 | Obenchain |
| 5,207,213 A | | 5/1993 | Auhll et al. |
| 5,285,795 A | | 2/1994 | Ryan et al. |
| 5,395,317 A | | 3/1995 | Kambin |
| 5,439,464 A | | 8/1995 | Shapiro |
| 5,529,580 A | | 6/1996 | Kusunoki et al. |
| 5,540,706 A | | 7/1996 | Aust et al. |
| 5,569,290 A | | 10/1996 | McAfee |
| 5,591,187 A | | 1/1997 | Dekel |
| 5,601,569 A | | 2/1997 | Pisharodi |
| 5,615,690 A | | 4/1997 | Giurtino et al. |
| 5,618,293 A | | 4/1997 | Sample et al. |
| 5,662,300 A | | 9/1997 | Michelson |
| 5,688,222 A | | 11/1997 | Hluchy et al. |
| 5,697,888 A | | 12/1997 | Kobayashi et al. |
| 5,716,355 A | | 2/1998 | Jackson et al. |
| 5,730,754 A | | 3/1998 | Obenchain |
| 5,733,242 A | | 3/1998 | Rayburn et al. |
| 5,735,792 A | | 4/1998 | Vanden Hoek et al. |
| 5,749,602 A | * | 5/1998 | Delaney ................. B01D 46/42 285/64 |
| 5,792,044 A | | 8/1998 | Foley et al. |
| 5,820,623 A | | 10/1998 | Ng |
| 5,885,300 A | | 3/1999 | Tokuhashi et al. |
| 5,894,369 A | | 4/1999 | Akiba et al. |
| 5,899,425 A | | 5/1999 | Corey, Jr. et al. |
| 5,928,137 A | | 7/1999 | Green |
| 5,954,635 A | | 9/1999 | Foley et al. |
| 5,976,075 A | | 11/1999 | Beane et al. |
| 5,989,183 A | | 11/1999 | Reisdorf et al. |
| 6,017,333 A | | 1/2000 | Bailey |
| 6,033,105 A | | 3/2000 | Barker et al. |
| 6,053,907 A | | 4/2000 | Zirps |
| 6,063,021 A | | 5/2000 | Hossain et al. |
| 6,110,182 A | | 8/2000 | Mowlai-Ashtiani |
| 6,126,592 A | | 10/2000 | Proch et al. |
| 6,139,563 A | | 10/2000 | Cosgrove, III et al. |
| 6,200,322 B1 | | 3/2001 | Branch et al. |
| 6,217,509 B1 | | 4/2001 | Foley et al. |
| 6,234,961 B1 | | 5/2001 | Gray |
| 6,283,966 B1 | | 9/2001 | Houfburg |
| 6,286,179 B1 | | 9/2001 | Byrne |
| 6,296,644 B1 | | 10/2001 | Saurat et al. |
| 6,322,498 B1 | | 11/2001 | Gravenstein et al. |
| 6,354,992 B1 | | 3/2002 | Kato |
| 6,357,710 B1 | | 3/2002 | Fielden et al. |
| 6,371,968 B1 | | 4/2002 | Kogasaka et al. |
| 6,383,191 B1 | | 5/2002 | Zdeblick et al. |
| 6,432,109 B1 | | 8/2002 | Letendart et al. |
| 6,447,446 B1 | | 9/2002 | Smith et al. |
| 6,468,289 B1 | | 10/2002 | Bonutti |
| 6,520,495 B1 | | 2/2003 | La Mendola |
| 6,558,407 B1 | | 5/2003 | Ivanko et al. |
| 6,575,899 B1 | | 6/2003 | Foley et al. |
| 6,579,281 B2 | | 6/2003 | Palmer et al. |
| 6,596,008 B1 | | 7/2003 | Kambin |
| 6,626,830 B1 | | 9/2003 | Califiore et al. |
| 6,648,915 B2 | | 11/2003 | Sazy |
| 6,663,563 B1 | | 12/2003 | Sharratt |
| 6,676,597 B2 | | 1/2004 | Guenst et al. |
| 6,679,833 B2 | | 1/2004 | Smith et al. |
| 6,685,724 B1 | | 2/2004 | Haluck |
| 6,688,564 B2 | | 2/2004 | Salvermoser et al. |
| 6,758,809 B2 | | 7/2004 | Briscoe et al. |
| 6,808,505 B2 | | 10/2004 | Kadan |
| 6,887,198 B2 | | 5/2005 | Phillips et al. |
| 6,983,930 B1 | * | 1/2006 | La Mendola ........... B25B 5/006 248/104 |
| 7,001,342 B2 | | 2/2006 | Faciszewski |
| 7,087,058 B2 | | 8/2006 | Cragg |
| 7,104,986 B2 | | 9/2006 | Hovda et al. |
| 7,137,949 B2 | | 11/2006 | Scirica et al. |
| 7,179,261 B2 | | 2/2007 | Sicvol et al. |
| 7,182,731 B2 | | 2/2007 | Nguyen et al. |
| 7,226,413 B2 | | 6/2007 | McKinley |
| 7,341,556 B2 | | 3/2008 | Shalman |
| 7,434,325 B2 | | 10/2008 | Foley et al. |
| 7,491,168 B2 | | 2/2009 | Raymond et al. |
| 7,591,790 B2 | | 9/2009 | Pflueger |
| 7,594,888 B2 | | 9/2009 | Raymond et al. |
| 7,618,431 B2 | | 11/2009 | Roehm, III et al. |
| 7,636,596 B2 | | 12/2009 | Solar |
| 7,637,905 B2 | | 12/2009 | Saadat et al. |
| 7,641,659 B2 | | 1/2010 | Emstad et al. |

(56) References Cited

U.S. PATENT DOCUMENTS

| | | | |
|---|---|---|---|
| 7,715,925 B2 | 5/2010 | Hafer et al. | |
| 7,766,313 B2 | 8/2010 | Panosian | |
| 7,771,384 B2 | 8/2010 | Ravo | |
| 7,794,456 B2 | 9/2010 | Sharps et al. | |
| 7,794,469 B2 | 9/2010 | Kao et al. | |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,079,952 B2 | 12/2011 | Fujimoto | |
| 8,092,464 B2 | 1/2012 | McKay | |
| 8,096,944 B2 | 1/2012 | Harrel | |
| 8,202,216 B2 | 6/2012 | Melkent et al. | |
| 8,206,357 B2 | 6/2012 | Bettuchi | |
| 8,230,863 B2 * | 7/2012 | Ravikumar | A61B 90/50 403/56 |
| 8,236,006 B2 | 8/2012 | Hamada | |
| 8,267,896 B2 | 9/2012 | Hartoumbekis et al. | |
| 8,303,492 B2 | 11/2012 | Ito | |
| 8,333,690 B2 | 12/2012 | Ikeda | |
| 8,337,532 B1 | 12/2012 | McLean et al. | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,419,625 B2 | 4/2013 | Ito | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,648,932 B2 | 2/2014 | Talbert et al. | |
| 8,688,186 B1 | 4/2014 | Mao et al. | |
| 8,690,764 B2 | 4/2014 | Clark et al. | |
| 8,721,536 B2 | 5/2014 | Marino et al. | |
| 8,727,975 B1 | 5/2014 | Pfabe et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,888,689 B2 | 11/2014 | Poll et al. | |
| 8,888,813 B2 | 11/2014 | To | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,545 B2 | 1/2015 | To | |
| 8,936,605 B2 | 1/2015 | Greenberg | |
| 8,952,312 B2 | 2/2015 | Blanquart et al. | |
| 8,961,404 B2 | 2/2015 | Ito | |
| 8,972,714 B2 | 3/2015 | Talbert et al. | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,036 B2 | 6/2015 | Poll et al. | |
| 9,050,037 B2 | 6/2015 | Poll et al. | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,123,602 B2 | 9/2015 | Blanquart | |
| 9,131,948 B2 | 9/2015 | Fang et al. | |
| 9,144,374 B2 | 9/2015 | Maurice, Jr. | |
| 9,153,609 B2 | 10/2015 | Blanquart | |
| 9,179,947 B2 * | 11/2015 | Bass | A61B 17/64 |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,226,647 B2 | 1/2016 | Sugawara | |
| 9,232,935 B2 | 1/2016 | Brand et al. | |
| 9,247,997 B2 | 2/2016 | Stefanchik et al. | |
| 9,265,491 B2 | 2/2016 | Lins et al. | |
| 9,277,928 B2 | 3/2016 | Morgenstern Lopez | |
| 9,289,249 B2 | 3/2016 | Ramsay et al. | |
| 9,307,972 B2 | 4/2016 | Lovell et al. | |
| 9,320,419 B2 | 4/2016 | Kirma et al. | |
| RE46,007 E | 5/2016 | Banik | |
| RE46,062 E | 7/2016 | James | |
| 9,386,971 B1 | 7/2016 | Casey et al. | |
| 9,387,313 B2 | 7/2016 | Culbert et al. | |
| 9,414,828 B2 | 8/2016 | Abidin et al. | |
| 9,462,234 B2 | 10/2016 | Blanquart et al. | |
| 9,486,296 B2 | 11/2016 | Mire et al. | |
| 9,492,194 B2 | 11/2016 | Morgenstern Lopez et al. | |
| 9,509,917 B2 | 11/2016 | Blanquart et al. | |
| 9,510,853 B2 | 12/2016 | Aljuri et al. | |
| 9,516,239 B2 | 12/2016 | Blanquart et al. | |
| 9,522,017 B2 | 12/2016 | Poll et al. | |
| 9,526,401 B2 | 12/2016 | Saadat et al. | |
| 9,579,012 B2 | 2/2017 | Vazales et al. | |
| 9,603,510 B2 | 3/2017 | Ammirati | |
| 9,603,610 B2 | 3/2017 | Richter et al. | |
| 9,610,007 B2 | 4/2017 | Kienzle et al. | |
| 9,610,095 B2 | 4/2017 | To | |
| 9,622,650 B2 | 4/2017 | Blanquart | |
| 9,629,521 B2 | 4/2017 | Ratnakar | |
| 9,641,815 B2 | 5/2017 | Richardson et al. | |
| 9,655,605 B2 | 5/2017 | Serowski et al. | |
| 9,655,639 B2 | 5/2017 | Mark | |
| 9,668,643 B2 | 6/2017 | Kennedy, II et al. | |
| 9,675,235 B2 | 6/2017 | Lieponis | |
| 9,700,378 B2 | 7/2017 | Mowlai-Ashtiani | |
| 9,706,905 B2 | 7/2017 | Levy | |
| 10,111,712 B2 | 10/2018 | Chegini et al. | |
| 10,500,699 B2 * | 12/2019 | Chang | B25B 5/003 |
| 10,561,427 B2 | 2/2020 | Weitzman et al. | |
| 10,576,231 B2 | 3/2020 | Gunday et al. | |
| 10,682,130 B2 | 6/2020 | White et al. | |
| 10,758,220 B2 | 9/2020 | White et al. | |
| 10,869,659 B2 | 12/2020 | Thommen et al. | |
| 10,874,425 B2 | 12/2020 | Thommen et al. | |
| 10,987,129 B2 | 4/2021 | Thommen et al. | |
| 11,000,312 B2 | 5/2021 | Thommen et al. | |
| 11,331,090 B2 | 5/2022 | Thommen et al. | |
| 11,344,190 B2 | 5/2022 | Thommen et al. | |
| 11,439,380 B2 | 9/2022 | Thommen et al. | |
| 11,559,328 B2 | 1/2023 | Richter et al. | |
| 11,672,562 B2 | 6/2023 | Thommen et al. | |
| 11,712,264 B2 | 8/2023 | Thommen et al. | |
| 11,744,447 B2 | 9/2023 | Thommen et al. | |
| 11,793,546 B2 | 10/2023 | Thommen et al. | |
| 11,801,070 B2 | 10/2023 | White et al. | |
| 11,806,043 B2 | 11/2023 | White et al. | |
| 11,883,064 B2 | 1/2024 | Thommen et al. | |
| 11,950,766 B2 | 4/2024 | Thommen et al. | |
| 12,150,636 B2 * | 11/2024 | Thommen | A61B 1/00135 |
| 12,193,704 B2 | 1/2025 | Richter et al. | |
| 12,383,302 B2 | 8/2025 | Thommen et al. | |
| 12,402,909 B2 | 9/2025 | Thommen et al. | |
| 12,496,093 B2 | 12/2025 | Thommen et al. | |
| 12,507,880 B2 | 12/2025 | White et al. | |
| 2002/0022762 A1 | 2/2002 | Beane et al. | |
| 2002/0035313 A1 | 3/2002 | Scirica et al. | |
| 2002/0091390 A1 | 7/2002 | Michelson | |

(56) References Cited

U.S. PATENT DOCUMENTS

| | | | |
|---|---|---|---|
| 2002/0138020 | A1 | 9/2002 | Pflueger |
| 2002/0165560 | A1 | 11/2002 | Danitz et al. |
| 2003/0083555 | A1 | 5/2003 | Hunt et al. |
| 2003/0083688 | A1 | 5/2003 | Simonson |
| 2003/0171744 | A1 | 9/2003 | Leung et al. |
| 2003/0191474 | A1 | 10/2003 | Cragg et al. |
| 2004/0092940 | A1 | 5/2004 | Zwirnmann |
| 2004/0122446 | A1 | 6/2004 | Solar |
| 2004/0127992 | A1 | 7/2004 | Serhan et al. |
| 2004/0143165 | A1 | 7/2004 | Alleyne |
| 2004/0158260 | A1 | 8/2004 | Blau et al. |
| 2004/0158286 | A1 | 8/2004 | Roux et al. |
| 2004/0176763 | A1 | 9/2004 | Foley et al. |
| 2004/0249246 | A1 | 12/2004 | Campos |
| 2005/0021040 | A1 | 1/2005 | Bertagnoli |
| 2005/0075540 | A1 | 4/2005 | Shluzas et al. |
| 2005/0075644 | A1 | 4/2005 | DiPoto et al. |
| 2005/0080435 | A1 | 4/2005 | Smith et al. |
| 2005/0085692 | A1 | 4/2005 | Kiehn et al. |
| 2005/0090848 | A1 | 4/2005 | Adams |
| 2005/0107671 | A1 | 5/2005 | McKinley |
| 2005/0137461 | A1 | 6/2005 | Marchek et al. |
| 2005/0165420 | A1 | 7/2005 | Cha |
| 2005/0187570 | A1 | 8/2005 | Nguyen et al. |
| 2005/0192589 | A1 | 9/2005 | Raymond et al. |
| 2005/0256525 | A1 | 11/2005 | Culbert et al. |
| 2006/0020165 | A1 | 1/2006 | Adams |
| 2006/0041270 | A1 | 2/2006 | Lenker et al. |
| 2006/0052671 | A1 | 3/2006 | McCarthy |
| 2006/0074445 | A1 | 4/2006 | Gerber et al. |
| 2006/0142643 | A1 | 6/2006 | Parker |
| 2006/0161189 | A1 | 7/2006 | Harp |
| 2006/0173521 | A1 | 8/2006 | Pond, Jr. et al. |
| 2006/0200186 | A1 | 9/2006 | Marchek et al. |
| 2006/0206118 | A1 | 9/2006 | Kim et al. |
| 2006/0241350 | A1 | 10/2006 | Nowitzke et al. |
| 2006/0264895 | A1 | 11/2006 | Flanders |
| 2007/0016223 | A1 | 1/2007 | Pagliuca et al. |
| 2007/0049794 | A1 | 3/2007 | Glassenberg et al. |
| 2007/0055259 | A1 | 3/2007 | Norton et al. |
| 2007/0129634 | A1 | 6/2007 | Hickey et al. |
| 2007/0149975 | A1 | 6/2007 | Oliver et al. |
| 2007/0162223 | A1 | 7/2007 | Clark |
| 2007/0173879 | A1 | 7/2007 | Pandey |
| 2007/0203396 | A1 | 8/2007 | McCutcheon et al. |
| 2007/0213716 | A1 | 9/2007 | Lenke et al. |
| 2007/0225556 | A1 | 9/2007 | Ortiz et al. |
| 2007/0249899 | A1 | 10/2007 | Seifert |
| 2007/0255100 | A1 | 11/2007 | Barlow et al. |
| 2007/0260113 | A1 | 11/2007 | Otawara |
| 2007/0260120 | A1 | 11/2007 | Otawara |
| 2007/0260184 | A1 | 11/2007 | Justis et al. |
| 2007/0270866 | A1 | 11/2007 | von Jako |
| 2008/0015621 | A1 | 1/2008 | Emanuel |
| 2008/0033251 | A1 | 2/2008 | Araghi |
| 2008/0064921 | A1 | 3/2008 | Larkin et al. |
| 2008/0064928 | A1 | 3/2008 | Otawara |
| 2008/0081951 | A1 | 4/2008 | Frasier et al. |
| 2008/0139879 | A1 | 6/2008 | Olson et al. |
| 2008/0147109 | A1 | 6/2008 | Kambin et al. |
| 2008/0183189 | A1 | 7/2008 | Teichman et al. |
| 2008/0188714 | A1 | 8/2008 | McCaffrey |
| 2008/0242930 | A1 | 10/2008 | Hanypsiak et al. |
| 2008/0260342 | A1 | 10/2008 | Kuroiwa |
| 2009/0012578 | A1 | 1/2009 | Carrez et al. |
| 2009/0018566 | A1 | 1/2009 | Escudero et al. |
| 2009/0024158 | A1 | 1/2009 | Viker |
| 2009/0062604 | A1 | 3/2009 | Minosawa et al. |
| 2009/0062871 | A1 | 3/2009 | Chin et al. |
| 2009/0076549 | A1 | 3/2009 | Lim et al. |
| 2009/0105543 | A1 | 4/2009 | Miller et al. |
| 2009/0125032 | A1 | 5/2009 | Gutierrez et al. |
| 2009/0149857 | A1 | 6/2009 | Culbert et al. |
| 2009/0156898 | A1 | 6/2009 | Ichimura |
| 2009/0187080 | A1 | 7/2009 | Seex |
| 2009/0240111 | A1 | 9/2009 | Kessler et al. |
| 2009/0247831 | A1 | 10/2009 | Miyamoto et al. |
| 2009/0253964 | A1 | 10/2009 | Miyamoto |
| 2009/0253965 | A1 | 10/2009 | Miyamoto |
| 2009/0259184 | A1 | 10/2009 | Okoniewski |
| 2009/0264895 | A1 | 10/2009 | Gasperut et al. |
| 2009/0287061 | A1 | 11/2009 | Feigenbaum et al. |
| 2009/0318765 | A1 | 12/2009 | Torii |
| 2010/0004651 | A1 | 1/2010 | Biyani |
| 2010/0022841 | A1 | 1/2010 | Takahashi et al. |
| 2010/0036384 | A1 | 2/2010 | Gorek et al. |
| 2010/0076476 | A1 | 3/2010 | To et al. |
| 2010/0081875 | A1 | 4/2010 | Fowler et al. |
| 2010/0114147 | A1 | 5/2010 | Biyani |
| 2010/0151161 | A1 | 6/2010 | Da Rolo |
| 2010/0161060 | A1 | 6/2010 | Schaller et al. |
| 2010/0204703 | A1 | 8/2010 | Gao |
| 2010/0240961 | A1 | 9/2010 | Aferzon |
| 2010/0256446 | A1 | 10/2010 | Raju |
| 2010/0268241 | A1 | 10/2010 | Flom et al. |
| 2010/0280325 | A1 | 11/2010 | Ibrahim et al. |
| 2010/0284580 | A1 | 11/2010 | OuYang et al. |
| 2010/0286477 | A1 | 11/2010 | OuYang et al. |
| 2010/0312053 | A1 | 12/2010 | Larsen |
| 2010/0312103 | A1 | 12/2010 | Gorek et al. |
| 2010/0317928 | A1 | 12/2010 | Subramaniam |
| 2010/0324506 | A1 | 12/2010 | Pellegrino et al. |
| 2011/0009905 | A1 | 1/2011 | Shluzas |
| 2011/0028791 | A1 | 2/2011 | Marino et al. |
| 2011/0040333 | A1 | 2/2011 | Simonson et al. |
| 2011/0054507 | A1 | 3/2011 | Batten et al. |
| 2011/0056500 | A1 | 3/2011 | Shin et al. |
| 2011/0073594 | A1 | 3/2011 | Bonn |
| 2011/0098628 | A1 | 4/2011 | Yeung et al. |
| 2011/0106261 | A1 | 5/2011 | Chin et al. |
| 2011/0112588 | A1 | 5/2011 | Linderman et al. |
| 2011/0125158 | A1 | 5/2011 | Diwan et al. |
| 2011/0130634 | A1 | 6/2011 | Solitario, Jr. et al. |
| 2011/0201888 | A1 | 8/2011 | Verner |
| 2011/0230965 | A1 | 9/2011 | Schell et al. |
| 2011/0251597 | A1 | 10/2011 | Bharadwaj et al. |
| 2011/0257478 | A1 | 10/2011 | Kleiner et al. |
| 2011/0295070 | A1 | 12/2011 | Yasunaga |
| 2011/0319941 | A1 | 12/2011 | Bar et al. |
| 2012/0016192 | A1 | 1/2012 | Jansen et al. |
| 2012/0029412 | A1 | 2/2012 | Yeung et al. |
| 2012/0095296 | A1 | 4/2012 | Trieu et al. |
| 2012/0101338 | A1 | 4/2012 | O'Prey et al. |
| 2012/0111682 | A1 | 5/2012 | Andre |
| 2012/0116170 | A1 | 5/2012 | Vayser et al. |
| 2012/0157788 | A1 | 6/2012 | Serowski et al. |
| 2012/0172664 | A1 | 7/2012 | Hayman et al. |
| 2012/0197320 | A1 | 8/2012 | Bereczki |
| 2012/0209273 | A1 | 8/2012 | Zaretzka et al. |
| 2012/0221007 | A1 | 8/2012 | Batten et al. |
| 2012/0232350 | A1 | 9/2012 | Seex |
| 2012/0232552 | A1 | 9/2012 | Morgenstern Lopez et al. |
| 2012/0259173 | A1 | 10/2012 | Waldron et al. |
| 2012/0265022 | A1 | 10/2012 | Menn |
| 2012/0296171 | A1 | 11/2012 | Lovell et al. |
| 2012/0298820 | A1 | 11/2012 | Manolidis |
| 2012/0303039 | A1 | 11/2012 | Chin et al. |
| 2012/0316400 | A1 | 12/2012 | Vijayanagar |
| 2012/0323080 | A1 | 12/2012 | DeRidder et al. |
| 2013/0030535 | A1 | 1/2013 | Foley et al. |
| 2013/0103067 | A1 | 4/2013 | Fabro et al. |
| 2013/0103103 | A1 | 4/2013 | Mire et al. |
| 2013/0150670 | A1 | 6/2013 | O'Prey et al. |
| 2013/0150674 | A1 | 6/2013 | Haig et al. |
| 2013/0172674 | A1 | 7/2013 | Kennedy, II et al. |
| 2013/0172676 | A1 | 7/2013 | Levy et al. |
| 2013/0211202 | A1 | 8/2013 | Perez-Cruet et al. |
| 2013/0282022 | A1 | 10/2013 | Yousef |
| 2013/0289354 | A1 | 10/2013 | Ainsworth et al. |
| 2013/0289399 | A1 | 10/2013 | Choi et al. |
| 2013/0303846 | A1 | 11/2013 | Cybulski et al. |
| 2013/0304106 | A1 | 11/2013 | Breznock |
| 2013/0331730 | A1 | 12/2013 | Fenech et al. |
| 2014/0025121 | A1 | 1/2014 | Foley et al. |

(56) References Cited

U.S. PATENT DOCUMENTS

| | | | |
|---|---|---|---|
| 2014/0066940 | A1 | 3/2014 | Fang et al. |
| 2014/0074170 | A1 | 3/2014 | Mertens et al. |
| 2014/0088367 | A1 | 3/2014 | DiMauro et al. |
| 2014/0128979 | A1 | 5/2014 | Womble et al. |
| 2014/0142584 | A1 | 5/2014 | Sweeney |
| 2014/0148647 | A1 | 5/2014 | Okazaki |
| 2014/0163319 | A1 | 6/2014 | Blanquart et al. |
| 2014/0165796 | A1 | 6/2014 | Gauthier et al. |
| 2014/0180321 | A1 | 6/2014 | Dias et al. |
| 2014/0194697 | A1 | 7/2014 | Seex |
| 2014/0215736 | A1 | 8/2014 | Gomez et al. |
| 2014/0221749 | A1 | 8/2014 | Grant et al. |
| 2014/0222092 | A1 | 8/2014 | Anderson et al. |
| 2014/0243604 | A1 | 8/2014 | Vennard et al. |
| 2014/0257296 | A1 | 9/2014 | Morgenstern Lopez |
| 2014/0257332 | A1 | 9/2014 | Zastrozna |
| 2014/0257489 | A1 | 9/2014 | Warren et al. |
| 2014/0261545 | A1 | 9/2014 | Jenkins et al. |
| 2014/0275793 | A1 | 9/2014 | Song |
| 2014/0275799 | A1 | 9/2014 | Schuele |
| 2014/0276840 | A1 | 9/2014 | Richter et al. |
| 2014/0276916 | A1 | 9/2014 | Ahluwalia et al. |
| 2014/0277204 | A1 | 9/2014 | Sandhu |
| 2014/0285644 | A1 | 9/2014 | Richardson et al. |
| 2014/0318582 | A1 | 10/2014 | Mowlai-Ashtiani |
| 2014/0336764 | A1 | 11/2014 | Masson et al. |
| 2014/0357945 | A1 | 12/2014 | Duckworth |
| 2014/0371763 | A1 | 12/2014 | Poll et al. |
| 2014/0378985 | A1 | 12/2014 | Mafi |
| 2015/0018623 | A1 | 1/2015 | Friedrich et al. |
| 2015/0065795 | A1 | 3/2015 | Titus |
| 2015/0073218 | A1 | 3/2015 | Ito |
| 2015/0087913 | A1 | 3/2015 | Dang et al. |
| 2015/0094610 | A1 | 4/2015 | Morgenstern Lopez et al. |
| 2015/0112398 | A1 | 4/2015 | Morgenstern Lopez et al. |
| 2015/0133727 | A1 | 5/2015 | Bacich et al. |
| 2015/0164496 | A1 | 6/2015 | Karpowicz et al. |
| 2015/0216593 | A1 | 8/2015 | Biyani |
| 2015/0223671 | A1 | 8/2015 | Sung et al. |
| 2015/0223676 | A1 | 8/2015 | Bayer et al. |
| 2015/0230697 | A1 | 8/2015 | Phee et al. |
| 2015/0238073 | A1 | 8/2015 | Charles et al. |
| 2015/0250377 | A1 | 9/2015 | Iizuka |
| 2015/0257746 | A1 | 9/2015 | Seifert |
| 2015/0272694 | A1 | 10/2015 | Charles |
| 2015/0313585 | A1 | 11/2015 | Abidin et al. |
| 2015/0313633 | A1 | 11/2015 | Gross et al. |
| 2015/0327757 | A1 | 11/2015 | Rozenfeld et al. |
| 2015/0335389 | A1 | 11/2015 | Greenberg |
| 2015/0342619 | A1 | 12/2015 | Weitzman |
| 2015/0342621 | A1 | 12/2015 | Jackson, III |
| 2015/0366552 | A1 | 12/2015 | Sasaki et al. |
| 2015/0374213 | A1 | 12/2015 | Maurice, Jr. |
| 2015/0374354 | A1 | 12/2015 | Boyd et al. |
| 2016/0007982 | A1 | 1/2016 | Liu et al. |
| 2016/0015467 | A1 | 1/2016 | Vayser et al. |
| 2016/0030061 | A1 | 2/2016 | Thommen et al. |
| 2016/0066965 | A1 | 3/2016 | Chegini et al. |
| 2016/0067003 | A1 | 3/2016 | Chegini et al. |
| 2016/0074029 | A1 | 3/2016 | O'Connell et al. |
| 2016/0095505 | A1 | 4/2016 | Johnson et al. |
| 2016/0106408 | A1 | 4/2016 | Ponmudi et al. |
| 2016/0143682 | A1 | 5/2016 | Overes et al. |
| 2016/0166135 | A1 | 6/2016 | Fiset |
| 2016/0174814 | A1 | 6/2016 | Igov |
| 2016/0175004 | A1 | 6/2016 | Dejima |
| 2016/0192921 | A1 | 7/2016 | Pimenta et al. |
| 2016/0213500 | A1 | 7/2016 | Beger et al. |
| 2016/0228280 | A1 | 8/2016 | Schuele et al. |
| 2016/0235284 | A1 | 8/2016 | Yoshida et al. |
| 2016/0235427 | A1 | 8/2016 | Rudser |
| 2016/0256036 | A1 | 9/2016 | Gomez et al. |
| 2016/0287264 | A1 | 10/2016 | Chegini et al. |
| 2016/0296220 | A1 | 10/2016 | Mast et al. |
| 2016/0324541 | A1 | 11/2016 | Pellegrino et al. |
| 2016/0345952 | A1 | 12/2016 | Kucharzyk et al. |
| 2016/0353978 | A1 | 12/2016 | Miller et al. |
| 2016/0367294 | A1 | 12/2016 | Boyd et al. |
| 2017/0003493 | A1 | 1/2017 | Zhao |
| 2017/0007226 | A1 | 1/2017 | Fehling |
| 2017/0007294 | A1 | 1/2017 | Iwasaka et al. |
| 2017/0020627 | A1 | 1/2017 | Tesar et al. |
| 2017/0027606 | A1 | 2/2017 | Cappelleri et al. |
| 2017/0042408 | A1 | 2/2017 | Washburn et al. |
| 2017/0042411 | A1 | 2/2017 | Kang et al. |
| 2017/0065269 | A1 | 3/2017 | Thommen et al. |
| 2017/0065287 | A1 | 3/2017 | Silva et al. |
| 2017/0086878 | A1 | 3/2017 | Geist |
| 2017/0086939 | A1 | 3/2017 | Vayser et al. |
| 2017/0105770 | A1 | 4/2017 | Woolley et al. |
| 2017/0135699 | A1 | 5/2017 | Wolf |
| 2017/0156755 | A1 | 6/2017 | Poll et al. |
| 2017/0156814 | A1 | 6/2017 | Thommen et al. |
| 2017/0196549 | A1 | 7/2017 | Piskun et al. |
| 2017/0224391 | A1 | 8/2017 | Biester et al. |
| 2017/0245930 | A1 | 8/2017 | Brannan et al. |
| 2017/0280969 | A1 | 10/2017 | Levy et al. |
| 2017/0296038 | A1 | 10/2017 | Gordon et al. |
| 2017/0311789 | A1 | 11/2017 | Mulcahey et al. |
| 2018/0008138 | A1 | 1/2018 | Thommen et al. |
| 2018/0008253 | A1 | 1/2018 | Thommen et al. |
| 2018/0014858 | A1 | 1/2018 | Biester et al. |
| 2018/0014890 | A1 | 1/2018 | Stanton et al. |
| 2018/0098788 | A1 | 4/2018 | White et al. |
| 2018/0098789 | A1 | 4/2018 | White et al. |
| 2018/0110503 | A1 | 4/2018 | Flock et al. |
| 2018/0110506 | A1 | 4/2018 | Thommen et al. |
| 2018/0153592 | A1 | 6/2018 | Larson |
| 2018/0214016 | A1 | 8/2018 | Thommen et al. |
| 2018/0249992 | A1 | 9/2018 | Truckey |
| 2018/0311051 | A1 | 11/2018 | Donaldson et al. |
| 2018/0333061 | A1 | 11/2018 | Pracyk et al. |
| 2019/0105459 | A1 | 4/2019 | Lajarín Barquero |
| 2019/0209154 | A1 | 7/2019 | Richter et al. |
| 2019/0216454 | A1 | 7/2019 | Thommen et al. |
| 2019/0216486 | A1 | 7/2019 | Weitzman |
| 2019/0374236 | A1 | 12/2019 | Weitzman et al. |
| 2020/0268368 | A1 | 8/2020 | White et al. |
| 2020/0360048 | A1 | 11/2020 | White et al. |
| 2020/0367737 | A1 | 11/2020 | Matsumoto et al. |
| 2021/0052298 | A1 | 2/2021 | Thommen et al. |
| 2021/0186316 | A1 | 6/2021 | Thommen et al. |
| 2021/0204973 | A1 | 7/2021 | Thommen et al. |
| 2021/0282806 | A1 | 9/2021 | Thommen et al. |
| 2022/0192700 | A1 | 6/2022 | Thommen et al. |
| 2022/0249125 | A1 | 8/2022 | Thommen et al. |
| 2022/0265134 | A1 | 8/2022 | Thommen et al. |
| 2022/0378408 | A1 | 12/2022 | Thommen et al. |
| 2023/0135764 | A1 | 5/2023 | Richter et al. |
| 2024/0023987 | A1 | 1/2024 | Thommen et al. |
| 2024/0023989 | A1 | 1/2024 | White et al. |
| 2024/0206909 | A1 | 6/2024 | Thommen et al. |
| 2025/0195105 | A1 | 6/2025 | Richter et al. |

FOREIGN PATENT DOCUMENTS

| | | | |
|---|---|---|---|
| CN | 1742685 | A | 3/2006 |
| CN | 101141928 | A | 3/2008 |
| CN | 101426437 | A | 5/2009 |
| CN | 201290744 | Y | 8/2009 |
| CN | 101594830 | A | 12/2009 |
| CN | 101815476 | A | 8/2010 |
| CN | 102448380 | A | 5/2012 |
| CN | 202211669 | U | 5/2012 |
| CN | 102843984 | A | 12/2012 |
| CN | 202740102 | U | 2/2013 |
| CN | 102727309 | B | 11/2014 |
| CN | 102497828 | B | 9/2015 |
| CN | 102821673 | B | 6/2016 |
| CN | 103976779 | B | 9/2016 |
| CN | 106659375 | A | 5/2017 |
| CN | 106794032 | A | 5/2017 |
| CN | 103533904 | B | 6/2017 |
| CN | 105286776 | B | 11/2017 |

(56) References Cited

FOREIGN PATENT DOCUMENTS

| | | | |
|---|---|---|---|
| CN | 107126254 | B | 1/2020 |
| CN | 111278365 | A | 6/2020 |
| DE | 9415039 | U1 | 11/1994 |
| DE | 29916026 | U1 | 11/1999 |
| DE | 20309079 | U1 | 8/2003 |
| EP | 0537116 | A1 | 4/1993 |
| EP | 0890341 | A1 | 1/1999 |
| EP | 0807415 | B1 | 12/2003 |
| EP | 0891156 | B1 | 7/2004 |
| EP | 2491848 | B1 | 1/2014 |
| GB | 2481727 | B | 5/2012 |
| JP | H05207962 | A | 8/1993 |
| JP | H0681501 | A | 3/1994 |
| JP | H08126605 | A | 5/1996 |
| JP | H08278456 | A | 10/1996 |
| JP | H11313795 | A | 11/1999 |
| JP | 2000126190 | A | 5/2000 |
| JP | 2000511788 | A | 9/2000 |
| JP | 2001520906 | A | 11/2001 |
| JP | 2002519094 | A | 7/2002 |
| JP | 2002541901 | A | 12/2002 |
| JP | 2007007438 | A | 1/2007 |
| JP | 2007508050 | A | 4/2007 |
| JP | 2008508943 | A | 3/2008 |
| JP | 2009543612 | A | 12/2009 |
| JP | 2011512943 | A | 4/2011 |
| JP | 2012045325 | A | 3/2012 |
| JP | 2012527327 | A | 11/2012 |
| JP | 2012527930 | A | 11/2012 |
| JP | 2013059688 | A | 4/2013 |
| JP | 2013538624 | A | 10/2013 |
| JP | 2014054561 | A | 3/2014 |
| JP | 2014517710 | A | 7/2014 |
| JP | 2015500680 | A | 1/2015 |
| JP | 2015521913 | A | 8/2015 |
| JP | 2019505312 | A | 2/2019 |
| JP | 2022079758 | A | 5/2022 |
| WO | 1996029014 | A1 | 9/1996 |
| WO | 1997034536 | A2 | 9/1997 |
| WO | 2001056490 | A1 | 8/2001 |
| WO | 2001089371 | A1 | 11/2001 |
| WO | 2002002016 | A1 | 1/2002 |
| WO | 2004039235 | A2 | 5/2004 |
| WO | 2004103430 | A2 | 12/2004 |
| WO | 2006017507 | A2 | 2/2006 |
| WO | 2006096517 | A2 | 9/2006 |
| WO | 2007059068 | A1 | 5/2007 |
| WO | 2008121162 | A1 | 10/2008 |
| WO | 2009033207 | A1 | 3/2009 |
| WO | 2009108318 | A2 | 9/2009 |
| WO | 2010111629 | A2 | 9/2010 |
| WO | 2010135537 | A2 | 11/2010 |
| WO | 2010138083 | A1 | 12/2010 |
| WO | 2012004766 | A2 | 1/2012 |
| WO | 2012040239 | A1 | 3/2012 |
| WO | 2012122294 | A1 | 9/2012 |
| WO | 2013033426 | A2 | 3/2013 |
| WO | 2013059640 | A1 | 4/2013 |
| WO | 2013074396 | A1 | 5/2013 |
| WO | 2014041540 | A1 | 3/2014 |
| WO | 2014050236 | A1 | 4/2014 |
| WO | 2014100761 | A2 | 6/2014 |
| WO | 2014185334 | A1 | 11/2014 |
| WO | 2014188796 | A1 | 11/2014 |
| WO | 2015026793 | A1 | 2/2015 |
| WO | 2015033907 | A1 | 3/2015 |
| WO | 2015175635 | A1 | 11/2015 |
| WO | 2016111373 | A1 | 7/2016 |
| WO | 2016131077 | A1 | 8/2016 |
| WO | 2016168673 | A1 | 10/2016 |
| WO | 2016201292 | A1 | 12/2016 |
| WO | 2017006684 | A1 | 1/2017 |
| WO | 2017015480 | A1 | 1/2017 |
| WO | 2017040873 | A1 | 3/2017 |
| WO | 2017083648 | A1 | 5/2017 |
| WO | 2017162895 | A1 | 9/2017 |
| WO | 2018131039 | A1 | 7/2018 |
| WO | 2018147225 | A1 | 8/2018 |
| WO | 2018165365 | A2 | 9/2018 |
| WO | 2019026206 | A1 | 2/2019 |
| WO | 2019050666 | A1 | 3/2019 |
| WO | 2021209987 | A1 | 10/2021 |

OTHER PUBLICATIONS

Australian Examination Report for Application No. 2018225113, issued Jul. 15, 2022 (4 pages).

Chinese Office Action for Application No. 201880013056.7, dated Mar. 25, 2021 (15 pages).

Chinese Office Action for Application No. 201880013056.7, dated Oct. 26, 2021 (6 pages).

Chinese Office Action for Application No. 201880016688.9, dated Mar. 8, 2022, with Translation (21 pages).

Chinese Decision of Reexamination issued for 201680051245.4, dated Aug. 23, 2022, (23 pages).

Chinese Office Action and Search Report issued for Application No. 201880058099, dated Nov. 2, 2022 (14 pages).

Chinese First Search and Written Opinion for Application No. CN201980027429.0 dated Jan. 2, 2024 (10 pages).

Chinese First Search and Written Opinion for Application No. CN202080035605 dated Jan. 8, 2024 (10 pages).

Chinese Office Action issued for Application No. 202110037202.3 dated Nov. 24, 2023 (14 pages).

Chinese Second Office Action for Application No. CN 202080035605.8 dated May 23, 2024 (9 pages).

Clinical Workbook of Neurosurgery in Xijing [M], edited by Fei Zhou, Xi'an: Fourth Military Medical University Press, Aug. 2012, pp. 431-432: an endoscope with a diameter of 3.7 mm is used for intramedullary examination).

Extended European Search Report for Application No. 16843037.9; issued Mar. 14, 2019 (8 pages).

Extended European Search Report for Application No. 18758290.3, issued Nov. 27, 2020 (7 pages).

Extended European Search Report for Application No. 20212396.4, issued Sep. 23, 2021 (9 pages).

Extended European Search Report for Application No. 18854503.2, issued Apr. 15, 2021 (10 pages).

Extended European Search Report for Application No. 19758283.6, issued Sep. 28, 2021 (8 pages).

Extended European Search Report for Application No. 18764249.1, issued Mar. 11, 2022 (8 pages).

Extended European Search Report for Application No. 18764504.9, issued Mar. 18, 2022 (7 pages).

Extended European Search Report for Application No. 18764370.5, issued Mar. 25, 2022 (8 pages).

Extended European Search Report for Application No. 24156567, issued Jun. 6, 2024 (8 pages).

Extended European Search Report for Application No. 24190167.7 sued Oct. 7, 2024 (11 pages).

Hott, J. S., et al., "A new table-fixed retractor for anterior odontoid screw fixation: technical note," J Neurosurg (Spine 3), 2003, v. 98, pp. 118-120.

International Search Report and Written Opinion for Application No. PCT/US2015/043554, mailed Nov. 19, 2015 (8 pages).

International Search Report and Written Opinion for Application No. PCT/US2015/048485, mailed Feb. 9, 2016. (16 pages).

International Search Report and Written Opinion for Application No. PCT/US2015/060978, mailed Feb. 15, 2016 (8 pages).

Invitation to Pay Additional Fees for Application No. PCT/US2016/050022, mailed Nov. 3, 2016 (2 pages).

International Search Report and Written Opinion for Application No. PCT/US2016/050022, issued Feb. 1, 2017 (19 pages).

International Preliminary Report on Patentability issued for Application No. PCT/US2016/050022, mailed Mar. 15, 2018.

International Search Report and Written Opinion for Application No. PCT/US2018/018905, mailed May 7, 2018 (10 pages).

International Search Report for Application No. PCT/IB2018/057367, mailed Jan. 29, 2019, (4 pages).

(56) References Cited

OTHER PUBLICATIONS

International Search Report and Written Opinion for Application No. PCT/US2018/021449, mailed Aug. 27, 2018 (13 pages).
International Search Report and Written Opinion for Application No. PCT/US2018/021454, mailed Jul. 3, 2018 (16 pages).
International Search Report and Written Opinion for Application No. PCT/US2018/021466 mailed Jul. 3, 2018 (8 pages).
International Search Report and Written Opinion for Application No. PCT/US2018/047136, mailed Jan. 23, 2019 (9 pages).
International Search Report and Written Opinion for Application No. PCT/EP2020/056706, mailed Jun. 9, 2020 (17 pages).
International Search Report and Written Opinion issued for Application No. PCT/US2018/021472, issued Jul. 19, 2018.
International Search Report and Written Opinion for Application No. PCT/US19/18700, mailed May 3, 2019 (7 pages).
Iprenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.
Japanese Office Action issued in Appln. No. JP 2018-511695, mailed May 26, 2020 (21 pages).
Japanese Office Action for Application No. JP 2019-548591, issued Oct. 5, 2021, (14 pages).
Japanese Office Action for Application No. JP 2019-545263, issued Jan. 4, 2022 (11 pages).
Japanese Office Action for Application No. JP 2019-545263, issued Aug. 9, 2022 (8 pages).
Japanese Office Action for Application No. JP 2020-513791, issued May 17, 2022 (8 pages).
Japanese Office Action for Application No. JP 2020-177880, issued May 31, 2022 (3 pages).
Japanese Decision to Grant a Patent for Application No. JP 2020-177880, issued Dec. 6, 2022 (2 pages).
Japanese Decision to Grant Patent for Application No. JP 2020-544278, issued Mar. 14, 2023.
Japanese Notice of Reasons for Refusal for Application No. JP 2021-554717, dated Nov. 9, 2023 (4 pages).
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al., "Retrospective analysis and modifications of retractor systems for anterior odontoid screw fixation," Neurosurg Focus 16 (1):Article 14, 2004, pp. 1-4.
U.S. Appl. No. 15/254,877, filed Sep. 1, 2016, Multi-Shield Spinal Access Systems, Medos International Sàrl.
U.S. Appl. No. 15/437,792, filed Feb. 21, 2017, Multi-Shield Spinal Access Systems, Medos International Sàrl.
U.S. Appl. No. 15/692,845, filed Aug. 31, 2017, Surgical Visualization Systems and Related Methods, Medos International Sàrl.
U.S. Appl. No. 15/697,494, filed Sep. 7, 2017, Multi-Shield Spinal Access Systems, Medos International Sàrl.
U.S. Appl. No. 15/786,846, filed Oct. 18, 2017, Devices and Methods for Surgical Retraction, Medos International Sàrl.
U.S. Appl. No. 15/786,858, filed Oct. 18, 2017, Devices and Methods for Providing Access, Medos International Sàrl.
U.S. Appl. No. 15/786,891, filed Oct. 18, 2017, Surgical Access Port Stabilization, Medos International Sàrl.
U.S. Appl. No. 15/786,923, filed Oct. 18, 2017, Surgical Instrument Connectors and Related Methods, Medos International Sàrl.
U.S. Appl. No. 15/901,435, filed Oct. 18, 2017, Surgical Instrument Connectors and Related Methods, Medos International Sàrl.
U.S. Appl. No. 15/931,839, filed May 14, 2020, Surgical Access Port Stabilization, Medos International Sàrl.
U.S. Appl. No. 15/966,293, filed Apr. 30, 2018, Neural Monitoring Devices and Methods, DePuy Synthese Products, Inc.
U.S. Appl. No. 16/352,654, filed Mar. 31, 2019, Multi-Shield Spinal Access System, Medos International Sàrl.
U.S. Appl. No. 16/362,497, filed Mar. 22, 2019, Surgical Instrument Connectors and Related Methods, Medos International Sàrl.
U.S. Appl. No. 16/985,200, filed Aug. 4, 2020, Devices and Methods for Providing Surgical Access, Medos International Sàrl.
U.S. Appl. No. 17/089,695, filed Nov. 4, 2020, Multi-Shield Spinal Access System, Medos International Sàrl.
U.S. Appl. No. 17/159,129, filed Jan. 26, 2021, Multi-Shield Spinal Access System, Medos International Sàrl.
U.S. Appl. No. 17/192,889, filed Mar. 5, 2021, Surgical Visualization Systems and Related Methods, Medos International Sàrl.
U.S. Appl. No. 17/214,759, filed Mar. 26, 2021, Multi-Shield Spinal Access System, Medos International Sàrl.
U.S. Appl. No. 17/692,942, filed Mar. 11, 2022, Multi-Shield Spinal Access System, Medos International Sàrl.
U.S. Appl. No. 17/728,967, filed Apr. 25, 2022, Surgical Visualization Systems and Related Methods, Medos International Sàrl.
U.S. Appl. No. 17/740,305, filed May 9, 2022, Surgical Visualization Systems and Related Methods, Medos International Sàrl.
U.S. Appl. No. 17/884,523, filed Aug. 9, 2022, Surgical Instrument Connectors and Related Methods, Medos International Sàrl.
U.S. Appl. No. 18/091,255, filed Dec. 29, 2022, Multi-Shield Spinal Access System, Medos International Sàrl.
U.S. Appl. No. 18/401,037, filed Dec. 29, 2023, Multi-Shield Spinal Access System, Medos International Sàrl.
U.S. Appl. No. 18/479,048, filed Sep. 30, 2023, Surgical Visualization Systems and Related Methods, Medos International Sàrl.
U.S. Appl. No. 18/479,058, filed Sep. 30, 2023, Surgical Access Port Stabilization, Medos International Sàrl.
U.S. Appl. No. 18/479,059, filed Sep. 30, 2023, Devices and Methods for Providing Surgical Access, Medos International Sàrl.
U.S. Appl. No. 18/987,841, filed Dec. 19, 2024, Multi-Shield Spinal Access System, Medos International Sàrl.
European Search Report for Application No. 24190243.6 issued Mar. 12, 2025 (8 pages).

* cited by examiner

SURGICAL INSTRUMENT CONNECTORS AND RELATED METHODS

CROSS-REFERENCE TO RELATED APPLICATIONS

This application is a continuation of U.S. application Ser. No. 17/884,523, filed Aug. 9, 2022. U.S. application Ser. No. 17/884,523 is continuation of U.S. application Ser. No. 16/362,497, filed Mar. 22, 2019, now issued as U.S. Pat. No. 11,439,380. U.S. Application No. 16,362,497 is a continuation-in-part of U.S. application Ser. No. 15/786,923, filed Oct. 18, 2017, now issued as U.S. Pat. No. 10,869,659. U.S. application Ser. No. 15/786,923 claims priority to U.S. Provisional Application No. 62/468,475, filed Mar. 8, 2017. U.S. application Ser. No. 15/786,923 is also a continuation-in-part of U.S. application Ser. No. 15/437,792, filed Feb. 21, 2017, now issued as U.S. Pat. No. 10,874,425. U.S. application Ser. No. 15/437,792 is a continuation-in-part of U.S. application Ser. No. 15/254,877, filed Sep. 1, 2016, now issued as U.S. Pat. No. 10,987,129. U.S. application Ser. No. 15/254,877 claims priority to U.S. Provisional Application No. 62/214,297, filed Sep. 4, 2015. The entirety of each of these applications is hereby incorporated by reference herein.

FIELD

Surgical instrument connectors and related methods are disclosed herein, e.g., for connecting a surgical access device to a support or anchor.

BACKGROUND

There are many instances in which it may be desirable to connect or link one instrument or object to another instrument or object. In surgical applications, for example, it may be desirable to stabilize an access device (e.g., a cannula, a retractor, etc.) positioned in an incision formed in a patient by connecting the access device to a support.

SUMMARY

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. In some embodiments, a connector can include one or more rigid arms that engage with an attachment feature, where the attachment feature can receive an object therein. The attachment feature can have an unlocked state, in which the position and orientation of an object received within the attachment feature can be adjusted relative to the attachment feature, and a closed state, in which movement of the object relative to the attachment feature is prevented or limited. The connector can have an unlocked state, in which the position and orientation of the access device can be adjusted relative to the support, and a locked state in which movement of the access device relative to the support is prevented or limited. Locking the connector can also be effective to clamp or otherwise attach the connector to the access device and the support, or said attachment can be independent of the locking of the connector.

In some embodiments, a connector can include at least one arm having a plurality of nested segments and an attachment feature for attaching an instrument to the arm; and a handle, wherein the handle is movable between a first position in which the plurality of nested segments are movable relative to one another and a second position in which the plurality of nested segments are fixed relative to one another.

The at least one arm can include first and second arms having respective first and second attachment features, wherein the attachment features are movable in one or more degrees of freedom relative to one another when the handle is in the first position, and wherein said one or more degrees of freedom are locked when the handle is in the second position. Movement of the handle to the second position can be effective to lock movement of the first arm, lock movement of the second arm, lock the first attachment feature to a first instrument, and lock the second attachment feature to a second instrument. Movement of the handle to the first position can be effective to restore movement of the first arm, restore movement of the second arm, unlock the first attachment feature from the first instrument, and unlock the second attachment feature from the second instrument.

The connector can include an actuation wire extending through the plurality of nested segments, wherein the handle in the second position increases tension on the actuation wire to fix the segments and wherein the handle in the first position decreases tension on the actuation wire to allow movement between the segments. The actuation wire can be coupled to the attachment feature such that increasing tension on the actuation wire closes the attachment feature. The handle can include a wire track in which a portion of the actuation wire is disposed, the wire track being open to an exterior side surface of the handle to allow the wire to be introduced laterally into the wire track. The handle can include a bearing element engaged with the actuation wire. Movement of the handle can cause translation of the bearing element along a tension axis, thereby increasing or decreasing tension applied to the actuation wire. The handle can include first and second branches, each being operatively associated with an arm of the connector, the branches defining a cavity therebetween. The bearing element can be mounted on a plate slidably disposed in the cavity. Opposed edges of the plate can be slidably disposed within corresponding tracks formed in the branches.

The connector can include an actuation shaft disposed within a lumen of the handle. The connector can include a linkage bar coupled to a movable handle lever of the handle and to the actuation shaft. The connector can include an adjustment knob threadably mated to the actuation shaft to form an assembly, wherein rotation of the adjustment knob adjusts the length of the assembly as measured along a tension axis, thereby adjusting the amount of tension applied to an actuation wire of the at least one arm when the handle is moved between the first and second positions. The connector can include a locking mechanism for selectively maintaining the handle in at least one of the first and second positions. The locking mechanism can include a movable handle lever pivotally coupled to a linkage bar and configured to enter an over-center condition when the handle is in the second position. The plurality of nested segments can be configured to pitch, yaw, and roll relative to one another when the handle is in the first position. The attachment feature can define a central opening through which an instrument or other object can be received. The attachment feature can apply a pre-load or provisional friction fit to an object received therein when the handle is in the first position.

The attachment feature can include at least one of a ring clamp, a lasso, an end-loading jaw, a side-loading jaw, and a spherical clamp. The handle can be biased towards the second position. The connector can include a spring element that biases the handle towards the second position, wherein the spring element urges an actuation wire extending through the at least one arm in a proximal direction to apply tension thereto. Moving the handle to the first position can compress the spring element to reduce tension applied to the actuation wire. The handle can include a scissor linkage that expands to compress the spring element when the handle is in the first position. The at least one arm can include first and second arms, and the handle can include a fixed handle lever, a first movable handle lever movable with respect to the fixed handle lever to lock the first arm, and a second movable handle lever movable with respect to the fixed handle lever to lock the second arm.

In some embodiments, a surgical method can include positioning a surgical access device relative to a patient; attaching the access device to a first arm of a connector; attaching a second arm of the connector to a support; articulating a plurality of nested segments of at least one of the first and second arms to adjust a position and orientation of the access device relative to the support; and locking the connector to maintain the access device and the support in the adjusted position and orientation.

The support can include an anatomical structure of the patient or an implant implanted in the patient. The support can include a patch or other object secured or placed on the patient. The support can be mounted to the skin of a patient. The support can be mounted to a pedicle of the patient. The connector can provide a range of movement between the access device and the support that is unrestricted within the environment of lumbar posterior access spine surgery. Locking the connector can lock multiple degrees of freedom between the access device and the support simultaneously with a single action. Locking the connector can be effective to, simultaneously and with a single action, lock the access device to the first arm, lock the support to the second arm, and lock multiple degrees of freedom between the access device and the support. Positioning the access device can include inserting the access device into a patient such that a distal end of the access device is disposed within or proximate to an intervertebral disc space of the patient. The support can be mounted to a vertebral bone structure disposed on a side of the disc space that is ipsilateral to the access device. The support can be mounted to a vertebral bone structure disposed on a side of the disc space that is contralateral to the access device. At least a portion of the second arm can be positioned beneath a skin surface of the patient. The method can include delivering a fusion cage through the access device to an intervertebral disc space of the patient. The method can include performing a discectomy through the access device.

Locking the connector can be done by applying a user input force to the connector using only one hand. Locking the connector can include removing a user input force from first and second handle levers of the connector. In some embodiments, locking the connector does not move the access device or the support relative to the patient. The access device can include a tissue retractor. Positioning the access device can include supporting or retracting tissue using the access device. The tissue can be an abdominal shelf of the patient, a breast of the patient, a rectum of the patient, or an anus of the patient. The access device can include a trans-anal port. The method can include using a third arm of the connector to hold a light source or an instrument inserted into the access device. The method can include positioning a distal end of the access device in proximity to an odontoid of the patient, the connector maintaining the access device at a fixed trajectory relative to the odontoid, and inserting a screw through the access device and into the odontoid.

The access device can include a first skull port and the support can include a second skull port. The method can include delivering material through the first skull port and aspirating material from the second skull port. The method can include evacuating at least one of an epidural hematoma, a subdural hematoma, a hygroma, frontal bone, and parietal bone through at least one of the skull ports. The support can include a screw or nail previously implanted in the patient. The support can include a bone plate. The method can include delivering a bone anchor through the access device and into an opening formed in the bone plate. The support can include an implanted fixation construct. The method can include delivering a component of the construct through the access device and attaching said component to the implanted fixation construct.

The method can include positioning a distal end of the access device in proximity to a bone fracture of the patient, the connector maintaining the access device at a fixed trajectory relative to the fracture, and inserting a screw or nail through the access device to reduce the fracture. The fracture can be in a tibial plateau, a navicular bone, or a long bone. The method can include holding a bone fragment in place using the access device while delivering the screw or nail through the access device. The method can include holding a bone fragment in place using a third arm of the connector while delivering a screw or nail through the access device. The method can include attaching a bone fragment to the connector, manipulating an arm of the connector to position the bone fragment in a desired location relative to the fracture, and locking the connector to hold the bone fragment in the desired location. The method can include positioning a distal end of the access device in alignment with an opening formed in an intramedullary device implanted in the patient, the connector maintaining the access device at a fixed trajectory relative to the opening, and delivering a locking screw through the access device into the opening. The support can include the intramedullary device or an inserter instrument coupled thereto.

In some embodiments, a surgical method can include inserting a first needle into a patient; inserting a second needle into the patient; coupling the first and second needles to respective arms of a connector, the arms comprising a plurality of nested segments and the connector being selectively lockable to prevent movement between the plurality of nested segments; and locking the connector to automatically position the first and second needles in a predetermined position and orientation relative to one another and to lock movement between the first and second needles. The predetermined orientation can be one in which the first and second needles are parallel.

In some embodiments, a surgical method can include forming first and second discrete skin portals into a joint of a patient; inserting a visualization device through the first skin portal; inserting a surgical instrument through the second skin portal; attaching the visualization device to a first arm of a connector; attaching the surgical instrument to a second arm of the connector; positioning a distal end of the instrument within a field of view of the visualization device;

and locking the connector to prevent relative movement of the first and second arms and thereby maintain the distal end of the instrument in the field of view of the visualization device.

The joint can include a knee joint. The visualization device can include an arthroscope. The surgical instrument can include a shaver, cutter, or drill.

In some embodiments, a surgical method can include implanting a bone anchor in a pedicle of a patient's spine, the bone anchor having an extension extending proximally therefrom; attaching a first arm of a connector to the extension; inserting an access device via a transforaminal approach to position a distal end of the access device in alignment with an intervertebral disc space of the patient's spine; attaching a second arm of the connector to the access device; articulating the first and second arms of the connector at a plurality of nested segments thereof to adjust a position of the access device relative to the extension; locking the connector to restrict articulation of the plurality of nested segments and maintain a relative positioning of the access device and the extension; and passing a fusion cage through the access device and into the disc space.

The method can include applying a user input force to the connector to unlock the connector; adjusting the relative positioning of the access device and the extension; and removing the user input force from the connector, thereby automatically relocking the connector.

In one aspect, a connector can include a rigid arm defining an inner passage extending between a proximal end and a distal end of the arm, an actuation shaft slidably received within the inner passage, and an attachment feature connected to the distal end of the arm, where the attachment feature can engage an object therein. The connector further includes a handle axially centered with respect to an axis of the connector, where rotation of the handle about the axis translates the actuation shaft within the inner passage of the rigid arm.

The connector described above can have a number of additional features and/or variations, all of which are within the scope of the present disclosure. In some embodiments, the connector can further include an engagement feature located at a distal end of the actuation shaft. The engagement feature can have an open position, in which the engagement feature can receive the attachment feature, and a closed position, in which the engagement feature can hold the attachment feature in contact with the distal end of the rigid arm.

In some embodiments, the connector can further include a second attachment feature. The second attachment feature can have a first receiving recess, a second receiving recess, and a locking element. The first receiving recess can receive the rigid arm such that the second attachment feature can translate along the rigid arm, and the locking element can selectively lock the second attachment feature with respect to the rigid arm.

In still other embodiments, the inner passage of the rigid arm can be coaxially aligned with an inner passage of the handle such that a proximal portion of the actuation shaft is received within the inner passage of the handle. Further, in some embodiments, rotation of the handle in a first direction can draw the actuation shaft proximally into the handle to lock the attachment feature to the rigid arm.

In another aspect, a connector can include a first rigid arm having a first inner passage extending between a proximal end and a distal end of the first rigid arm, and a second rigid arm having a second inner passage extending between a proximal end and a distal end of the second rigid arm. The connector can further include a first and second actuation shaft slidably received in the respective first and second inner passages, and a first and a second attachment feature coupled to the respective distal ends of the first and second rigid arms. An actuation assembly having a proximal end and a distal end defining a connector axis can be operatively connected to the first and second actuation shafts. A handle can be located at the proximal end of the actuation assembly, where rotation of the handle about the connector axis places the first and second attachment features in a locked position.

The connector described above can have a number of additional features and/or variations, all of which are within the scope of the present disclosure. In some embodiments, the first and second rigid arms can be selectively rotatable relative to the connector axis and relative to each other. Further, in some embodiments, rotation of the handle in a first direction can restrict rotation of the first and second arms relative to the connector axis and relative to each other. In certain embodiments, the proximal ends of the first and second rigid arms can be coaxially aligned with the connector axis.

In other embodiments, the distal ends of the first and second rigid arms can be securely received within the respective first and second attachment features. Further, in some embodiments, the distal ends of the first and second rigid arms can include a distal flange that defines a circumferential groove, where the first attachment feature can engage with the circumferential groove of the first arm to secure the first arm within the first attachment feature, and the second attachment feature can engage with the circumferential groove of the second arm to secure the second arm within the second attachment feature. Further, in some other embodiments, the distal ends of the first and second actuation shafts can engage with a portion of the respective first and second attachment features such that the actuation shaft is coupled to the first and second attachment features.

In some embodiments, the actuation assembly can convert rotational motion of the handle to translate the first and second actuation shafts radially with respect to the connector axis along the respective first and second inner passages.

In some embodiments, the actuation assembly can include a control shaft extending along the connector axis. The control shaft can be operatively connected to the first and second actuation shafts such that movement of the control shaft along the connector axis results in translation of the first and second actuation shafts. Further, in some embodiments, the handle can rotatably receive a proximal end of the control shaft, such that rotation of the handle in a first direction causes the control shaft to move proximally with respect to the handle, while rotation of the handle in a second direction causes the control shaft to move distally with respect to the handle.

In some embodiments, at least one of the first and second attachment features can include a jaw clamp. The jaw clamp can move between an open position and a closed position with translation of the respective first or second actuation shafts.

In another aspect, a surgical method for connecting a first object and a second object can include positioning a surgical access device relative to a patient, attaching the surgical access device to a first attachment feature of a first arm of a connector, positioning a second arm of the connector to receive a support, and rotating a handle of the connector to lock the surgical access device to the first arm and to lock the support to the second arm.

The surgical method described above can have a number of additional features and/or variations, all of which are within the scope of the present disclosure. In some embodiments, rotating the handle of the connector causes a first actuation shaft to translate distally along the first arm to lock the surgical access device to the first arm and causes a second actuation shaft to translate distally along the second arm to lock the support to the second arm.

In other embodiments, rotating the handle draws a control shaft of the connector proximally along a connector axis to lock the surgical access device to the first arm, the support to the second arm, and the first arm and the second arm relative to each other.

In some embodiments, attaching the surgical device can include attaching the surgical device to a first attachment feature and coupling the first attachment feature with an engagement feature of the first arm. Furthermore, rotating the handle can lock the surgical access device to the first arm by restricting movement of the first attachment feature with respect to the first arm.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Figure 1:
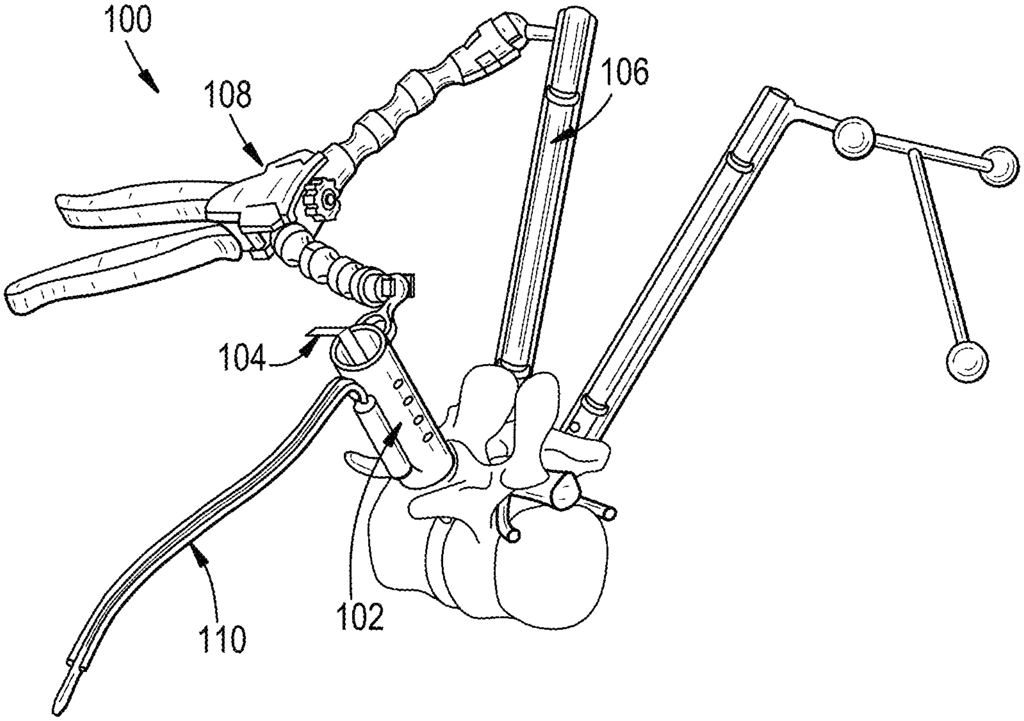
FIG. 1 is a perspective view of a surgical system in use to perform a surgical procedure on a patient's spine.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. The connector can have an unlocked state, in which the position and orientation of the access device can be adjusted relative to the support, and a locked state in which movement of the access device relative to the support is prevented or limited. Locking the connector can also be effective to clamp or otherwise attach the connector to the access device and the support, or said attachment can be independent of the locking of the connector.

The connectors described herein can include any one or more of the following features. The connector can be configured to rigidly fix the position and orientation between two or more attached objects, e.g., such that the position and orientation between the attached objects does not change when those objects are subjected to the manipulations and forces that are typical of spinal surgery. The connector can be configured to lock and unlock with a simple one-handed manipulation. The connector can be configured such that locking and unlocking the connector does not apply significant resultant forces on the attached objects, other than forces associated with attachment of those objects to the connector. In other words, the connector can be configured such that it can be locked and/or unlocked without appreciably moving the objects attached thereto relative to the patient. The connector can be attached to an access device and a pedicle-mounted support and can provide a range of movement therebetween that is unrestricted within the environment of lumbar posterior access spine surgery. The connector can be configured to attach to various objects with a simple click-on or dock-on attachment mechanism.

The connector can allow for a strong connection to attached objects, minimizing any toggle or movement between the object and the connector when the connector is locked. The connector can provide mechanical advantage in locking and/or unlocking the connector, e.g., to obtain a locking force that is significantly greater than the user input force. The connector can allow for a high range of adjustability or freedom of movement between attached objects when the connector is unlocked. The connector can be configured to quickly and efficiently lock multiple degrees of freedom (DOF) between attached objects. The connector can be configured to quickly and efficiently attach and detach from objects. The connector can be configured to simultaneously lock onto multiple objects and to lock the position and orientation between those objects with the same single action. The connector can be configured such that the connector can be made completely flexible or completely stiff quickly and easily using a simple one-handed actuation motion. This can allow the positioning of attached objects to be adjusted with minimal disruption to surgical flow.

In some embodiments, a connector can be actuated to simultaneously, and in a single action, lock or unlock (i) a first instrument to the connector, (ii) a second instrument to the connector, and (iii) one or more degrees of freedom between the first and second instruments.

The connectors described herein can be used in various types of surgery, including spinal surgery. Exemplary spinal surgeries can include lumbar spine minimally-invasive surgery (MIS). The connectors described herein can be used to connect an access channel, retractor, tube, etc. to the anatomy of the vertebral segment (e.g., via a pedicle post or other support) that is being operated on, instead of or in addition to connecting it to the operating table. In some arrangements, the connector can be used to connect the access device to the operating table.

The connectors described herein can be configured to allow the access device to remain fixed relative to the patient's anatomy, even if the position of the patient's anatomy changes during the surgery. The connector can thus maintain a consistent field of view through the access device, eliminating the need to readjust the access device if the patient moves. The connector can have a slim or low-profile form factor as compared to traditional retractor equipment.

The connectors described herein can support an access device relative to a patient to facilitate hands-free operation. In other words, a surgeon or other user is not required to manually hold the connector or the access device during use, and therefore the user's hands can be freed to perform other tasks. The connector can be used to support an access device having an integrated or attached camera or other visualization device, such that the visualization device is supported by the access device in a hands-free manner. Thus, the connector can facilitate hands-free surgical visualization, as the surgeon or other user is not required to manually hold the connector, the access device, or the visualization device during use in a surgery.

The connectors described herein can be configured to attach a first part (such as an anatomic anchor) to a second part (such as an access tube or retractor) in a way that is easy and quick for the user to attach the connector, detach the connector, and to change the position between the two parts during the surgery.

FIG. 1 illustrates an exemplary surgical system 100 in which the devices and methods described herein can be used, though it will be appreciated that such devices and methods can be used in various other applications instead or in addition. Further details on the system of FIG. 1 can be found in U.S. application Ser. No. 15/437,792 filed on Feb. 21, 2017, now issued as U.S. Pat. No. 10,987,129, which is hereby incorporated by reference herein. The system 100 can be used in various surgical procedures, including spinal surgeries such as microsurgical bone resection, spinal decompression, spinal fusion, and the like. In general, the system 100 can include any one or more of an access device 102, a tissue retractor 104, a pedicle post or other anchor 106, a connector 108, and a camera 110. Exemplary access devices 102 are disclosed in U.S. application Ser. No. 15/786,858 entitled DEVICES AND METHODS FOR PROVIDING SURGICAL ACCESS, now issued as U.S. Pat. No. 10,758,220. Exemplary tissue retractors 104 are disclosed in U.S. application Ser. No. 15/786,846 entitled DEVICES AND METHODS FOR SURGICAL RETRACTION, now issued as U.S. Pat. No. 10,779,810. Exemplary anchors 106 are disclosed in U.S. application Ser. No. 15/786,891 entitled SURGICAL ACCESS PORT STABILIZATION, now issued as U.S. Pat. No. 10,682,130. Exemplary connectors 108 are disclosed herein. Exemplary cameras 110 are disclosed in U.S. application Ser. No. 15/692,845 entitled SURGICAL VISUALIZATION SYSTEMS AND RELATED METHODS, now issued as U.S. Pat. No. 11,331,090. Each of the above applications is hereby incorporated by reference herein.

An exemplary method of using the system 100 of FIG. 1 can include any one or more of the following steps, performed in any of a variety of sequences: a) making an incision in a skin of a patient; b) percutaneously inserting through the incision an access device 102 having a substantially tubular shape (such as a tube or a multi-slotted retractor), the access device having a length adapted to extend from the incision to a border between sensitive and insensitive tissue (e.g., a superior articular process (SAP), or a lamina) in the spine of the patient; c) stabilizing the access device to an anchor 106 (e.g., a pedicle anchor) using a connector 108; d) inserting an access device integrated optical visualization instrument 110; e) resecting a portion of the superior articular process, and/or performing a microsurgical decompression procedure; f) inserting or deploying a tissue retractor 104 through or from the access device so that a distal end portion of the tissue retractor extends to the intervertebral disc, the retractor having an outer surface; g) contacting the outer surface of the retractor to a nerve root to shield the nerve root; h) microsurgically decompressing any tissue deemed to be causing nerve impingement; i) extracting intervertebral disc material including removing cartilaginous material from the vertebral endplates; j) inserting an interbody device; and k) deploying a mechanism of stabilization to stabilize the intervertebral segment.

FIGS. 2A-2G illustrate an exemplary connector 200 that can be used to connect a first object to a second object. For example, the connector 200 can be used to connect first and second surgical instruments. By way of further example, the connector 200 can be used in the system 100 described above, e.g., to connect the access device 102 to the support or anchor 106.

As shown, the connector 200 can include a handle assembly 202 and an arm assembly 204. The arm assembly 204 can include at least one arm 206 configured to transition between a fixed state and a movable state. The arm 206 can include an attachment feature 208 for attaching the arm to an instrument, a support, or some other object. The arm 206 can include a first end coupled to the handle assembly 202 and a second end at which the attachment feature 208 is disposed. The arm 206 can include a plurality of nested segments 210 threaded onto a wire or cable 212. The wire or cable 212 can also be operatively coupled with the attachment feature 208 of the arm 206. In an exemplary arrangement, each nested segment 210 of the arm 206 can pivot or rotate with respect to adjacent segments, allowing movement of the second end of the arm relative to the first end of the arm. In arrangements with multiple arms 206, each arm can be independently movable, such that an object coupled to a first arm can be moved relative to an object coupled to a second arm in at least six degrees of freedom. In use, tension on the wire 212 can be relaxed to allow the arm 206 to articulate. Relaxing the tension on the wire 212 can also be effective to release the attachment feature 208 from an object received therein. When a desired positioning of the arm 206 is achieved, tension can be increased or restored to the wire 212 to lock the arm in the desired position. Increasing tension on the wire 212 can also be effective to close, clamp, or otherwise engage the attachment feature 208 with an object received therein.

The handle assembly 202 can be actuated by a user to selectively apply or release tension, or to selectively increase or decrease tension, from the wire 212 of the arm assembly 204. The handle assembly 202 can include a handle frame 214 and one or more handle levers 216. While a fixed handle lever 216A and a movable handle lever 216B are shown, it will be appreciated that the handle assembly 202 can include any number of fixed and/or movable handle levers. The handle assembly 202 can include a pulley or other bearing element 218 that is engaged with the wire 212 of the arm assembly 204. Actuation or movement of the handle assembly 202 can cause the pulley 218 to translate along a tension axis A1 to increase or decrease tension on the wire 212. For example, squeezing the handle levers 216 together to a "closed" position can cause the pulley 218 to translate along the axis A1 in a proximal direction, applying tension to the wire 212 of the arm assembly 204. Moving the handle levers 216 apart to an "open" position can cause the pulley 218 to translate along the axis A1 in a distal direction, relaxing the tension applied to the wire 212. An adjustment knob 220 can be rotated to fine-tune the amount of tension applied to the wire 212 in the closed and open positions of the handle assembly 202. As described further below, in other arrangements, squeezing the handle levers 216 together can be effective to reduce the tension on the wire 212 and releasing the handle levers can be effective to increase the tension on the wire.

In some arrangements, the handle assembly 202 can be reusable and the arm assembly 204 can be a single-use disposable. The connector 200 can be provided as a kit with a plurality of different handle assemblies and/or a plurality of different arm assemblies, with the components of the kit being freely interchangeable by the user as needed or desired.

Figure 2A:
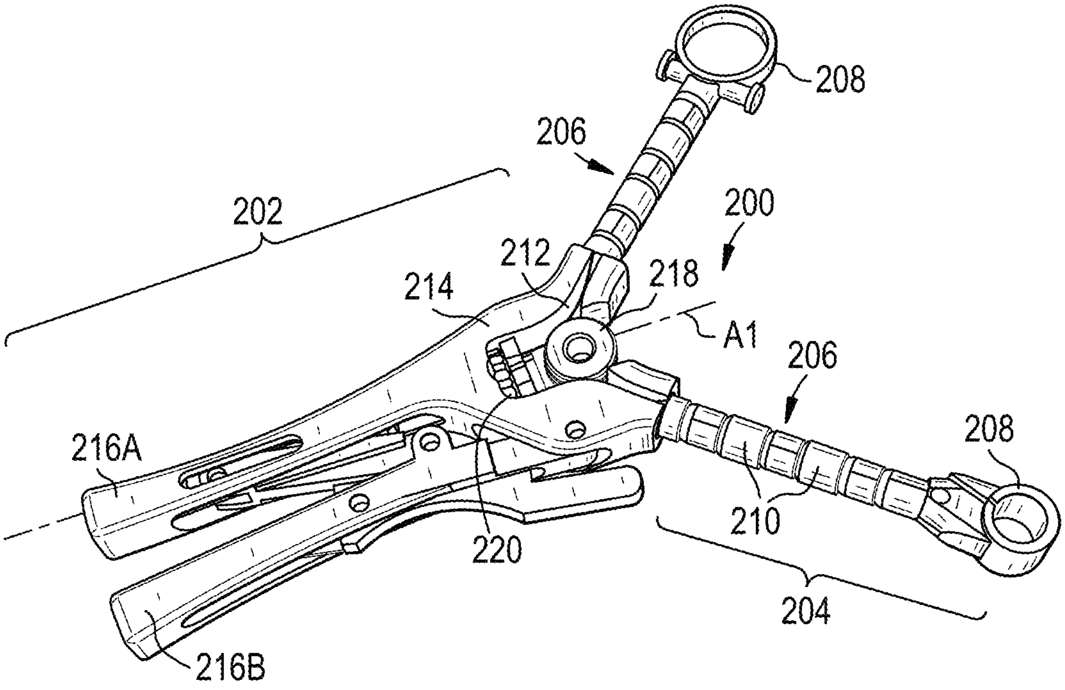
FIG. 2A is a perspective view of a connector.
Figure 2B:
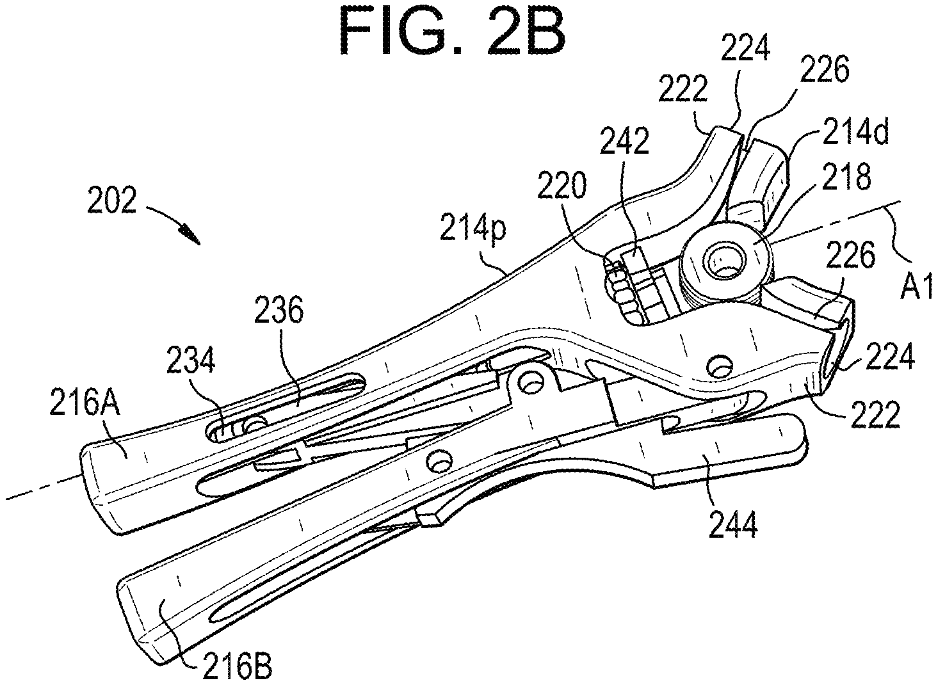
FIG. 2B is a perspective view of a handle assembly of the connector of FIG. 2A.
Figure 2C:
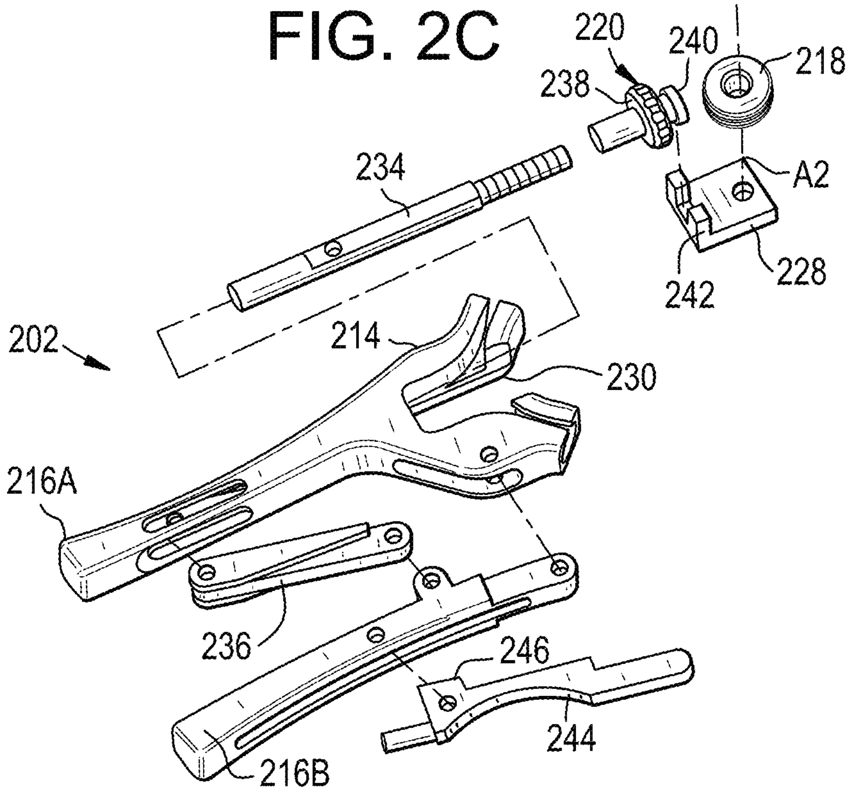
FIG. 2C is an exploded perspective view of the handle assembly of FIG. 2B.
Figure 2D:
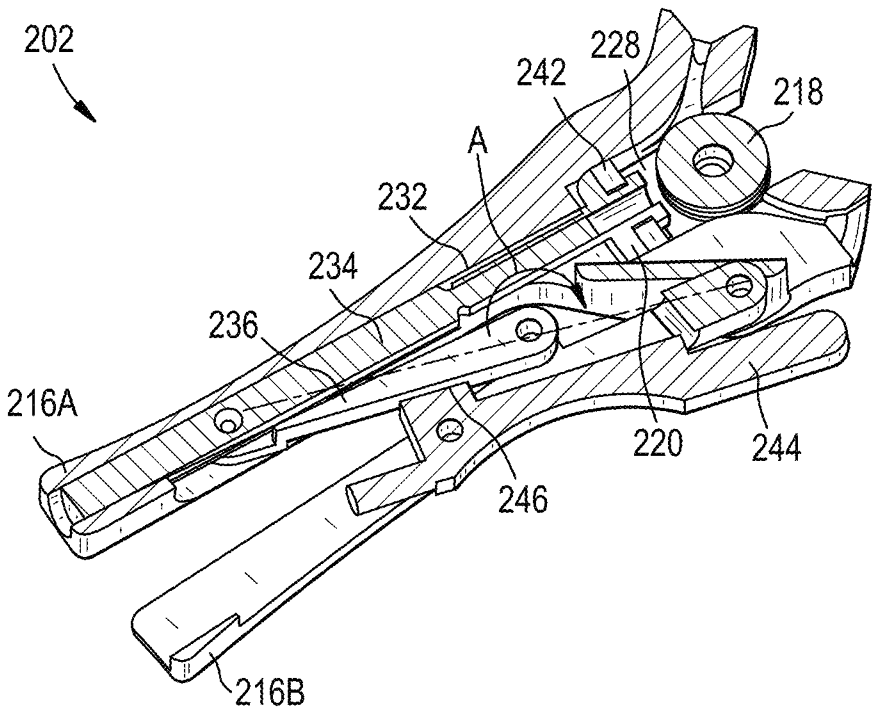
FIG. 2D is a sectional perspective view of the handle assembly of FIG. 2B.

The handle assembly 202 is shown in greater detail in FIGS. 2B-2D. The handle frame 214 can include proximal and distal ends 214*p*, 214*d* that define a longitudinal or proximal-distal axis A1. The distal end 214*d* of the handle frame 214 can define one or more branches 222, each being operatively associated with a respective arm 206 of the arm assembly 204. In the illustrated embodiment, the handle frame 214 includes first and second branches 222 associated with first and second arms 206 of the arm assembly 204, respectively. Each branch 222 can include a mating interface 224 that receives the proximal-most segment 210 of its respective arm 206. The mating interface 224 can be a spherical or substantially spherical depression or protrusion. The mating interface 224 can include a key or a keyway configured to receive a counterpart component of the proximal-most segment 210 of the arm 206, e.g., to limit movement of said segment relative to the branch 222 in one or more degrees of freedom. The branch 222 can include a wire track 226 through which the wire 212 of the arm assembly 204 can be routed. The wire track 226 can be open to at least one exterior surface of the handle frame 214. This can allow the wire 212 to be easily side-loaded or otherwise introduced into the wire track 226 during assembly of the handle frame 214 to the arm assembly 204.

The tension pulley 218 can be mounted within a cavity defined between the branches 222 of the handle frame 214. The tension pulley 218 can be a cylindrical or substantially cylindrical body with a circumferential track formed in an exterior surface thereof for receiving the wire 212. The tension pulley 218 can be mounted to a sliding plate 228 via a pin or axle received through a central opening of the tension pulley. The tension pulley 218 can be rotatable relative to the plate 228 about an axis A2, or can be fixed relative to the plate. Opposed lateral edges of the plate 228 can include a mating feature slidably mounted within a counterpart mating feature of the branches 222. For example, the opposed lateral edges of the plate 228 can act as male mating features and can be received with respective grooves 230 formed in the branches 222 to act as female mating features. The edges of the plate 228 can be chamfered or tapered as shown, and the slots 230 can have a corresponding but negative geometry. In other arrangements, the branches 222 can include a raised ridge received within a corresponding slot formed in the plate 228. The plate 228 can be slidably mounted to the branches 222, such that the plate can translate relative to the handle frame 214 along the axis A1.

Movement of the plate 228 and, by extension, the tension pulley 218 along the axis A1 can be controlled by actuation of one or more handle levers 216 of the handle assembly 202. While a fixed handle lever 216A and a movable handle lever 216B are shown, it will be appreciated that the handle assembly 202 can include any number of fixed and/or movable handle levers. The movable handle lever 216B can be pivotally mounted to the handle frame 214. For example, the distal end of the movable handle lever 216B can be attached to the proximal end of the handle frame 214 by a pivot pin. The fixed handle 216A can be formed integrally with the handle frame 214, or can be rigidly fixed thereto.

The handle frame 214 can define an interior channel or lumen 232 in which an actuation shaft 234 is slidably disposed such that the actuation shaft can translate along the axis A1 relative to the handle frame. The channel 232 can extend into the fixed handle lever 216A. A linkage bar 236 can be coupled to the movable handle lever 216B and to the actuation shaft 234 via respective pivot pins.

The distal end of the actuation shaft 234 can be received within an opening formed in the adjustment knob 220. The actuation shaft 234 can include an external thread that engages with an internal thread of the adjustment knob 220. The actuation shaft 234 and the adjustment knob 220 can collectively form an actuation shaft assembly. Rotation of the adjustment knob 220 relative to the actuation shaft 234 can adjust the effective length of the assembly as measured along the axis A1, and thereby adjust the amount of tension applied to the wire 212 when the handle assembly 202 is actuated. The adjustment knob 220 can include a wheel 238 that protrudes above an exterior surface of the handle frame 214 such that the knob can be rotated by a user. The wheel 238 can be knurled or can include other gripping features to facilitate such rotation. The wheel 238 can define a distal-facing shoulder. A flange 240 can be formed at the distal end of the adjustment knob 220 to define a proximal-facing shoulder. The plate 228 can include one or more protrusions 242 disposed between the proximal and distal facing shoulders of the adjustment knob 220. Accordingly, translation of the adjustment knob 220 along the axis A1 can be transferred to the plate 228, while still allowing free rotation of the adjustment knob relative to the plate. The plate 228 can include first and second opposed protrusions 242 as shown that define a seat therebetween for receiving the adjustment knob 220.

In operation, movement of the handle levers 216 towards one another can cause the linkage bar 236 to pivot relative to the handle levers. The linkage bar 236 can have a fixed length, such that said pivoting causes the actuation shaft 234 to translate longitudinally along the axis A1 in a proximal direction relative to the handle frame 214. This movement of the actuation shaft 234 can impart corresponding movement to the adjustment knob 220, plate 228, and tension pulley 218, thereby increasing the tension applied to the wire 212 of the arm assembly 204. Movement of the handle levers 216 away from one another can impart opposite movement of the components, translating the tension pulley 218 distally along the axis A1 to decrease the tension applied to the wire 212 of the arm assembly 204. The adjustment knob 220 can be rotated relative to the handle frame 214 about the axis A1 to adjust the tension that is applied to the wire 212. Rotating the adjustment knob 220 in a first direction can be effective to thread the actuation shaft 234 deeper into the adjustment knob, shortening the overall length of the assembly and moving the tension pulley 218 proximally to increase the tension applied to the wire 212. Rotating the adjustment knob 220 in a second, opposite direction can be effective to unthread the actuation shaft 234 from the adjustment knob, lengthening the assembly and moving the tension pulley 218 distally to decrease the tension applied to the wire 212.

The handle assembly 202 can include a locking mechanism for selectively maintaining the handle assembly in the open and/or closed configurations. The locking mechanism can be active while the handle assembly 202 is in the open configuration to lock the handle assembly in the open configuration. The locking mechanism can be active while the handle assembly 202 is in the closed configuration to lock the handle assembly in the closed configuration.

For example, as shown in the illustrated embodiment, the linkage bar 236 can be mounted to the handle levers 216 to achieve an over-center action, in a manner similar to locking pliers, thereby forming a locking mechanism that is active in the closed configuration. As the handle levers 216 are moved towards one another, the linkage bar 236 and the movable handle 216B can enter an over-center condition, locking the handle levers in the closed position. In particular, the angle A shown in FIG. 2D can approach and then exceed 180 degrees as the assembly enters the over-center condition. The handle assembly 202 can include a release lever 244 for moving the assembly out of the over-center condition. The release lever 244 can be pivotally mounted to the movable handle lever 216B. Rotation of the distal end of the release lever 244 towards the movable handle lever 216B can urge a bearing surface 246 of the lever against the linkage bar 236, prying the movable handle lever away from the linkage bar and the fixed handle lever 216A, thereby providing mechanical advantage to the user in moving the handle levers apart. As the handle levers 216 are spread apart, they can move the assembly out of the over-center condition to unlock the connector 200.

Figure 2E:
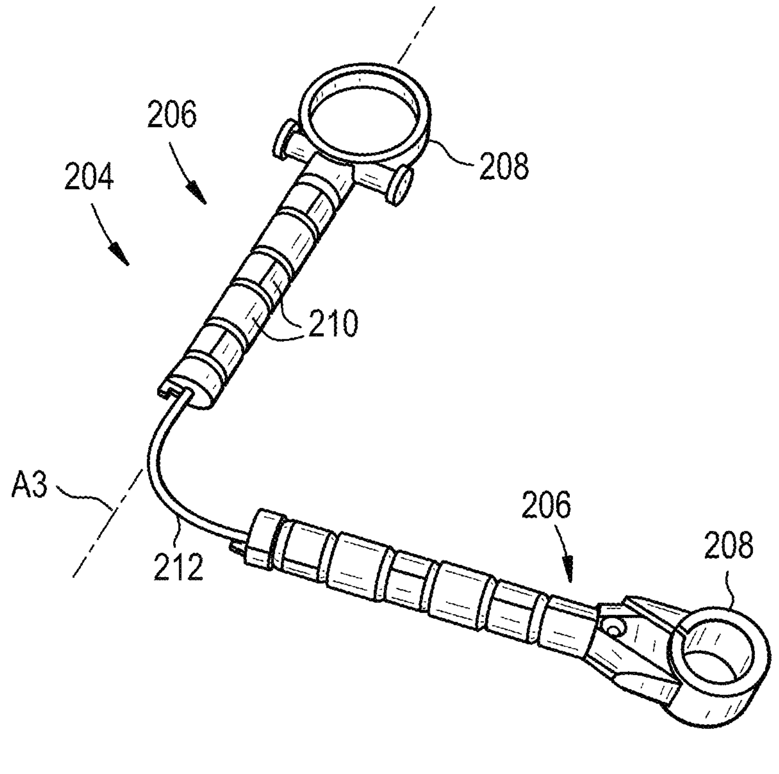
FIG. 2E is a perspective view of an arm assembly of the connector of FIG. 2A.
Figure 2F:
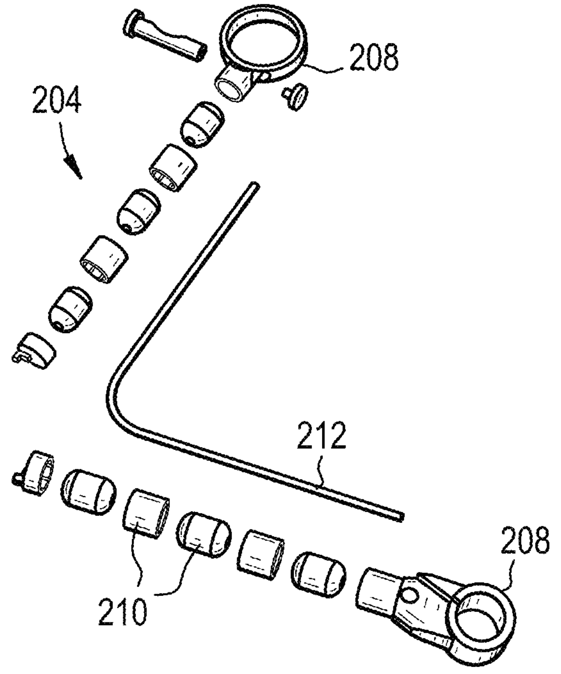
FIG. 2F is an exploded perspective view of the arm assembly of FIG. 2E.
Figure 2G:
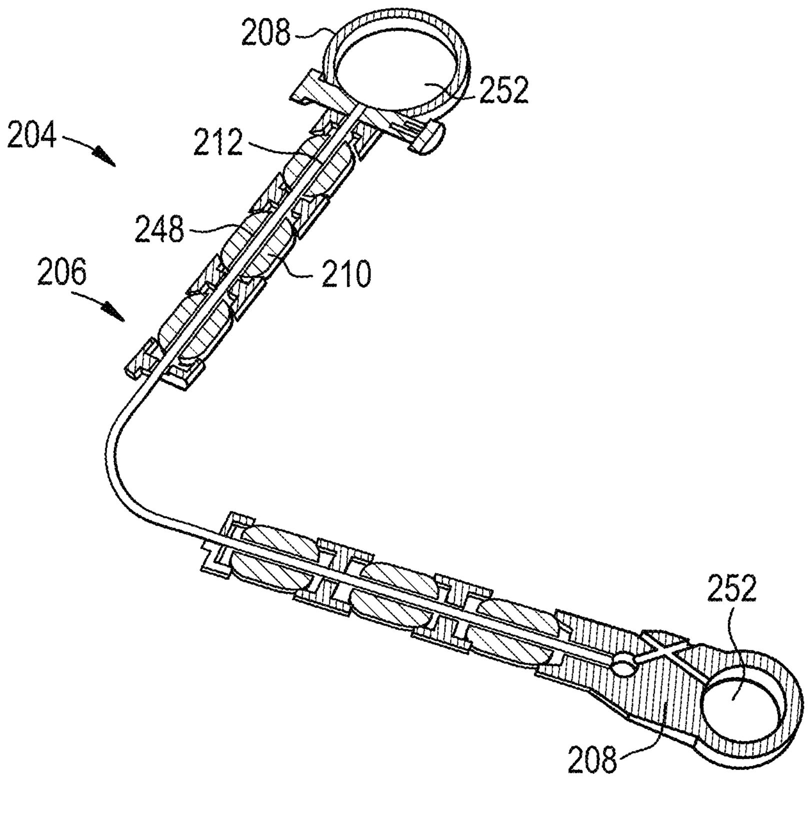
FIG. 2G is a sectional perspective view of the arm assembly of FIG. 2E.

The arm assembly 204 is shown in greater detail in FIGS. 2E-2G. The arm assembly 204 can include at least one arm 206, e.g., first and second arms as shown. The arm 206 can include a plurality of nested segments 210 disposed end-to-end along a neutral axis A3 of the arm. An actuation wire 212 can extend through the segments 210. An attachment feature 208 can be disposed on the arm 206, e.g., at a distal free end of the arm. When tension on the wire 212 is reduced, the segments 210 can be movable with respect to one another in one or more degrees of freedom. For example, in the illustrated arrangement, the segments 210 can pitch, yaw, and roll with respect to one another when the tension on the wire 212 is reduced. In other arrangements, the segments 210 can be movable in fewer degrees of freedom or in additional degrees of freedom. When tension on the wire 212 is increased, the segments 210 can be pulled into firm engagement with one another, resisting or preventing relative movement therebetween. The wire 212 can also be configured to control the attachment feature 208, e.g., such that tension applied to the wire is effective to open or close the attachment feature, or to otherwise connect or disconnect the attachment feature from an attached object. In some embodiments, a single wire 212 can be used to lock and unlock a plurality of arms 206 of the connector 200 and to actuate a plurality of attachment features 208 of the connector. In some embodiments, each arm of the connector can include an independent wire for locking and unlocking said arm and for actuating an attachment feature of said arm. In some embodiments, a single wire can be used to lock and unlock a plurality of arms of the connector and a separate single wire can be used to actuate a plurality of attachment features of the connector.

The plurality of nested segments 210 of each arm 206 can include a proximal-most segment and a distal-most segment. The plurality of nested segments 210 can include one or more intermediate segments disposed between the proximal-most and distal-most segments. The proximal-most segment can include a distal bearing surface that contacts an adjacent segment and a proximal bearing surface that contacts a branch 222 of the handle frame 214. The proximal-most segment can alternatively be attached to the handle frame 214 or formed integrally with the handle frame. The distal-most segment can include a proximal bearing surface that contacts an adjacent segment and a distal bearing surface that contacts an attachment feature 208. The distal-most segment can alternatively be attached to the attachment feature 208 or formed integrally with the attachment feature. Each intermediate segment can include proximal and distal bearing surfaces that contact and bear against counterpart bearing surfaces of adjacent segments.

Each segment 210 can include an inner passage or cannulation 248 through which the wire 212 extends. The inner passage 248 can be cylindrical or substantially cylindrical. The inner passage 248 can have a diameter that is only slightly greater than or equal to the outside diameter of the wire 212. The inner passage 248 can have conical or otherwise-flared sections at the proximal and distal ends thereof to provide a relief for bending of the wire 212 as the arm 206 is articulated.

Figure 3A:
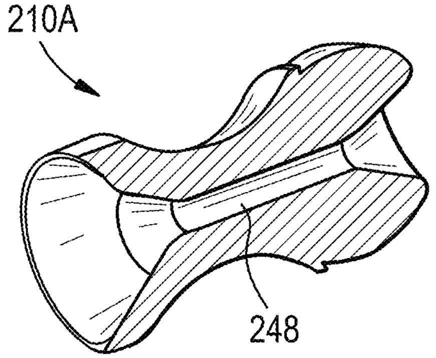
FIG. 3A is a sectional perspective view of a segment that can be used in the connectors herein.
Figure 3B:
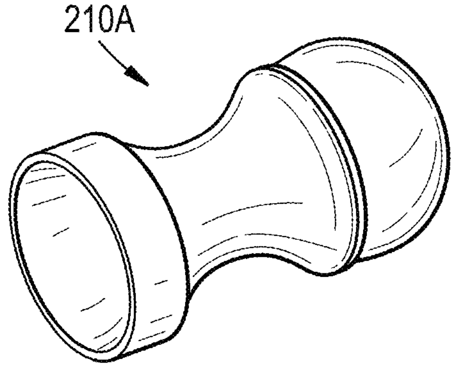
FIG. 3B is a perspective view of the segment of FIG. 3A.
Figure 3C:
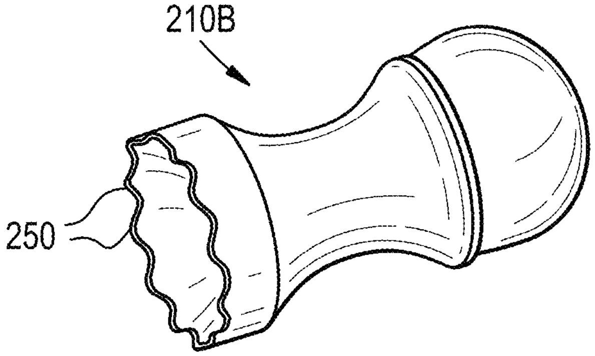
FIG. 3C is a perspective view of another segment that can be used in the connectors herein.

It will be appreciated that the segments 210, and the bearing surfaces thereof, can have any of a variety of geometries. In FIG. 2F, for example, each arm 206 includes alternating male and female segments 210, with the male segments having proximal and distal male bearing surfaces and the female segments having proximal and distal female bearing surfaces. In other arrangements, each segment can have one male bearing surface and one female bearing surface. As shown in FIGS. 3A-3B, a segment 210A can include a spherical male bearing surface at one end (e.g., a distal end or a proximal end) and a spherical female bearing surface at the other end (e.g., a proximal end or a distal end). The segment 210A can include a cylindrical inner passage 248 with opposed conical end sections. As shown in FIG. 3C, a segment 210B can include a ring-shaped terminal end surface that defines a plurality of teeth 250 for enhancing grip with an adjacent segment. A segment 210 can include a cylindrical bearing surface, e.g., to limit articulation with an adjacent segment to uniplanar movement. A segment 210 can include rotation stops to limit the degree to which the segment can rotate relative to an adjacent segment.

The segments 210 of the arm assembly 204 can include various features for providing increased friction while maintaining a broad range of motion. For example, the segment 210 can include features that lead to a form fit by deforming one or both of two adjacent segments. A segment can be formed with a relatively hard material at the edge of the concave part of the segment and can be paired with a segment having a more deformable material at the convex part. A segment can include two different materials having different hardness. A segment can include cut-outs that increase the sharpness of the edge of the concave part of the segment. A segment can include ripples or small extrusions or other surface features in the concave and/or convex part of the segment, with the counterpart including a more deformable material.

The segment can include features that increase the friction coefficient with adjacent segments. For example, one or both counterpart mating surfaces of the segments can be bead-blasted or formed from a material with a high coefficient of friction.

The arm assembly 204 can include any of a variety of attachment features 208. The attachment feature 208 can define a central opening 252 through which an object, e.g., a surgical instrument, can be received. The attachment feature 208 can be positioned in a "closed" state, in which the attachment feature is locked to an object disposed therein to resist or prevent relative movement between the attachment feature and the object. The attachment feature 208 can be positioned in an "open" state, in which the attachment feature is not locked to an object disposed therein and in which the object can be removed from the attachment feature and/or moved in one or more degrees of freedom with respect to the attachment feature. The attachment feature 208 can have resilient properties. The attachment feature 208 can be configured to provide a pre-load or provisional friction fit to an object received therein prior to locking the attachment feature. The attachment features described herein can be used in any combination. All arms of the connector can include the same type of attachment feature, or one or more arms can include an attachment feature that differs from the attachment feature of one or more other arms.

Figure 4A:
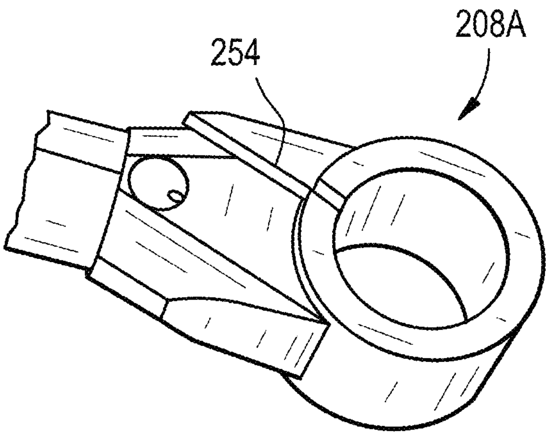
FIG. 4A is a perspective view of an attachment feature that can be used in the connectors herein.

FIG. 4A illustrates a ring clamp attachment feature 208A. The attachment feature 208A can include a generally cylindrical body with a slit 254 formed therein to allow radial expansion and/or radial contraction of the body. The wire 212 can extend across the slit 254 such that tension applied to the wire pulls opposed sidewalls of the slit towards one another to close the attachment feature 208A and clamp down on an object inserted therethrough. When tension is released from the wire 212, resilient material properties of the body can cause the opposed sidewalls of the slit 254 to move away from one another towards their resting state, releasing the attachment feature 208A from an object disposed therein. The wire 212 can extend through opposed proximal wings of the attachment feature 208A.

Figure 4B:
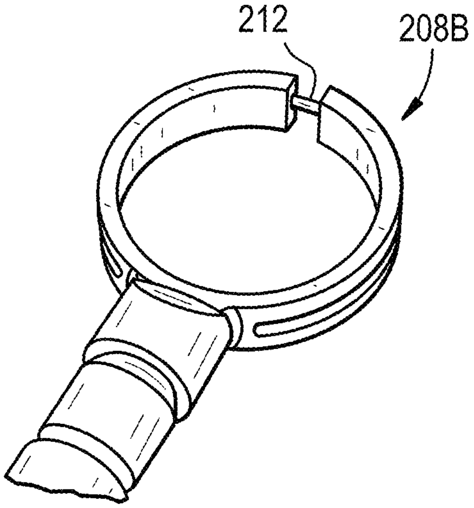
FIG. 4B is a perspective view of another attachment feature that can be used in the connectors herein.

FIG. 4B illustrates another ring clamp attachment feature 208B. The attachment feature 208B is substantially the same as that of FIG. 4A, except that the wire 212 extends around the circumference of the body.

Figure 4C:
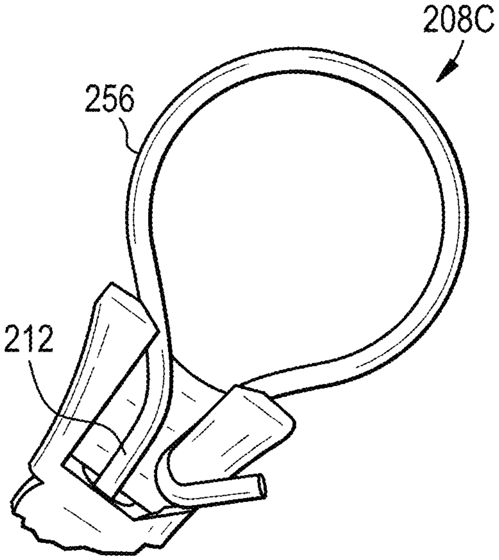
FIG. 4C is a perspective view of another attachment feature that can be used in the connectors herein.

FIG. 4C illustrates a lasso attachment feature 208C. The attachment feature 208C can include a loop of wire 256 through which an instrument or other object can be inserted. The loop of wire 256 can be an integral extension of the actuation wire 212 of the arm assembly 204 as shown. The free end of the wire 212 can be fixed at a termination of the attachment feature 208C, such that application of tension to the wire 212 can be effective to reduce the diameter of the loop 256, thereby clamping onto an object disposed therethrough.

Figure 4D:
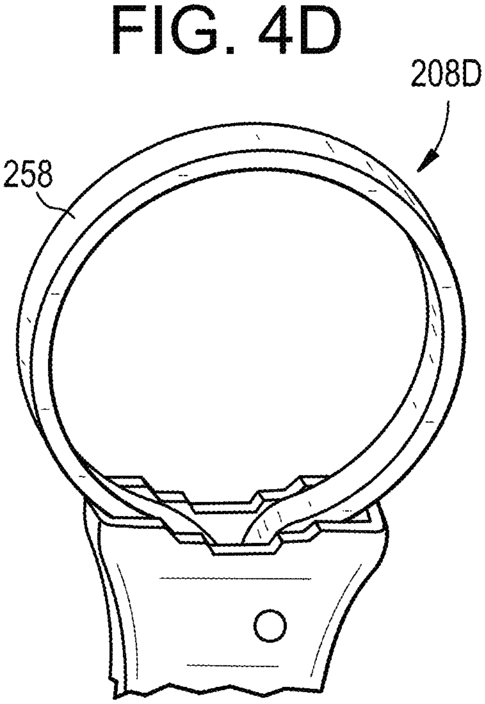
FIG. 4D is a perspective view of another attachment feature that can be used in the connectors herein.

FIG. 4D illustrates another lasso attachment feature 208D. The attachment feature 208D can include a looped member 258 having an increased aspect ratio. For example, the member 258 can have a height dimension that is greater than a radial thickness of the looped member. The looped member 258 can be a cylindrical tube with square cut ends. The looped member 258 can have a rectangular transverse cross-section. The looped member 258 can be an integral extension of the actuation wire 212 of the arm assembly 204, or can be attached thereto. Application of tension to the wire 212 can be effective to reduce the diameter of the looped member 258, thereby clamping onto an object disposed therethrough. Lasso attachment features can be more forgiving if the tension applied to the wire 212 is sub-optimal, if the instrument or object being clamped is non-circular, etc.

Figure 4E:
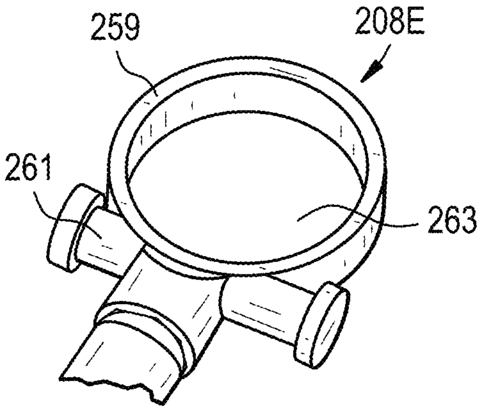
FIG. 4E is a perspective view of another attachment feature that can be used in the connectors herein.

FIG. 4E illustrates another attachment feature 208E. The attachment feature 208E can include a closed ring 259 and a locking bar 261. At least a portion of the bar 261 can intersect a central opening 263 of the ring 259. Movement of the bar 261 relative to the ring 259 can be effective to adjust the cross-sectional area of the central opening 263, e.g., by changing the degree to which the bar protrudes into the opening or by aligning or misaligning a cut-out formed in the bar with the opening. For example, rotating the bar 261 about its axis in a first direction can increase the cross-sectional area of the opening 263, e.g., to release an instrument or object inserted therethrough, and rotating the bar about its axis in a second, opposite direction can decrease the cross-sectional area of the opening, e.g., to clamp onto an instrument or object inserted therethrough. To achieve this function, the bar 261 can have a radial thickness that varies about its circumference. As another example, sliding the bar 261 along its axis in a first direction can increase the cross-sectional area of the opening 263, e.g., to release an instrument or object inserted therethrough, and sliding the bar along its axis in a second, opposite direction can decrease the cross-sectional area of the opening, e.g., to clamp onto an instrument or object inserted therethrough. To achieve this function, the bar 261 can have a radial thickness that varies along its length, or can have a ramp-shaped protrusion along a surface of the bar that protrudes into the central opening 263. For example, the bar 261 can be conically shaped with a relatively larger diameter at one end and a relatively smaller diameter at the other end with a tapered sidewall extending therebetween. The bar 261 can clamp to an instrument or object inserted through the opening 263 via self-retaining friction, via form-fit, or via a combination of both. The bar 261 can include a cut-out or recess that, when aligned with the opening 263, allows an instrument or object to be inserted through the opening. The instrument or object can include a cut-out or recess that receives the bar 261 after the bar is moved relative to the ring 259 to positively interlock the bar with the instrument or object and thereby retain the instrument or object within the attachment feature 208E. The instrument or object can include a plurality of incremental cut-outs, e.g., spaced along a length and/or circumference of the instrument or object.

Figure 4F:
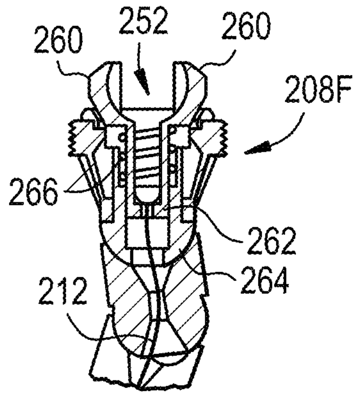
FIG. 4F is a sectional plan view of another attachment feature that can be used in the connectors herein.
Figure 4G:
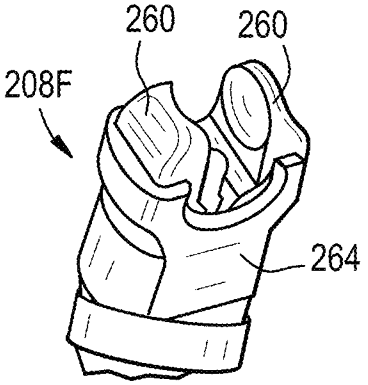
FIG. 4G is a perspective view of the attachment feature of FIG. 4F.

FIG. 4F-4G illustrate a jaw-type attachment feature 208F. The attachment feature 208F can include first and second opposed jaws 260 that define an instrument channel 252 therebetween in which an instrument can be disposed. The jaws 260 can be movable towards and away from one another. For example, the jaws 260 can be opposed cantilevered sections of a main jaw body 262 that are bendable towards and away from one another. Resilient material properties of the jaws 260 can be effective to bias the jaws apart from one another towards a resting position. The jaws 260 can be slidably mounted in an actuation sleeve 264. The actuation sleeve 264 and/or the jaws 260 can include ramp or wedge surfaces that contact and bear against one another. Accordingly, proximal translation of the jaws 260 relative to the sleeve 264 can cause the jaws to move towards one another, and distal translation of the jaws relative to the sleeve can cause the jaws to move apart from one another. The jaws 260 can be biased distally relative to the sleeve 264 by a spring 266. The sleeve 264 can be maintained at a fixed longitudinal position at the end of the arm 206, and the jaw body 262 can be coupled to the wire 212 of the arm assembly 204. In use, tension can be applied to the wire 212 to pull the jaw body 262 proximally relative to the sleeve 264, closing the jaws 260 together to clamp onto an instrument disposed therebetween. When tension on the wire is relaxed, the jaw body 262 can move distally relative to the sleeve 264 under the bias of the spring 266 and/or the resilient material properties of the jaws 260, opening the jaws apart from one another to release an instrument disposed therebetween. As shown in FIG. 4G, inner surfaces of the jaws 260 can include a depression having a geometry that corresponds to that of an object to be grasped by the jaws. For example, the jaws 260 can include a spherical depression for grasping onto a spherical attachment feature of an instrument, or a cylindrical depression for grasping onto a cylindrical access device or other instrument.

Figure 4H:
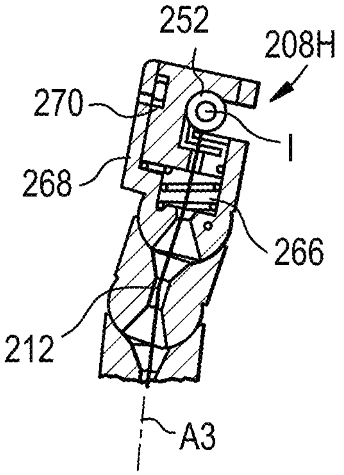
FIG. 4H is a sectional plan view of another attachment feature that can be used in the connectors herein.

FIG. 4H illustrates a side-loading jaw-type attachment feature 208H. The attachment feature 208H can include a sleeve 268 and a movable jaw 270 that collectively define an instrument channel or slot 252. The instrument channel 252 can be open in a lateral direction, such that an instrument 1 can be introduced into the channel by moving the instrument perpendicular or substantially perpendicular to the axis A3. When tension is applied to the wire 212, the movable jaw 270 can be pulled proximally to clamp an instrument between the jaw and the sleeve 268. When tension is released from the wire 212, the movable jaw 270 can be urged distally under the bias of a spring 266 to release an instrument from between the jaw and the sleeve 268.

Figure 4I:
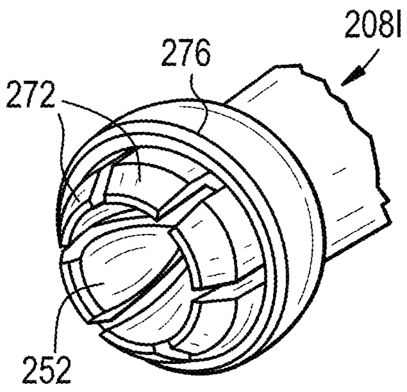
FIG. 4I is a perspective view of another attachment feature that can be used in the connectors herein.
Figure 4J:
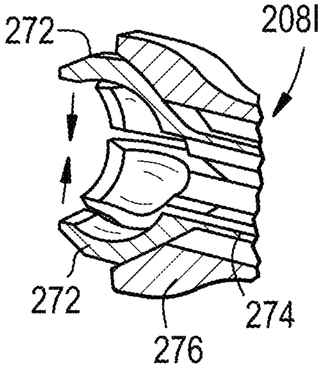
FIG. 4J is a sectional perspective view of the attachment feature of FIG. 4I.

FIGS. 4I-4J illustrate a spherical clamp attachment feature 208I. The attachment feature 208I can include a plurality of jaws 272 (e.g., six jaws as shown) that collectively define a cavity 252 in which an instrument or an attachment feature of an instrument can be disposed. The cavity 252 can be spherical and can be configured to receive a spherical instrument attachment feature. The jaws 272 can be movable towards and away from one another, e.g., to decrease or increase the diameter of a spherical cavity 252 defined therebetween. For example, the jaws 272 can be formed by cantilevered sections of a main jaw body 274 that are bendable towards and away from one another. Resilient material properties of the jaws 272 can be effective to bias the jaws apart from one another towards a resting position. The jaws 272 can be slidably mounted in an actuation sleeve or bowl 276. The actuation sleeve 276 can include ramp or wedge surfaces that contact and bear against corresponding ramp or wedge surfaces of the jaws 272. Accordingly, proximal translation of the jaws 272 relative to the sleeve 276 can cause the jaws to move towards one another, and distal translation of the jaws relative to the sleeve can cause the jaws to move apart from one another. The jaws 272 can be biased distally relative to the sleeve 276 by a spring. The sleeve 276 can be maintained at a fixed longitudinal position at the end of the arm 206, and the jaw body 274 can be coupled to the wire 212 of the arm assembly 204. In use, tension can be applied to the wire 212 to pull the jaw body 274 proximally relative to the sleeve 276, closing the jaws 272 together to clamp onto an instrument disposed therebetween. When tension on the wire 212 is relaxed, the jaw body 274 can move distally relative to the sleeve 276 under the bias of the spring and/or the resilient material properties of the jaws 272, opening the jaws apart from one another to release an instrument disposed therebetween.

The connectors disclosed herein can be biased towards an open or unlocked position, and user input force can be required to move the connector to a closed or locked position. Alternatively, the connectors disclosed herein can be biased towards a closed or locked position, and user input force can be required to move the connector to an open or unlocked position. In the handle assembly 202 described above, the pulley 218 is biased distally by the tension in the wire 212, such that the connector 200 is biased towards an open position.

Figure 5A:
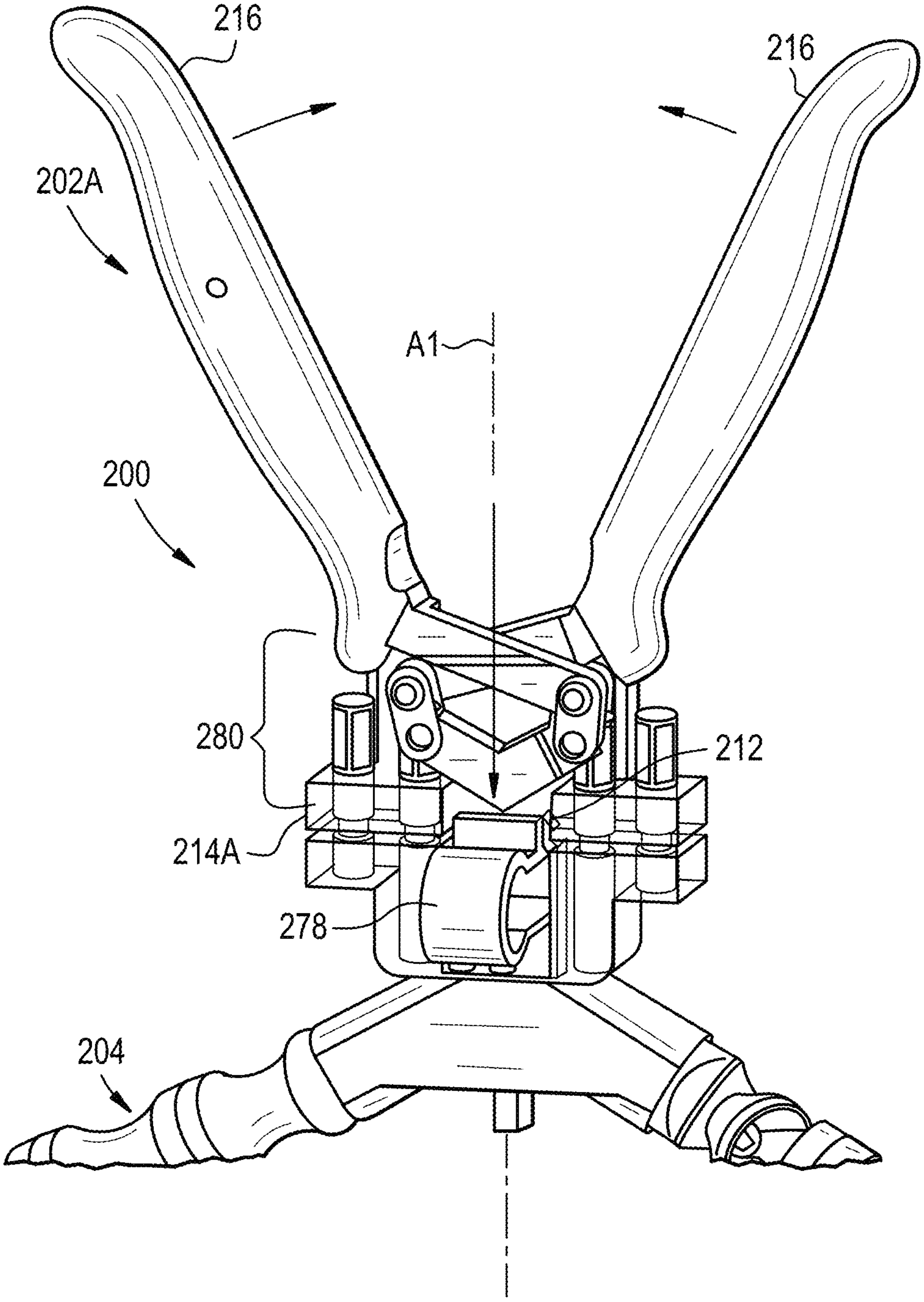
FIG. 5A is a perspective view of the connector of FIG. 2A, shown with an alternate handle assembly.

FIG. 5A illustrates an alternative handle assembly 202A that can be used with the connector 200 in which the connector is biased towards a closed position. The handle assembly 202A can include a spring element 278 mounted to the handle frame 214A. For example, the handle assembly 202A can include a C-spring, band, or plate spring 278 as shown. The wire 212 of the arm assembly 204 can extend around the spring element 278, such that the bias of the spring element exerts tension on the wire. When no user input force is applied to the handle levers 216, the arms of the C-spring 278 can tend to move apart from one another, pushing the wire 212 proximally relative to the handle frame 214 to apply tension to the wire. When the handle levers 216 are moved towards one another, the spring element 278 can be compressed to allow the wire 212 to move distally relative to the handle frame 214 to relax the tension on the wire. For example, the handle levers 216 can be pivotally coupled to a scissor linkage 280 that acts against the spring 278. Movement of the handle levers 216 towards one another as shown by the illustrated arrows can expand the scissor linkage 280 along the axis A1, compressing the spring 278 to release tension from the wire 212. Movement of the handle levers 216 away from one another can contract the scissor linkage 280 along the axis A1, allowing the spring 278 to expand and exert tension on the wire 212. The spring force of the spring 278 can be effective to bias the handles 216 apart from one another. In use, a user can easily unlock, reposition, and relock the connector 200 by squeezing the handle levers 216 together, articulating or moving the arms 206 of the connector 200 and/or the instruments or objects attached thereto, and then releasing the handle levers.

Figure 5B:
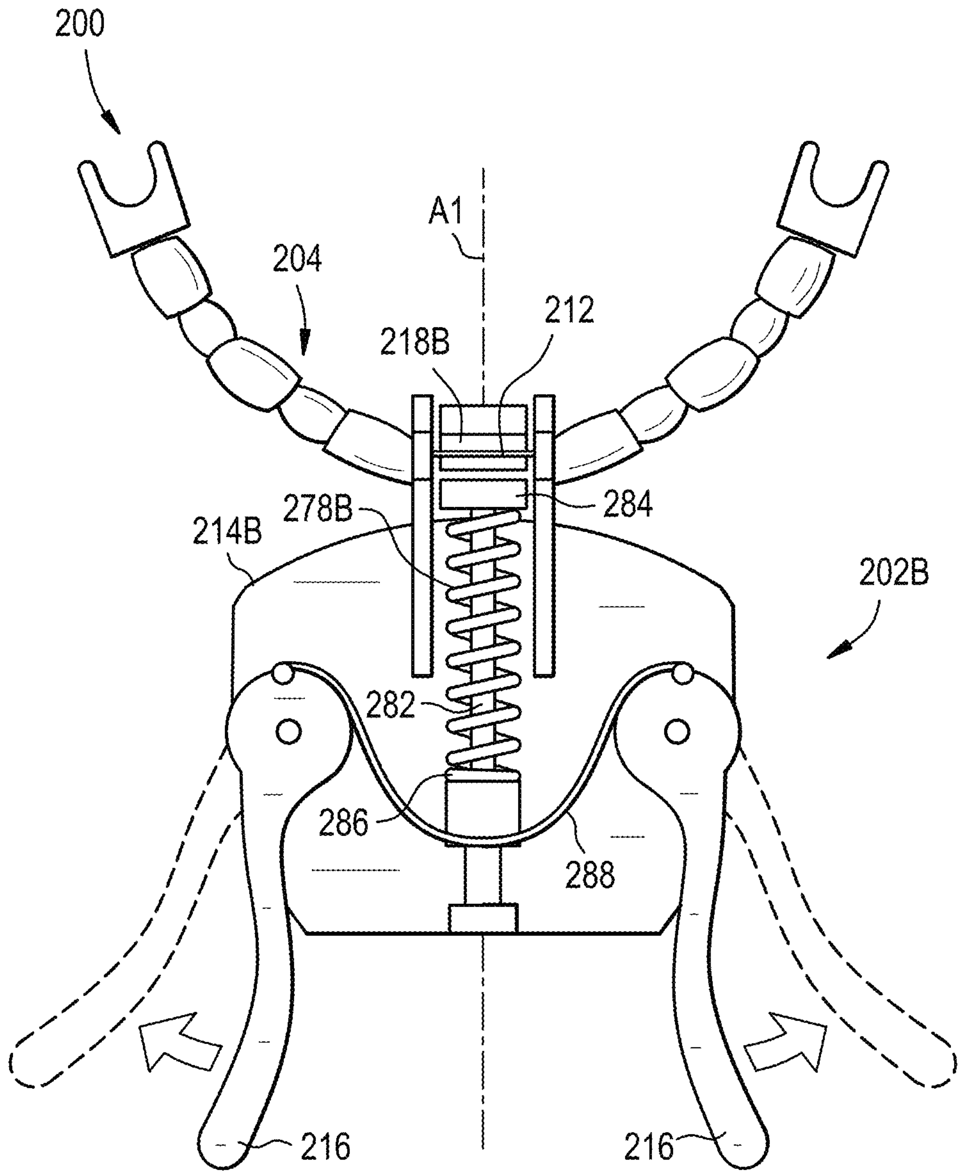
FIG. 5B is a perspective view of the connector of FIG. 2A, shown with another alternate handle assembly.

FIG. 5B illustrates another exemplary handle assembly 202B that can be used with the connector 200 in which the connector is biased towards a closed position. The handle assembly 202B can include a tension head 218B slidably mounted to the handle frame 214B. The tension head 218B can be movable along the axis A1 to increase or decrease the tension on the wire 212. Distal movement of the tension head 218B relative to the frame 214B can decrease the tension on the wire 212 and proximal movement of the tension head relative to the frame can increase the tension on the wire. The tension head 218B can include a shaft 282 that extends along the axis A1. A spring 278B can be disposed between a shoulder 286 formed on the shaft 282 and a spring seat 284 fixed to the handle frame 214B. The spring 278B can be effective to bias the shoulder 286 away from the spring seat 284, thereby biasing the tension head 218B in a proximal direction in which it applies increased tension to the wire 212. The handle assembly 202B can include first and second movable handle levers 216. Movement of the handle levers 216 towards one another can move the shoulder 286 distally, and by extension can move the shaft 282 and the tension head 218B distally to compress the spring 278B and relax the tension on the wire 212. Various mechanisms can be used to convert movement of the handles 216 towards one another into distal movement of the shoulder 286. For example, as shown, the handle levers 216 can be linked by a flexible tether 288 that is attached at its free ends to respective fixed points along a curved protrusion of the handle levers. The shoulder 286 can be supported at a midpoint of the tether 288. As the handle levers 216 move towards one another, the tether 288 can wind onto the curved portions of the handle levers, reducing the slack in the tether and moving the shoulder 286 distally. As the handle levers 216 move away from one another, the tether 288 can unwind from the curved portions of the handle levers, increasing the slack in the tether and allowing the shoulder 286 to move proximally under the bias of the spring 278B. In use, a user can easily unlock, reposition, and relock the connector 200 by squeezing the handle levers 216 together, articulating or moving the arms 206 of the connector 200 and/or the instruments or objects attached thereto, and then releasing the handle levers.

Figure 5C:
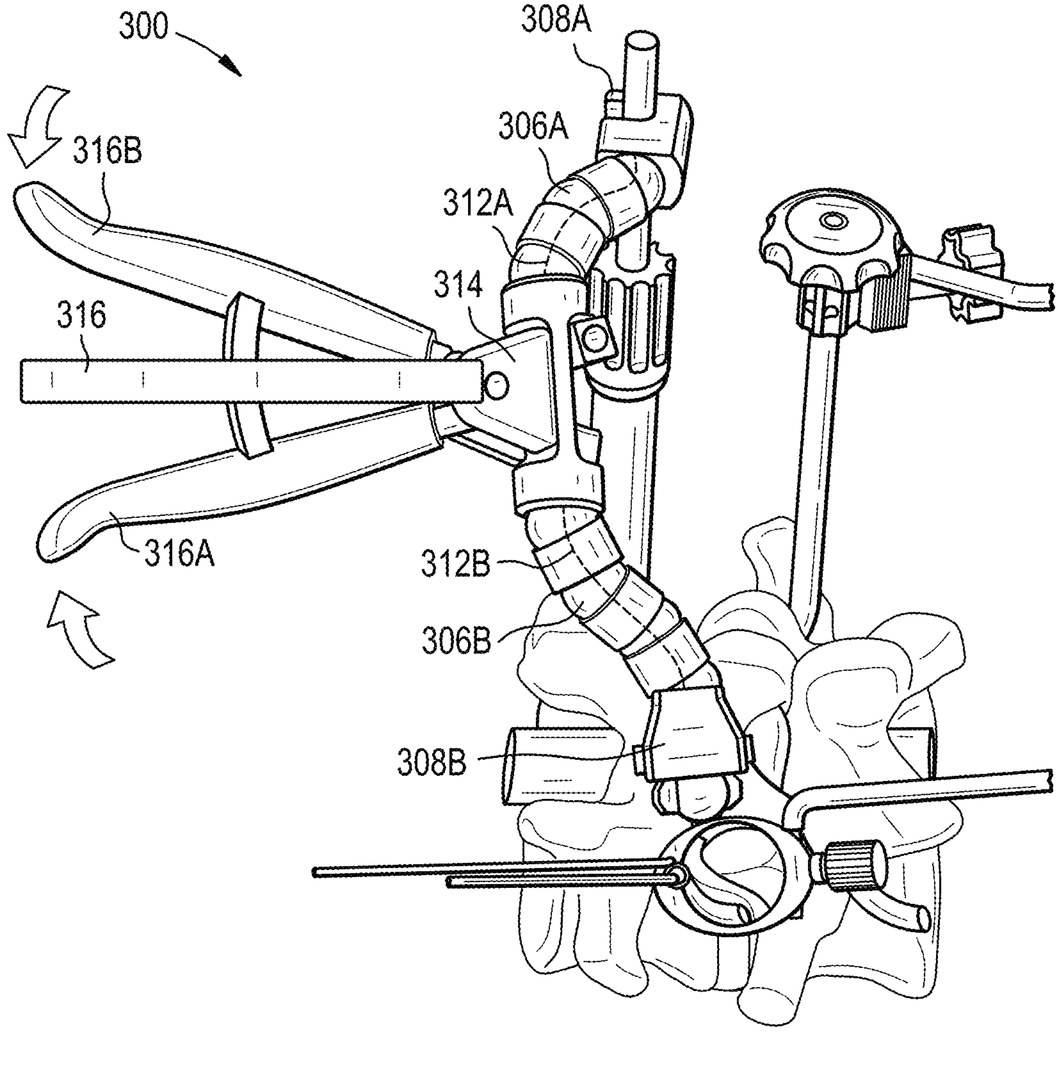
FIG. 5C is a perspective view of another connector.

The connector can include one or more arms that can be selectively locked or unlocked independently of one another. For example, FIG. 5C illustrates a connector 300 having first and second arms 306A, 306B coupled to a handle frame 314 having a fixed handle lever 316 and first and second movable handle levers 316A, 316B. Each arm 306A, 306B can include its own independent actuation wire 312A, 312B. In use, moving the first movable handle lever 316A towards the fixed handle lever 316 can apply tension to the first wire 312A to lock the first arm 306A and/or an attachment feature 308A thereof. In particular, rotation of the first handle lever 316A about a first pivot point can move the distal end of the first handle lever away from the proximal end of the first arm 306A to tension the first wire 312A. Movement of the second movable handle lever 316B towards the fixed handle lever 316 can apply tension to the second wire 312B to lock the second arm 306B and/or an attachment feature 308B thereof. In particular, rotation of the second handle lever 316B about a second pivot point can move the distal end of the second handle lever away from the proximal end of the second arm 306B to tension the second wire 312B. The first and second movable handle levers 316A, 316B can be independently movable, such that the first and second arms 306A, 306B can be locked or unlocked independently and/or such that the first and second attachment features 308A, 308B can be locked or unlocked independently. The fixed handle lever 316 can serve as a datum or foundation and the movable handle levers 316A, 316B can be independently-movable with respect thereto to allow for independent locking of each arm 306. The arms 306 and the attachment features 308 can include any of the features described herein. In other arrangements, movement of the handle levers can be effective to independently unlock the arms 306 and/or the attachment features 308.

Figure 5D:
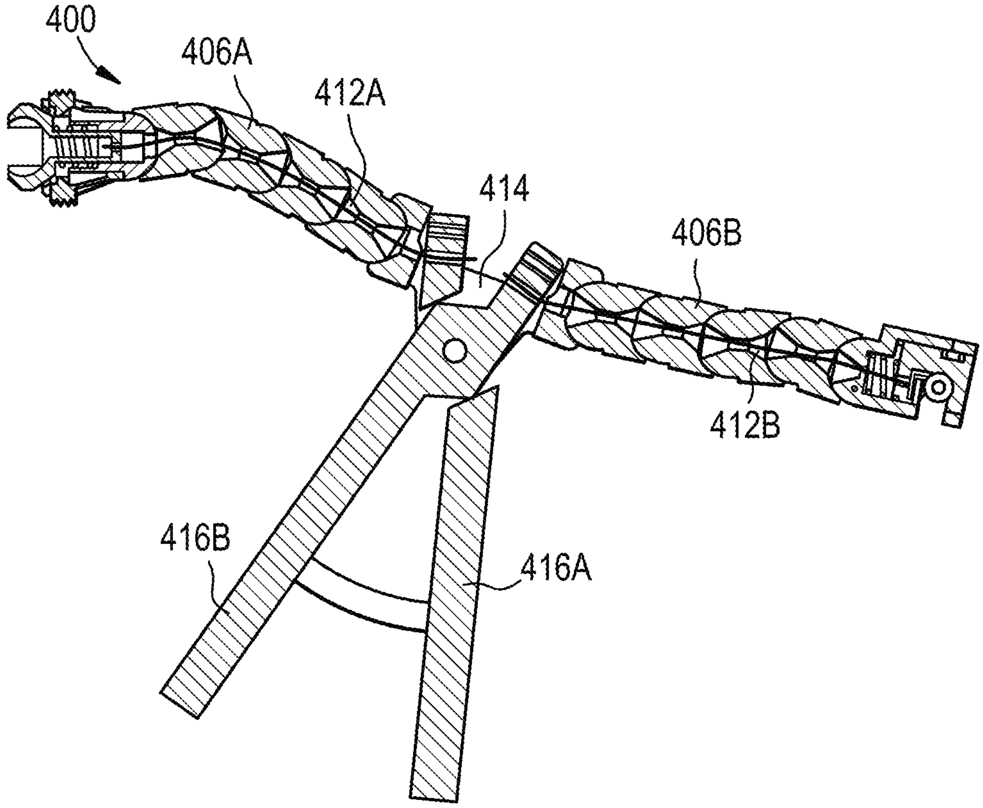
FIG. 5D is a sectional perspective view of another connector.

FIG. 5D illustrates a connector 400 similar to that of FIG. 5C except that the fixed handle lever is omitted. The connector 400 can include a handle frame 414 having first and second handle levers 416A, 416B coupled to respective first and second wires 412A, 412B of respective first and second arms 406A, 406B to selectively and/or independently apply tension thereto.

Figure 6A:
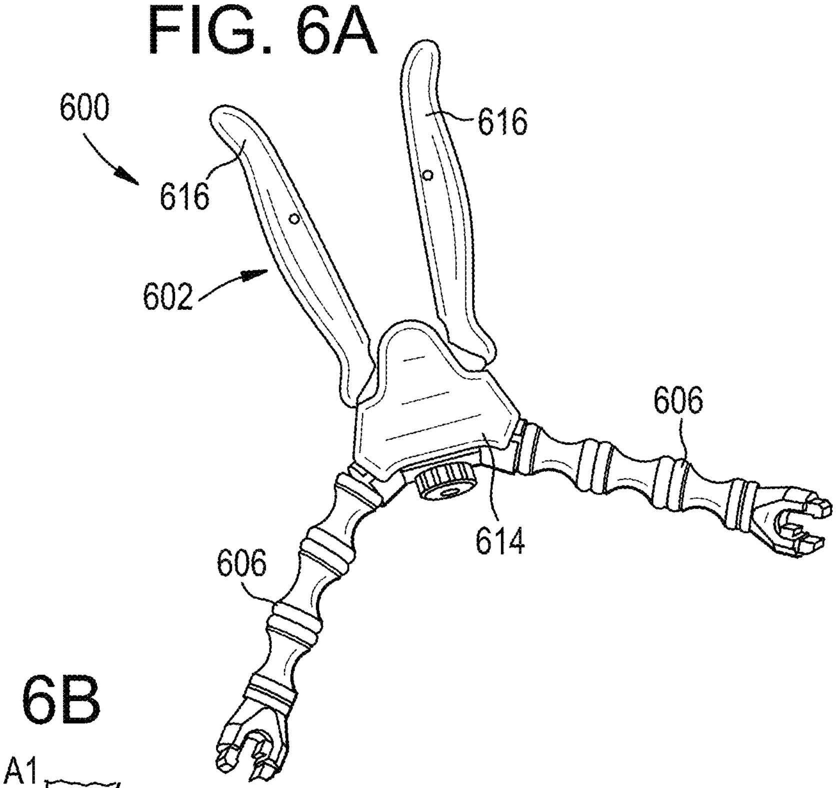
FIG. 6A is a perspective view of another connector.
Figure 6B:
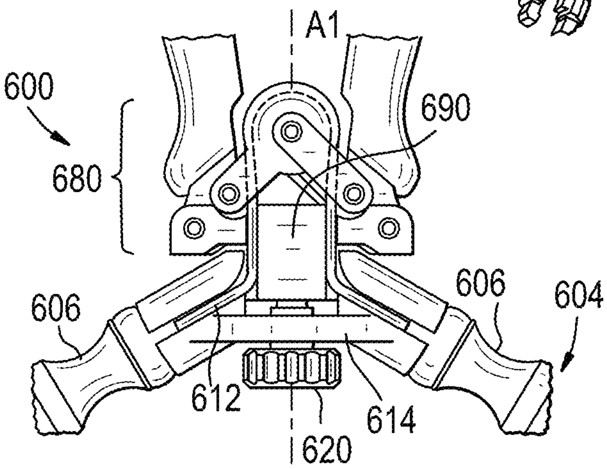
FIG. 6B is a perspective detail view of the connector of FIG. 6A in a locked configuration.
Figure 6C:
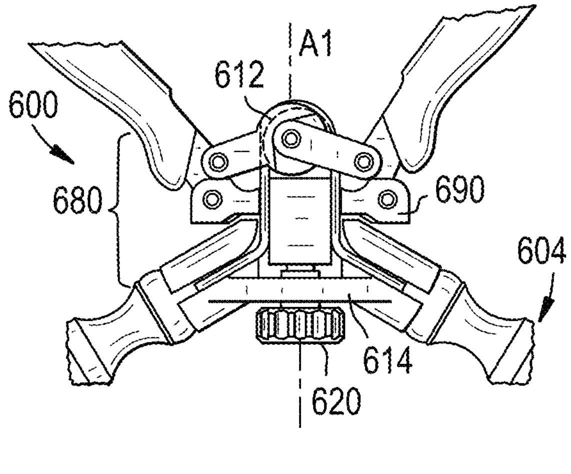
FIG. 6C is a perspective detail view of the connector of FIG. 6A in an unlocked configuration.

FIGS. 6A-6C illustrate another exemplary connector 600 that can be used to connect a first object to a second object. For example, the connector 600 can be used to connect first and second surgical instruments. By way of further example, the connector 600 can be used in the system 100 described above, e.g., to connect the access device 102 to the support or anchor 106. Except as indicated below and as will be readily appreciated by a person having ordinary skill in the art in view of the present disclosure, the structure and operation of the connector 600 is substantially the same as that of the connector 200 described above.

The connector 600 can include a tension pulley 618 mounted to the handle frame 614 by a scissor linkage 680. The connector 600 can include first and second movable handle levers 616. As shown in FIG. 6B, pivoting the handle levers 616 towards one another can expand the height of the scissor linkage 680 along the axis A1, moving the tension pulley 618 proximally to apply tension to the actuation wire 612 of the arm assembly 604. As shown in FIG. 6C, pivoting the handle levers 616 away from one another can reduce the height of the scissor linkage 680 along the axis A1, moving the tension pulley 618 distally to relax the tension on the actuation wire 612 of the arm assembly 604. The scissor linkage 680 can provide mechanical advantage, multiplying the user input force applied to the handle levers 616 to provide a relatively high locking force on the connector 600 in response to a relatively low input force.

The scissor linkage 680 can be mounted to the handle frame 614 by a slidable body 690 to which the handle levers 616 are pivotally coupled. The body 690 can be connected to the handle frame 614 by a threaded adjustment screw 620. Rotation of the screw 620 in a first direction can be effective to shift the body 690 proximally relative to the handle frame 614, increasing the preload tension applied by the handle assembly 602. Rotation of the screw 620 in a second, opposite direction can be effective to shift the body 690 distally relative to the handle frame 614, decreasing the preload tension applied by the handle assembly 602.

Figure 7A:
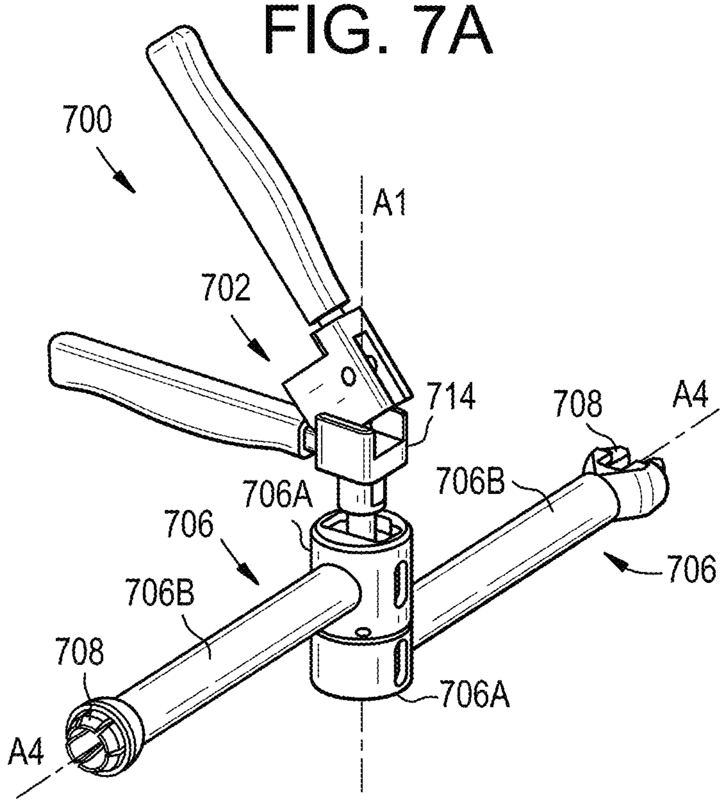
FIG. 7A is a perspective view of another connector, shown in an unlocked configuration.
Figure 7B:
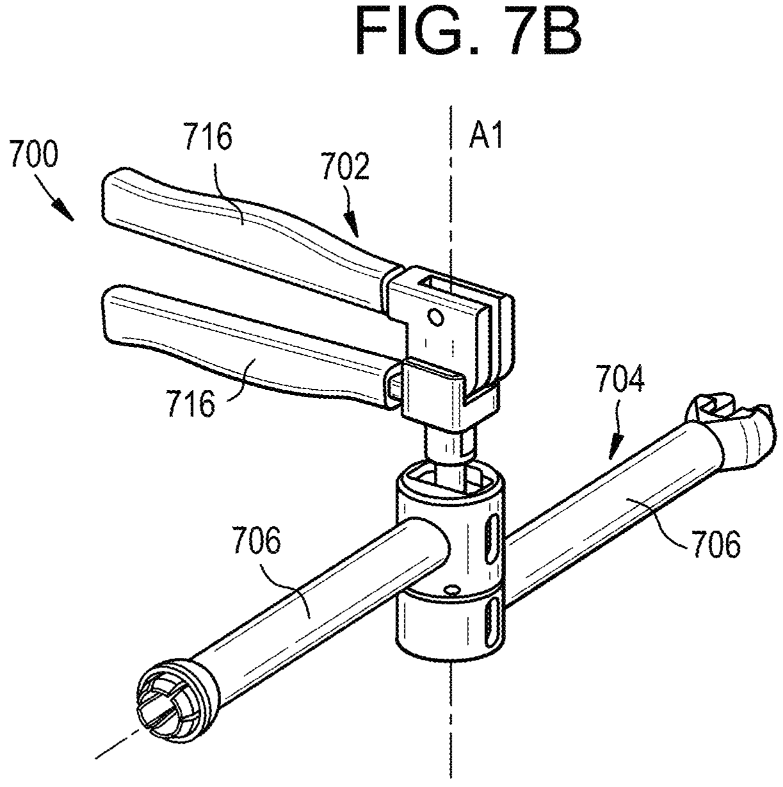
FIG. 7B is a perspective view of the connector of FIG. 7A in a locked configuration.
Figure 7C:
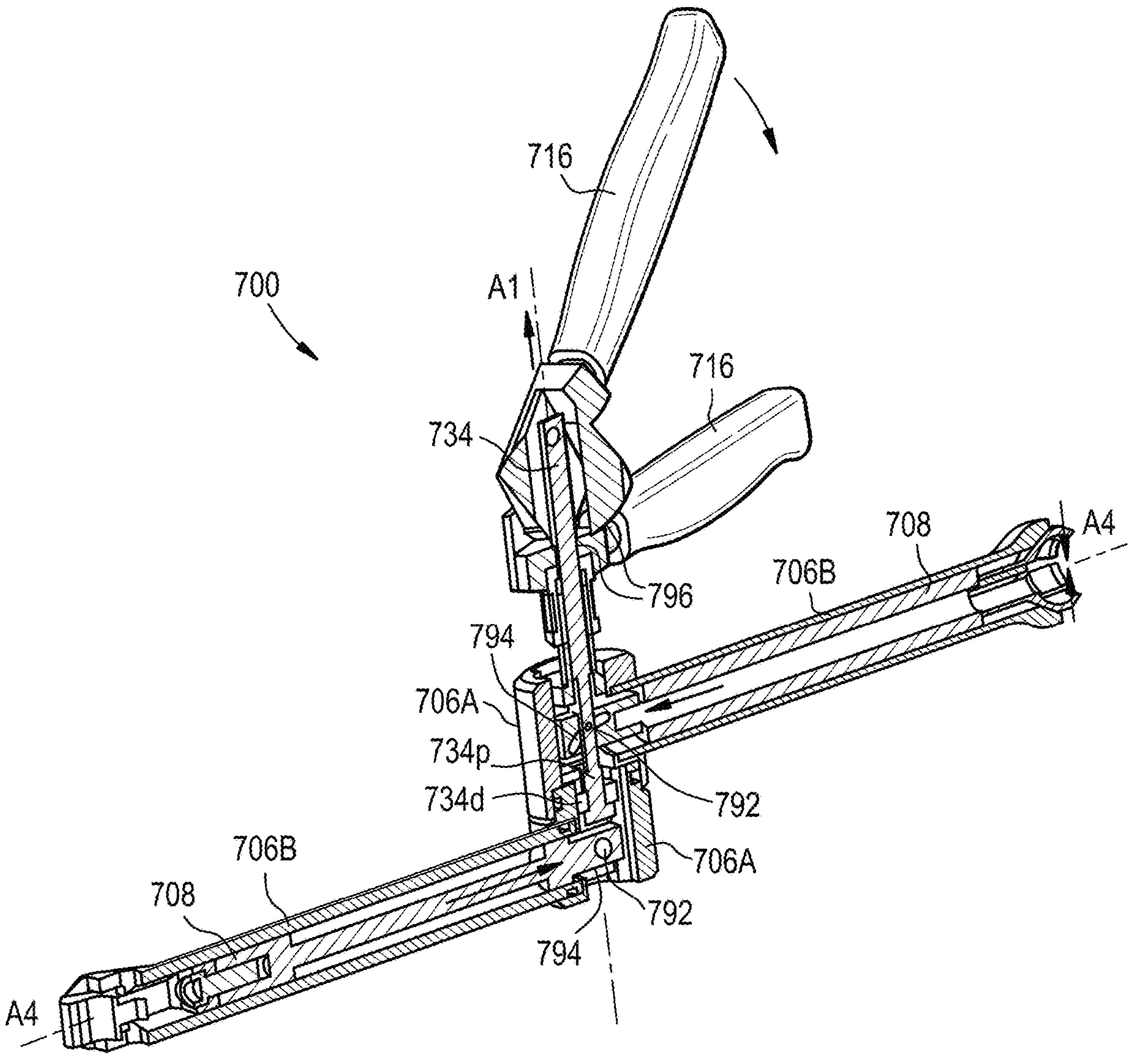
FIG. 7C is a sectional perspective view of the connector of FIG. 7A.

FIGS. 7A-7C illustrate another exemplary connector 700 that can be used to connect a first object to a second object. For example, the connector 700 can be used to connect first and second surgical instruments. By way of further example, the connector can be used in the system 100 described above, e.g., to connect the access device 102 to the support or anchor 106. Except as indicated below and as will be readily appreciated by a person having ordinary skill in the art in view of the present disclosure, the structure and operation of the connector 700 is substantially the same as that of the connector 200 described above.

The connector 700 can include one or more arms 706. The arms 706 can be rotatable relative to one another about the axis A1. The arms 706 can be rotatable relative to the handle frame 714 about the axis A1. Each arm 706 can include a first tubular portion 706A that extends along the axis A1 and a second tubular portion 706B that extends along a respective axis A4 that is perpendicular or obliquely angled relative to the axis A1. Each arm 706 can include a clamp 708 slidably mounted therein. An actuation shaft 734 can extend through the first tubular portions 706A of each arm and can connect the arms 706 to a handle assembly 702. The actuation shaft 734 can be coupled to the clamps 708 such that translation of the actuation shaft along the axis A1 causes translation of the clamps along their respective axes A4. In the illustrated arrangement, proximal translation of the actuation shaft 734 pulls the clamps 708 inward towards the axis A1, causing the outer tubular portions 706B of the arms 706 to compress the clamp 708 jaws inward onto an instrument or other object disposed therein. Proximal movement of the actuation shaft 734 can also pull the first tubular portions 706A of the arms 706 towards one another to lock relative rotation between the arms about the axis A1.

Distal translation of the actuation shaft 734 pushes the clamps 708 outward away from the axis A1, moving the clamp 708 jaws away from the outer tubular portions 706B of the arms 706, allowing the jaws to open to release from an instrument or other object disposed therein. Distal movement of the actuation shaft 734 can also allow the first tubular portions 706A of the arms 706 to move away from one another to restore free relative rotation between the arms about the axis A1.

The actuation shaft 734 can be coupled to the clamps 708 in various ways to achieve the above functionality. For example, the actuation shaft 734 can include pins 792 slidably mounted within respective sloped slots 794 formed in the clamps 708, or vice versa. The sloped slots 794 can extend at an oblique angle relative to the axis A1. The sloped slots 794 can extend at an oblique angle relative to the axes A4. The sloped slots 794 can convert translation of the actuation shaft 734 along the axis A1 into translation of the clamps 708 along their respective axes A4. By way of further example, one of the components can include a ramped tooth that projects radially outward to contact a ramped female surface of the other component.

The actuation shaft 734 can include multiple longitudinal segments that are linked to one another such that the segments cannot translate relative to one another along the axis A1 but are free to rotate relative to one another about the axis A1. This can allow the arms 706 to rotate relative to one another about the axis A1 while allowing the clamps 708 to be rotationally fixed relative to their respective segments of the actuation shaft 734 about the axis A1. For example, the actuation shaft can include a distal segment **734*d* that is rotatably coupled to a proximal segment 734*p*** as shown.

The handle assembly 702 can include one or more handle levers 716, e.g., a fixed handle lever and a movable handle lever as shown. The handle levers 716 can be configured to pivot relative to one another and to contact and bear against one another. The contact surfaces of the handle levers 716 can be shaped to provide a knee lever 796. The knee lever 796 can provide mechanical advantage, multiplying the user input force applied to the handle levers 716 to provide a relatively high locking force on the connector 700 in response to a relatively low input force. The knee lever 796 can also be self-stabilizing in the locked or fixed position, which can eliminate the need for additional locking or safety features.

In use, the arms 706 can be rotated relative to one another about the axis A1 to achieve the desired relative positioning of first and second objects disposed in the attachment features 708 of the first and second arms. The movable handle lever 716 can then be pivoted distally, pulling the actuation shaft 734 proximally to simultaneously lock (1) the attachment feature or end clamp of the first arm, (2) the attachment feature or end clamp of the second arm, and (3) the angular position of the first and second arms about the axis A1.

Figure 8A:
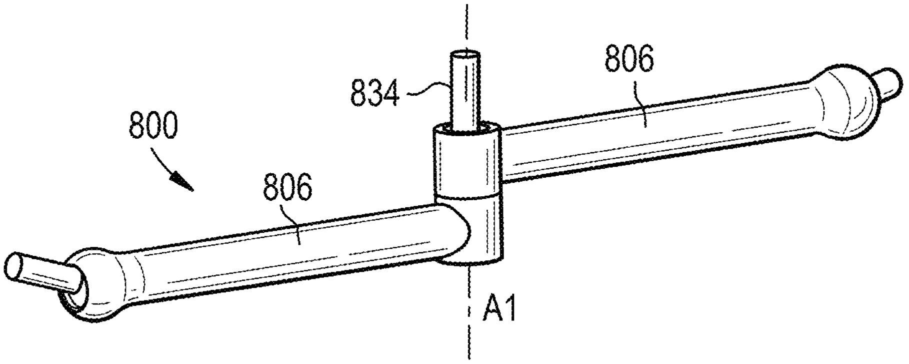
FIG. 8A is a perspective view of another connector.
Figure 8B:
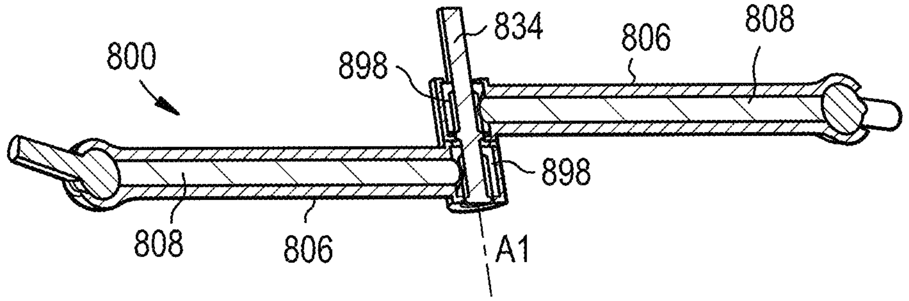
FIG. 8B is a sectional perspective view of the connector of FIG. 8A.
Figure 8C:
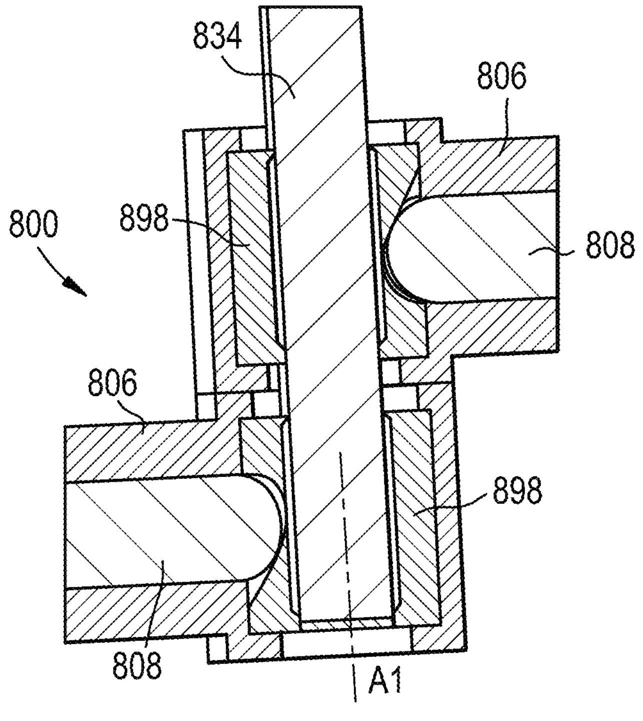
FIG. 8C is a sectional perspective detail view of the connector of FIG. 8A.

FIGS. 8A-8C illustrate another exemplary connector 800 that can be used to connect a first object to a second object. For example, the connector 800 can be used to connect first and second surgical instruments. By way of further example, the connector 800 can be used in the system 100 described above, e.g., to connect the access device 102 to the support or anchor 106. Except as indicated below and as will be readily appreciated by a person having ordinary skill in the art in view of the present disclosure, the structure and operation of the connector 800 is substantially the same as that of the connector 700 described above.

The connector 800 can include an actuation shaft 834 with ramped exterior surfaces. The ramped exterior surfaces can be formed directly on the actuation shaft 834, or on one or more bushings 898 through which the actuation shaft extends. The actuation shaft 834 can be rotatably fixed relative to the bushings 898, or can be configured to rotate relative to the bushings about the axis A1. Actuation of a handle assembly of the type described above can pull the actuation shaft 834 proximally to squeeze the bushings 898 towards one another along the axis A1. This can cause clamp rods 808 disposed in the arms 806 to be carried along ramped concave surfaces of the bushings 898, pushing the clamp rods radially outward away from the axis A1. This can urge the clamp rods 808 into firm engagement with a mating feature of an instrument or other object that is to be attached using the connector 800. For example, as shown, the clamp rods 808 can include a spherical concave surface at their free distal end that receives a convex spherical attachment feature of an instrument, and that bears against said attachment feature to lock a position and/or orientation of the instrument relative to the arm 806 when the clamp rod 808 is urged outward from the axis A1.

Figure 9A:
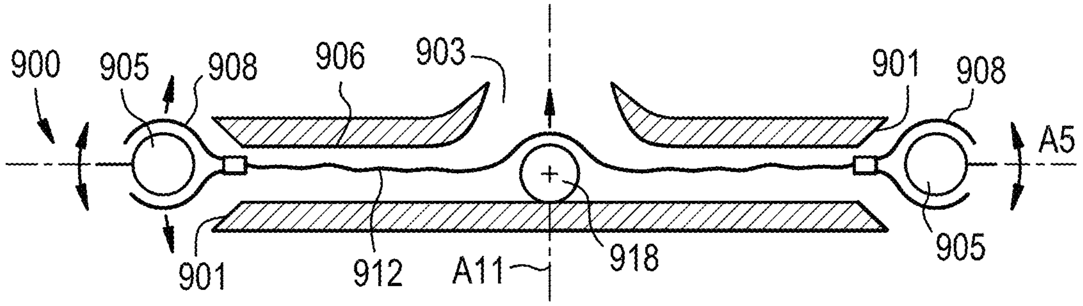
FIG. 9A is a sectional profile view of another connector, shown in an unlocked configuration.
Figure 9B:
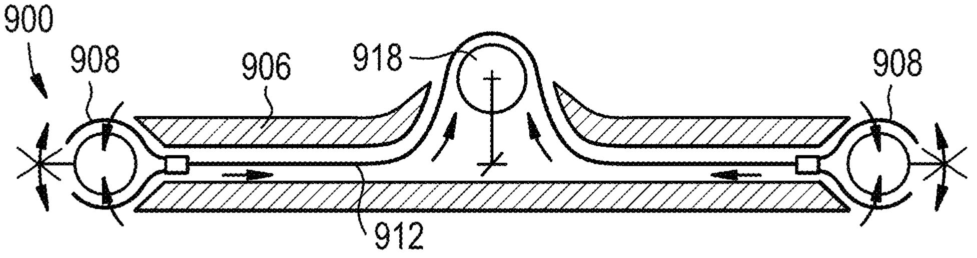
FIG. 9B is a sectional profile view of the connector of FIG. 9A, shown in a locked configuration.
Figure 9C:
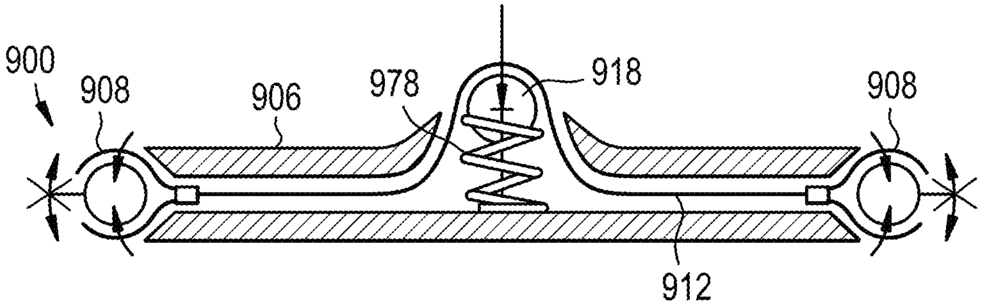
FIG. 9C is a sectional profile view of the connector of FIG. 9A, shown with a spring for biasing the connector towards the locked configuration.

FIGS. 9A-9C illustrate another exemplary connector 900 that can be used to connect a first object to a second object. For example, the connector 900 can be used to connect first and second surgical instruments. By way of further example, the connector 900 can be used in the system 100 described above, e.g., to connect the access device 102 to the support or anchor 106. Except as indicated below and as will be readily appreciated by a person having ordinary skill in the art in view of the present disclosure, the structure and operation of the connector 900 is substantially the same as that of the connector 200 described above.

The connector 900 can include a hollow rod 906 with wedged endplanes 901 and a sidewall opening 903 disposed therebetween. The rod 906 can include a central longitudinal axis A5. First and second elastic or resilient clamps 908 can be connected with a wire 912 that extends through the central lumen of the rod 906. The clamps 908 can include wedged shapes that match, or can otherwise engage with, the wedged endplanes 901 of the rod 906. The clamps 908 can include an inner shape configured to receive an attachment feature 905 of an implant, instrument, or other object therein. For example, the clamps 908 can include a spherical inner shape configured to receive a spherical instrument attachment feature 905. The wire 912 can bypass an actuation roller 918 that can be moved towards and away from the axis A5 along an axis A1 to adjust the tension in the wire 912. The connector 900 can include a handle assembly for moving the roller 918 towards or away from the axis A5. Any of the handle assemblies disclosed herein can be used.

As shown in FIG. 9B, moving the roller 918 away from the axis A5 can increase the tension applied to the wire 912. When this increased tension is applied to the cable 912, the clamps 908 can be pulled into the wedged endplanes 901 of the rod 906, thereby clamping down onto the attachment features 905 and fixing the position and/or orientation of the attachment features relative to the connector 900 and to one another.

As shown in FIG. 9C, the roller 918 can be biased away from the axis A5 by a spring 978, such that the resting position of the connector 900 is in a closed or locked state, and user input force is required to compress the spring and move the connector to the open or unlocked state.

Figure 9D:
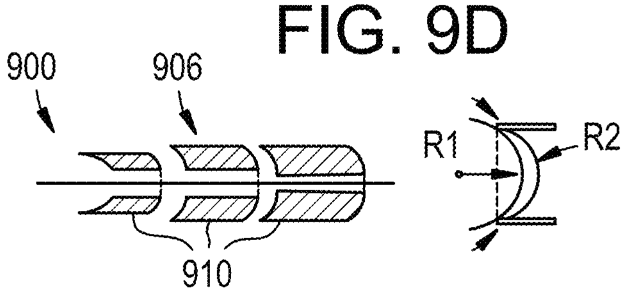
FIG. 9D is a sectional profile view of the connector of FIG. 9A, shown with a multi-segment arm.

The rod 906 can be rigid or flexible. The rod 906 can be a monolithic component or, as shown in FIG. 9D, can include a plurality of nested segments 910 as in the arm assemblies described above.

The connectors disclosed herein can be used in any of a variety of procedures, including surgical procedures of the type described herein.

For example, a first arm of the connector can be attached to a surgical access device and a second arm of the connector can be attached to a support. The surgical access device can be a cannula, a retractor, an extension tube of a bone anchor assembly, and so forth. The support can be an anatomical structure of the patient, a surgical table or an extension thereof, an implant or instrument attached to a patient (e.g., a pedicle post, a monoaxial screw head, an elongation of a monoaxial or polyaxial screw head, etc.), or various other structures. The connector can be effective to selectively maintain the access device in a fixed or substantially fixed position and/or orientation relative to the support. The connector can be unlocked to allow movement between the support and the access device in one or more degrees of freedom. The connector can be locked to prevent movement between the support and the access device in one or more degrees of freedom. The connector can rest in the unlocked state and a user input force can be required to transition the connector to the locked state. The connector can be configured to maintain itself in the locked state once positioned in the locked state, or can automatically return to the unlocked state. The connector can rest in the locked state and a user input force can be required to transition the connector to the unlocked state. The connector can be configured to maintain itself in the unlocked state once positioned in the unlocked state, or can automatically return to the locked state. The working tips of the structures that are attached using the connector can be positioned close together or far apart, with their respective positions and orientations varying as needed for a particular surgery.

Figure 10A:
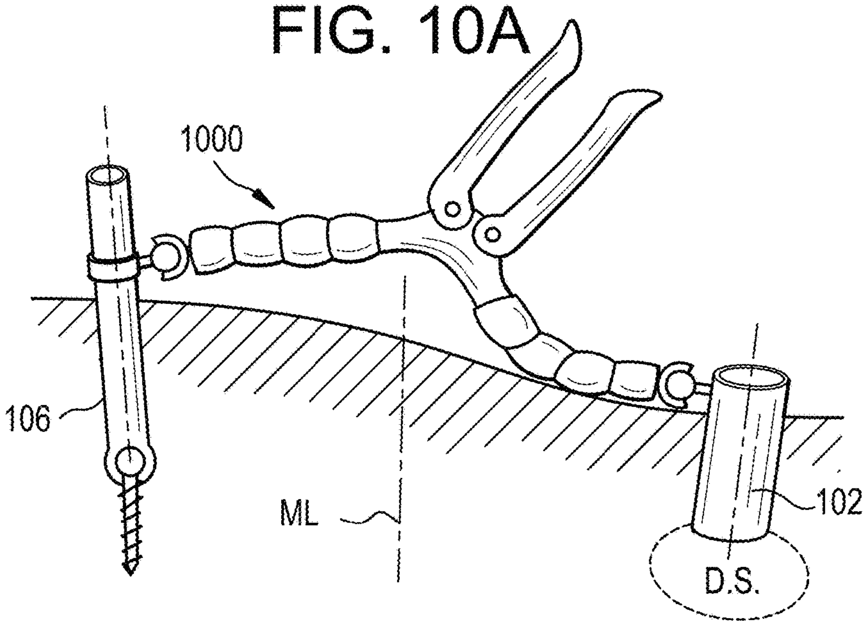
FIG. 10A is a schematic perspective view of a connector in use to connect a spinal access device to a contralateral support.

As shown in FIG. 10A, a connector 1000 of the type described herein can be used to attach a surgical access device 102 disposed on one side of a midline ML of a patient's spine to a pedicle-mounted extension post 106 disposed on an opposite, contralateral side of the midline. The surgical access device 102 can be positioned to provide access to a disc space DS of the patient's spine.

Figure 10B:
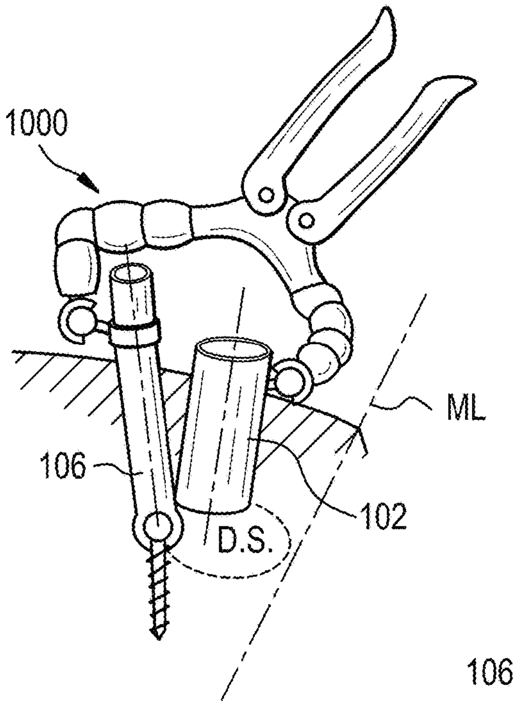
FIG. 10B is a schematic perspective view of a connector in use to connect a spinal access device to an ipsilateral support.

As shown in FIG. 10B, a connector 1000 of the type described herein can be used to attach a surgical access device 102 disposed on one side of a midline ML of a patient's spine to a pedicle-mounted extension post 106 disposed on the same, ipsilateral side of the midline. The surgical access device 102 can be positioned to provide access to a disc space DS of the patient's spine.

Use of contralateral or ipsilateral stabilization can be selected depending on the anatomical and pathologic situation. In some situations, ipsilateral support, e.g., at the same side of the patient where the surgical approach is performed, may be less invasive or provide more stability. In some situations, contralateral support may be desired, for example if a collapsed intervertebral disc leads to very narrow conditions resulting in interference between the access tube and the support if an ipsilateral arrangement is used.

Figure 10C:
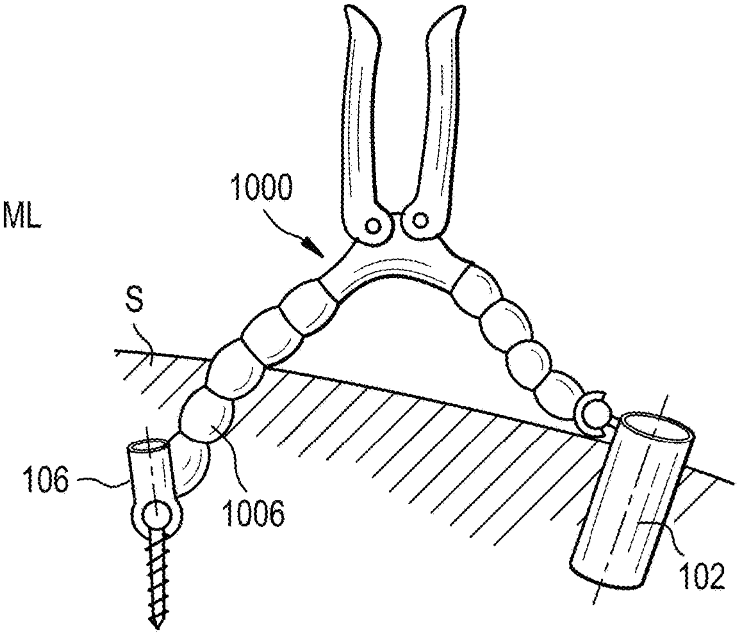
FIG. 10C is a schematic perspective view of a connector in use to connect a spinal access device to a support in which at least a portion of the connector is disposed within the patient.

When in use, the entire connector can be disposed external to the patient, e.g., as shown in FIGS. 10A-10B. Alternatively, at least a portion of the connector can be disposed internal to the patient. For example, as shown in FIG. 10C, at least a portion of one or more arms 1006 of the connector 1000 can be inserted through an incision formed in the patient's skin S to position said portion within the patient.

Connectors of the type described herein can be used in a wide array of surgical and non-surgical procedures.

Figure 10D:
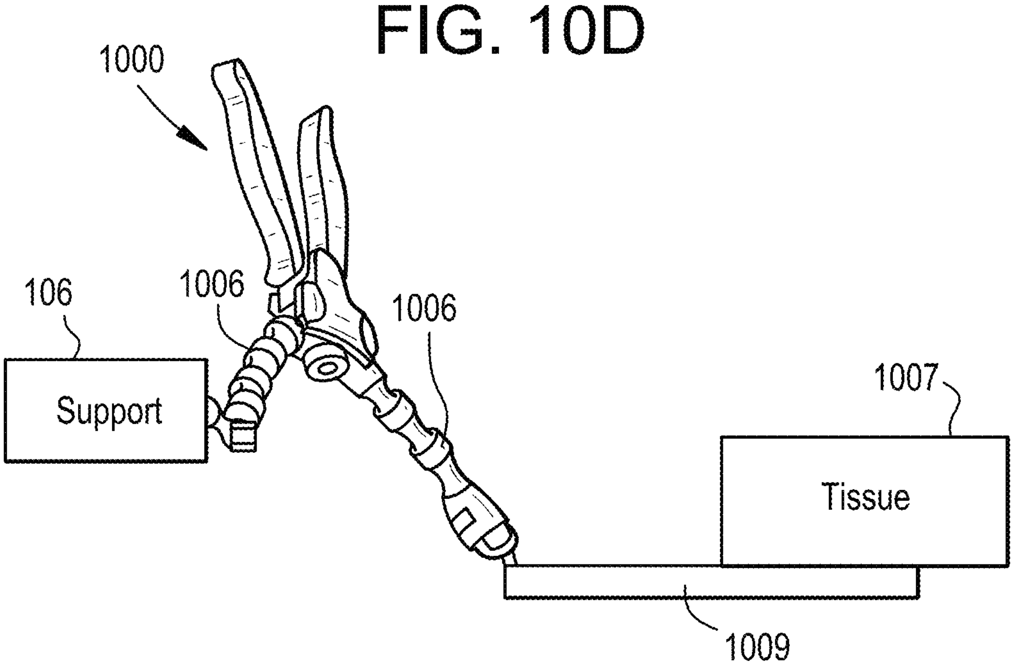
FIG. 10D is a schematic perspective view of a connector in use to support tissue.

For example, any of the connectors described herein can be used in plastic surgery. In a typical abdominoplasty procedure, the surgeon must hold or support tissue with one hand and cauterize or cut tissue with the other hand. The connector can be used to support the abdominal shelf, reducing or eliminating the need for the surgeon to support the shelf manually. As shown in FIG. 10D, one arm 1006 of the connector 1000 can be attached to a support 106, such as an operating room table. Another arm 1006 of the connector 1000 can be used to hold or support tissue 1007, either directly or by attaching the arm to a retractor, paddle, or other structure 1009 for holding or supporting tissue. The tissue can be the abdominal shelf. As the surgery progresses deeper beneath the abdominal shelf, the connector can be quickly unlocked, repositioned, and relocked to provide the tissue support desired by the surgeon.

In certain breast surgeries, an intra-mammary incision is formed and the breast is lifted to develop a pocket underneath. This can require the surgeon to hold or support tissue with one hand and cauterize or cut tissue with the other hand. The connector can be used to support the breast, reducing or eliminating the need for the surgeon to support the breast manually. Again, as shown in FIG. 10D, one arm 1006 of the connector 1000 can be attached to a support 106, such as an operating room table. Another arm 1006 of the connector 1000 can be used to hold or support tissue 1007, either directly or by attaching the arm to a retractor, paddle, or other structure 1009 for holding or supporting tissue. The tissue can be breast tissue. As the surgery progresses, the connector can be quickly unlocked, repositioned, and relocked to provide the tissue support desired by the surgeon.

Connectors of the type described herein can reduce user strain and fatigue in any procedure in which frequent retractor positioning is required, as the connector can be quickly and easily unlocked, repositioned, and relocked.

In an exemplary procedure, one or more arms of the connector can be attached to a light source, and the connector can be used to hold the light source in a position in which it illuminates a body cavity or other surgical site.

Figure 10E:
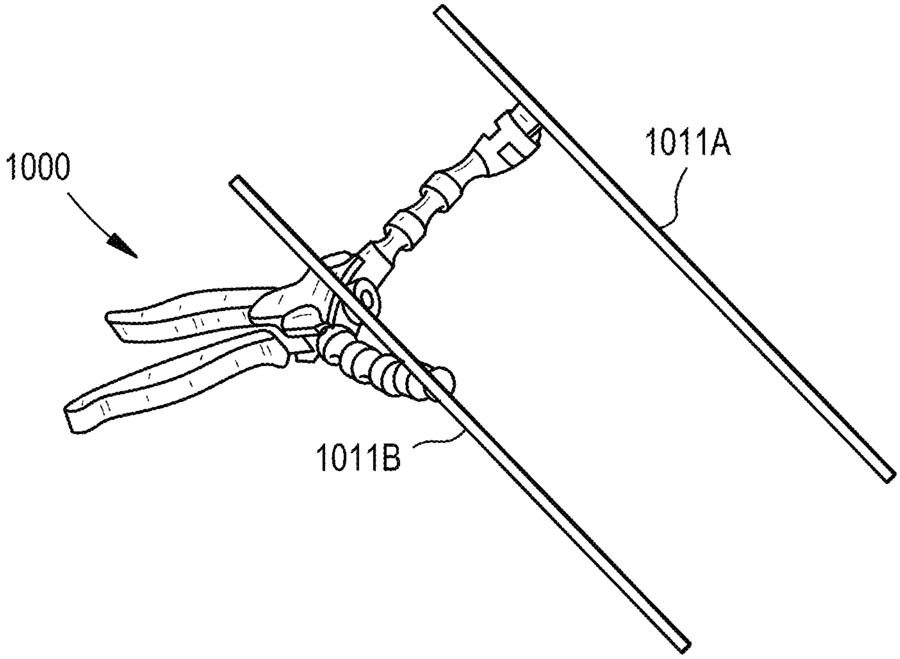
FIG. 10E is a schematic perspective view of a connector in use to automatically align two objects.

Any of the connectors described herein can be configured to automatically and consistently revert to a predetermined configuration, e.g., to automatically position first and second objects connected by the connector in a predetermined position and/or orientation with respect to one another. The connector can revert to the predetermined configuration when placed in the locked state. The geometry of the mating surfaces of the plurality of segments, and/or of the attachment features, can be selected to achieve the predetermined configuration when the connector is locked. For example, each segment can have counterpart mating surfaces that, when urged together as the wire is tensioned, cause the segments to move to a predetermined alignment. The predetermined configuration can be one in which the central longitudinal axes of two instruments 1011A, 1011B attached to the connector 1000 are placed in parallel, e.g., as shown in FIG. 10E. The instruments 1011A, 1011B can be first and second needles.

Connectors of the type described herein can be used in trans-anal surgery. For example, one arm of the connector can be coupled to a support such as an operating room table, and another arm of the connector can support an access device that is at least partially disposed in the rectum. One or more additional arms of the connector can be used to hold instruments or objects inserted through the access device, to hold a light source, or to hold any other object desired by the surgeon.

Figure 10F:
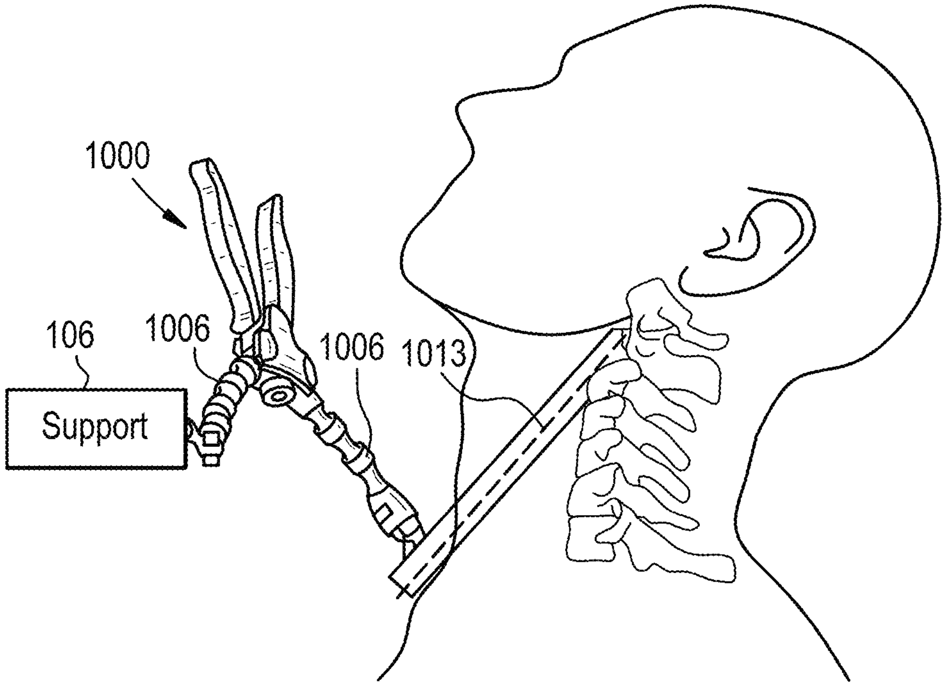
FIG. 10F is a schematic perspective view of a connector in use to support an access device for guiding placement of an odontoid screw.

Connectors of the type described herein can be used in procedures to place odontoid screws. For example, as shown in FIG. 10F, a first arm 1006 of the connector 1000 can be coupled to an access device 1013. The access device can be a cannula, retractor, drill guide, screw insertion sleeve, or the like. A second arm 1006 of the connector 1000 can be coupled to a support 106 of the type described herein, e.g., an anatomical support, pedicle screw, operating table, or the like. The connector 1000 can maintain the access device 1013 at a fixed trajectory. A lag screw, odontoid screw, or other bone anchor can be delivered through the access device 1013 to implant the bone anchor in the odontoid process, in the C2 vertebra, and/or in other bone structures, e.g., for reducing or addressing a fracture thereof.

Figure 10G:
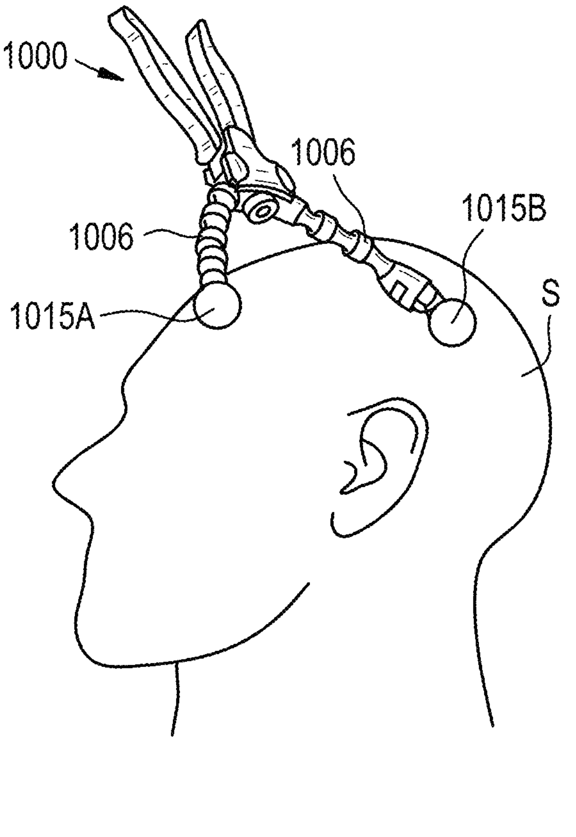
FIG. 10G is a schematic perspective view of a connector in use to connect first and second skull ports.

Connectors of the type described herein can be used to maintain access to a burr hole formed in a patient's skull. The connector can be used to maintain access to a plurality of burr holes, e.g., for evacuating epidural hematomas, subdural hematomas, hygromas, frontal bone, parietal bone, and so forth. For example, a first arm of the connector can be coupled to a retractor or skull port over a first burr hole in the patient's skull and a second arm of the connector can be coupled to a support of the type described herein, e.g., the patient's skull, the patient's skin, another retractor or port, etc. As another example, as shown in FIG. 10G, a first arm 1006 of the connector 1000 can be coupled to an access device 1015A (e.g., a cannula or skull port) over a first burr hole formed in a patient's skull S. A second arm 1006 of the connector 1000 can be coupled to an access device 1015B (e.g., a cannula or skull port) over a second burr hole. The connector can include only two arms, such that the connector is attached only to the two retractors/ports and not to an external support. As yet another example, a first arm of the connector can be coupled to a retractor or skull port over a first burr hole, a second arm of the connector can be coupled to a retractor or skull port over a second burr hole, and third arm of the connector can be coupled to a support of the type described herein.

In the examples above, the first skull port can be used to deliver material to the patient and the second skull port can be used to aspirate material from the patient. For example, saline or other flushing material can be delivered through the first port while a hematoma or other material is aspirated through the second port.

Figure 10H:
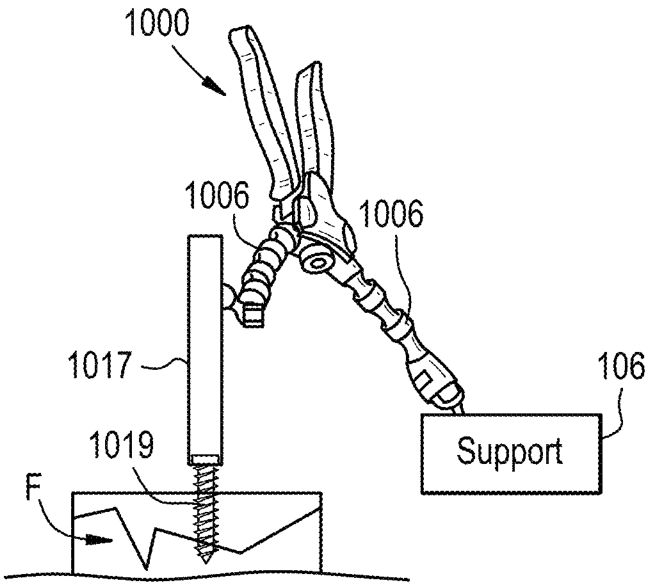
FIG. 10H is a schematic perspective view of a connector in use to support an access device for guiding a lag screw during repair of a bone fracture.

Connectors of the type described herein can be used in orthopedic or trauma surgery, for example in reducing, reconstructing, or otherwise addressing bone fractures. In an exemplary fracture repair procedure, a lag screw can be placed to reduce one or more bone fragments and hold them in a natural or desired position for healing. As shown in FIG. 10H, a first arm 1006 of the connector 1000 can be coupled to an access device 1017. The access device 1017 can be a cannula, retractor, drill guide, screw insertion sleeve, or the like. The access device 1017 can be used to guide insertion of a lag screw or nail 1019 into a bone fracture F. A second arm 1006 of the connector 1000 can be coupled to a support 106 of the type described herein, e.g., an external frame, an anatomical support, an operating table, a Jackson table, another lag screw or nail, a bone plate, or the like. The support 106 can be a lag screw or nail that has already been placed, e.g., to address the same fracture for which the current screw or nail is intended or to address a fracture proximate thereto. The support 106 can be a bone plate at least partially implanted in the patient, e.g., to address the same fracture for which the current screw or nail is intended or to address a fracture proximate thereto. The support 106 can be a bone plate through which the current screw or nail is to be placed.

The connector arm that holds the access device 1017 can be placed with intelligence. For example, the arm can be placed under robotic control, using a surgical navigation system, or using computer-assisted surgical techniques to align the access device with a predetermined insertion point and at a predetermined trajectory. The predetermined trajectory can be one in which the screw to be inserted crosses the fracture line at an optimal vector for reducing the fracture. As another example, intelligence can exist between multiple arms of the connector. The connector arms can be equipped with MEMS sensors, navigation beacons, or other components to determine their relative position and/or orientation. The access device can be placed using preoperative or intraoperative planning. The access device can be placed using 3D surgical navigation, ultrasound, fluoroscopy, etc. The access device can be coupled to an electronic display that shows a virtual reality (VR) and/or augmented reality (AR) image of the fracture line and alignment of the access device with the fracture line. The user can then manipulate the connector until the desired alignment is reached, e.g., as confirmed via the display, lock the connector in place, and then insert the screw or nail.

Connectors of the type described herein can be used in tibial plateau fracture reduction. One arm of the connector can attach to a tibial bone plate and another arm of the connector can attach to and align a working channel, guide sleeve, or other access device over the opening of the plate through which a screw is to be inserted. Connectors of the type described herein can be used in navicular or scaphoid fracture reduction. Connectors of the type described herein can be used for mid-shaft fractures with multiple butterfly fragments.

When used in applying a fixation construct to a patient, connectors of the type described herein can be attached to part of the final fixation construct, e.g., when adding a screw or bone anchor in or around the construct.

Figure 10I:
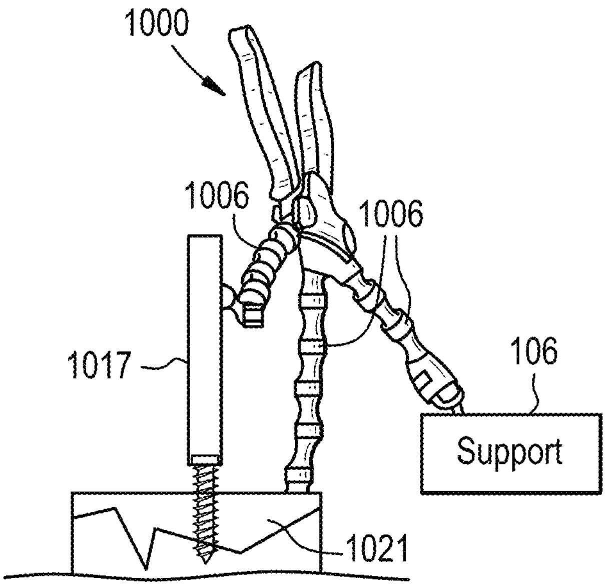
FIG. 10I is a schematic perspective view of a connector in use to support an access device and a bone fragment during repair of a bone fracture.

Connectors of the type described herein can be used to hold a bone fragment in place while inserting a screw or nail to repair a fracture. For example, as shown in FIG. 10I, one arm 1006 of the connector 1000 can be used to hold a bone fragment 1021, one arm 1006 can be used to hold an access device 1017, and one arm 1006 can be attached to a support 106. As another example, one arm of the connector can be used to hold an access device, which in turn can be used to hold a bone fragment in place, and another arm of the connector can be attached to a support. The access device can be shaped to facilitate bone retention, for example by having a distal end that is concave, convex, a negative of the bone surface, coated with an adhesive, or that includes teeth or other gripping features for holding the bone fragment in place. An exemplary method of treating a bone fracture can include: unlocking the connector; attaching a bone fragment to an arm of the connector; positioning the fragment in a desired location; aligning a guide channel attached to another arm of the connector with a fracture plane, screw insertion point, or other location; locking the connector; and inserting a screw or nail through the guide channel to secure the fragment in the desired location.

Use of a connector of the type described herein in fracture repair procedures can provide advantages over existing techniques that largely rely on eyeballing, freehand approximation, or extensive use of fluoroscopy.

Figure 10J:
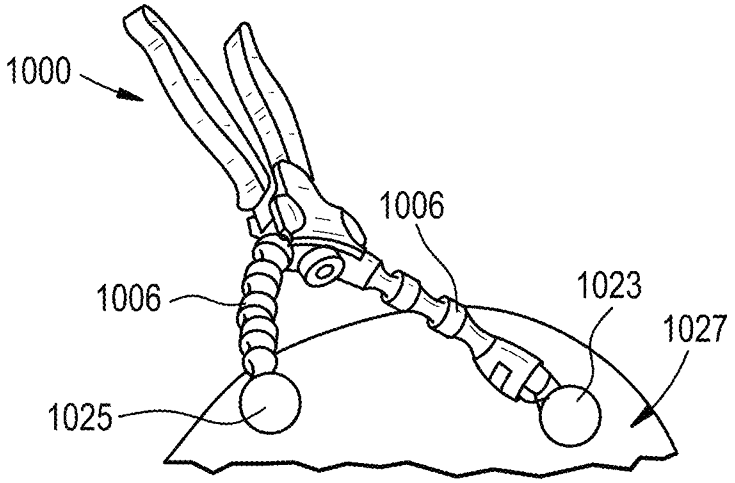
FIG. 10J is a schematic perspective view of a connector in use to maintain a position between a visualization device and a surgical instrument.

Connectors of the type described herein can be used in minimally-invasive surgery. For example, a connector can be used to maintain alignment between a scope or visualization device and a surgical instrument. In arthroscopic joint surgery, e.g., of the knee, an arthroscope can be inserted through a first skin portal and a surgical instrument, e.g., for cutting, shaving, or manipulating tissue, can be inserted through a second skin portal. Typically, the user wishes to align the field of view of the arthroscope with the distal end or working portion of the instrument. If the user turns away momentarily to attend to other surgical tasks, the arthroscope and/or the instrument can move, causing the user to lose visualization of the instrument. The user must then go through the cumbersome task of realigning the arthroscope with the instrument to restore visualization. This can be avoided using connectors of the type herein. For example, as shown in FIG. 10J, one arm 1006 of a connector 1000 can be attached to an arthroscope or other visualization device 1023. The visualization device can be inserted through a first skin portal. The visualization device can be inserted into a joint of a patient, e.g., into a knee joint 1027 as shown. Another arm 1006 of the connector 1000 can be attached to a surgical instrument 1025, or to a guide sleeve or access device through which a surgical instrument is inserted into the patient. The guide sleeve can be inserted through a second skin portal that is discrete from the first skin portal. The connector 1000 can be locked to maintain a fixed position and/or orientation between the guide sleeve or instrument 1025 and the visualization device 1023. For example, the arms of the connector can be locked such that the distal ends of two objects held thereby are focused on the same area or substantially the same area. Accordingly, the user can release one or both objects and attend to other tasks without losing visualization of the instrument.

Figure 10K:
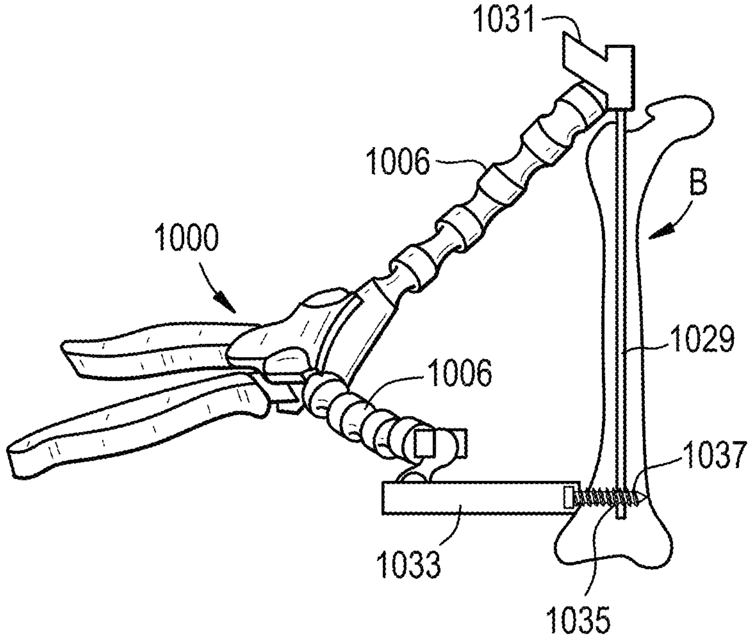
FIG. 10K is a schematic perspective view of a connector in use to support an access device for guiding placement of a locking screw in an intramedullary device.

Connectors of the type described herein can be used in placement of intramedullary (IM) devices, rods, or nails, e.g., to treat long bone fractures. For example, a connector can be used to align a locking screw with a locking hole formed in the IM device. As shown in FIG. 10K, one arm 1006 of a connector 1000 can be attached to the IM rod 1029 or to an IM rod inserter 1031 mounted thereto while the rod 1029 is inserted into a bone B. Another arm 1006 of the connector 1000 can be attached to an access device 1033. The access device 1033 can be a cannula, retractor, drill guide, screw insertion sleeve, or the like. The arms 1006 of the connector 1000 can be manipulated to align the access device 1033 with a locking hole 1035 of the IM rod 1029. The connector 1000 can then be locked in position and the access device 1033 can be used to guide drilling of the bone B and subsequent insertion of a locking screw 1037 through the locking hole 1035 of the IM rod 1029. Use of the connector to maintain the access device at a fixed position and/or orientation relative to the IM rod can reduce or eliminate the need for fluoroscopy to confirm that the access device has not drifted. For example, the user can switch from a drill to a screw driver without having to re-check the position of the cannula under fluoroscopy, potentially reducing radiation exposure to the patient. Instead of attaching the connector to the IM rod or inserter, or in addition thereto, one arm of the connector can be clamped or otherwise attached to bone, or can be attached to a support of the type described herein.

Figure 11A:
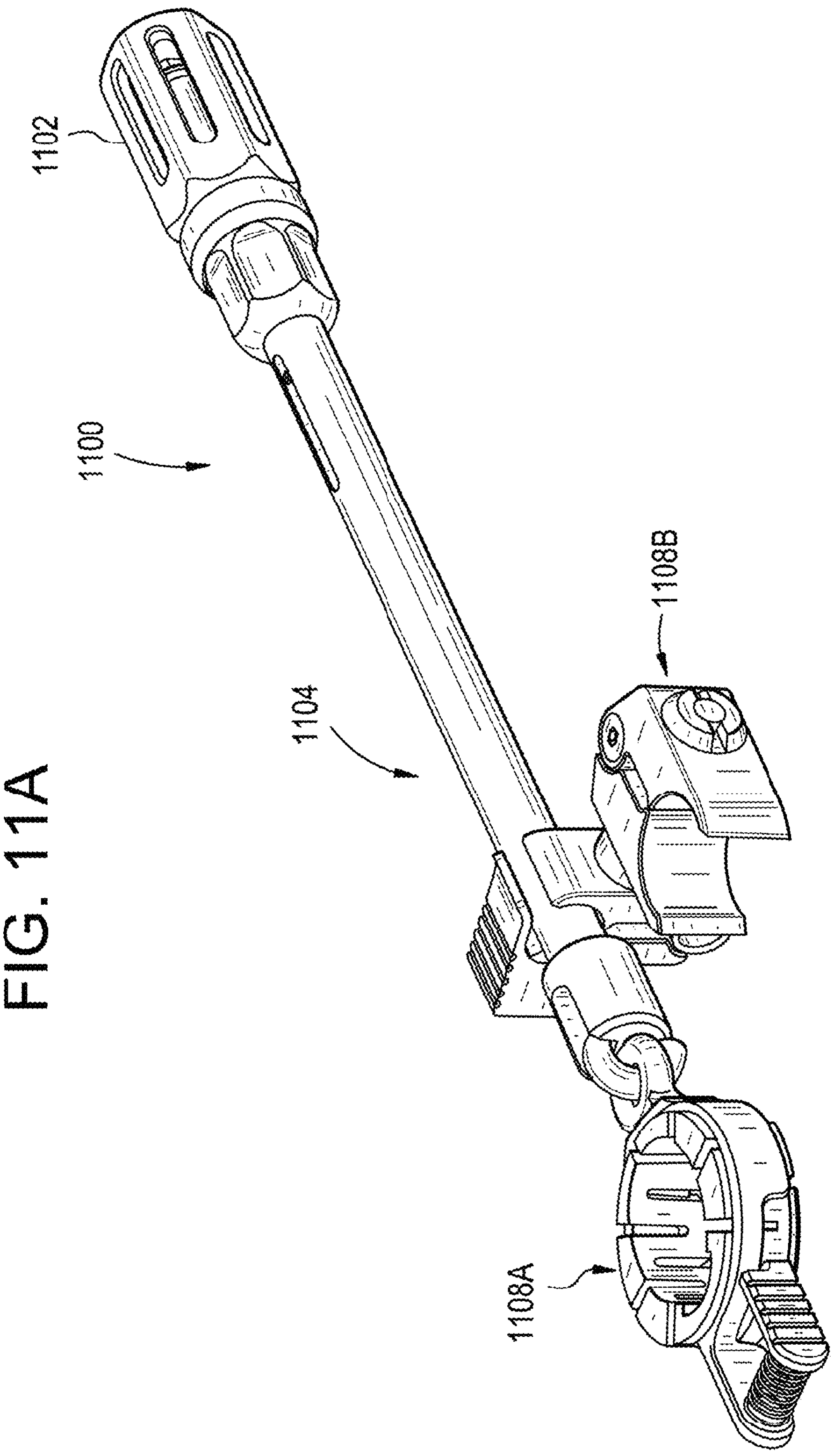
FIG. 11A is a perspective view of another embodiment of a connector.

FIGS. 11A-11E illustrate another exemplary embodiment of a connector assembly that can be used to connect a first object to a second object. For example, the connector assembly 1100 can be used in a similar fashion to the system 100 described above, e.g., to connect a surgical access device to a support. By way of further example, the connector assembly 1100 may be used to anchor a surgical access device and stabilize the surgical access device to a support, anchor, or other object. The support structure may include a pedicle post, bone anchor screw extension tabs, a part of a patient's anatomy, for example a patient's skin, an operating table etc. FIG. 11A illustrates an exemplary connector 1100. The connector 1100 can include a handle 1102, an arm assembly 1104, and at least one attachment feature 1108. In one embodiment, a first attachment feature can engage a surgical access device. The first attachment feature can preferably be a double ring clamp 1108A. In one embodiment, a second attachment feature can engage a support. The second attachment feature can preferably be a screw clamp assembly 1108B.

Figures 11B, 11C:
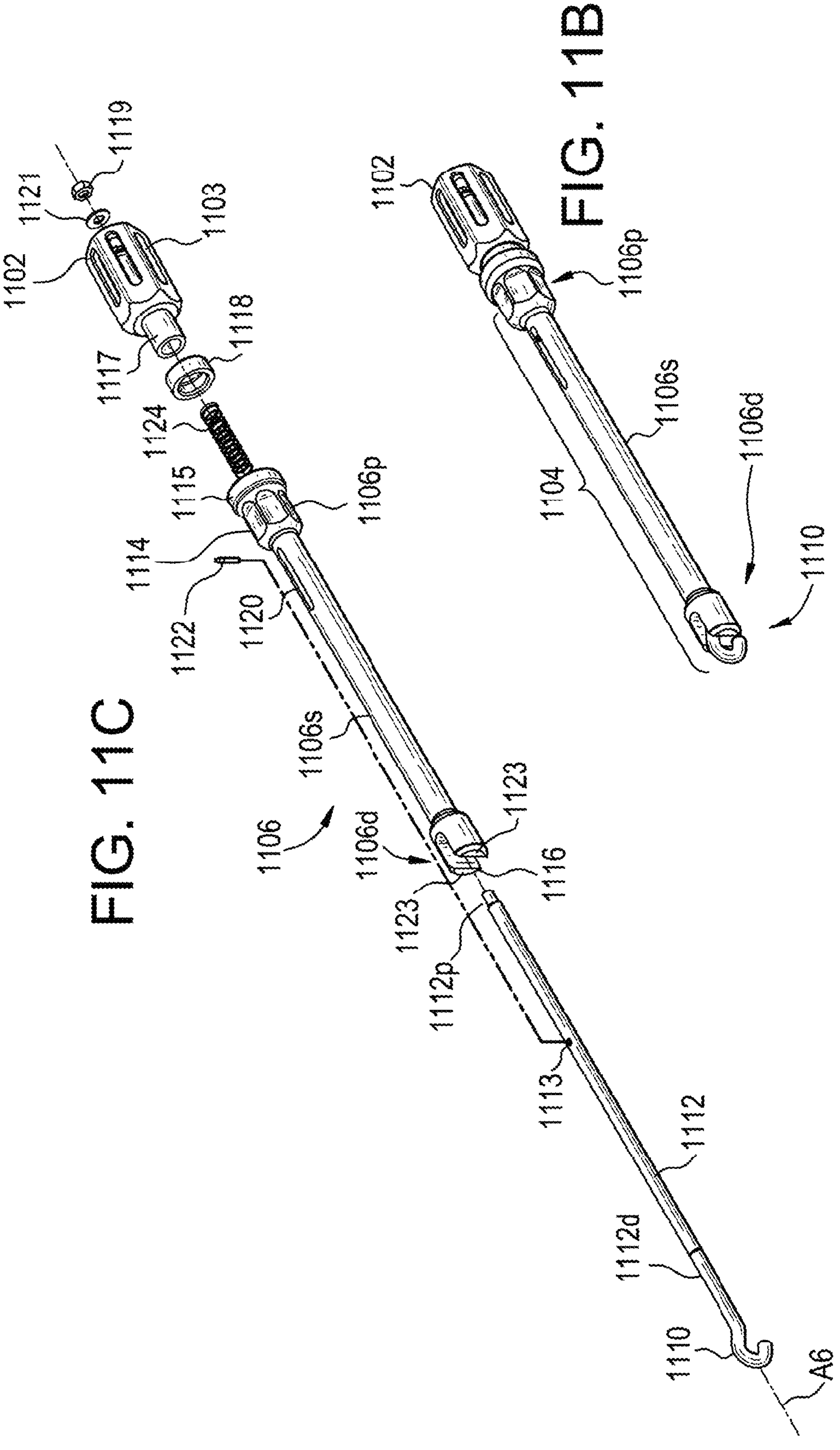
FIG. 11B is a perspective view of an arm assembly of the connector of FIG. 11A.
FIG. 11C is an exploded view of the arm assembly of FIG. 11B.

FIG. 11B shows the arm assembly 1104 with a handle 1102 connected to a proximal end thereof. A distal end of the arm assembly can include an engagement feature 1110. The engagement feature can be placed in an activated open position to receive an attachment feature. In a neutral position, as shown in FIG. 11B, the engagement feature is closed such that any attachment featured disposed within the engagement feature is held in contact with the distal end of the arm assembly.

The arm assembly 1104 and the handle 1102 are shown in greater detail in FIG. 11C. An arm body 1106 can include an elongate, generally-cylindrical shaft **1106*s*, with proximal end 1106*p* and distal end 1106*d*, extending along a longitudinal axis A6. In one embodiment the proximal end and the distal end of arm body 1106 may each have a diameter greater than a diameter of the shaft portion 1106*s*. The arm body can define an inner passage 1116 extending between the proximal and distal ends 1106*p*, 1106*d*. An actuation shaft 1112 can be slidably received within central passage 1116. The arm body shaft 1106*s* can include a slot 1120 extending in a longitudinal direction along a portion of the shaft. Preferably, the slot 1120 is located towards a proximal portion of arm body 1106. The slot 1120 can be configured to receive a pin 1122, the pin being movable in a longitudinal direction within the slot. The pin 1122 is sized to engage with an opening 1113 along the actuation shaft 1112. As the actuation shaft 1112 translates along axis A6 within the arm body 1106, the pin 1122 translates accordingly within the slot. Movement of the pin 1122 is bounded by proximal and distal ends of slot 1120. The proximal and distal ends of the slot may be shaped to have a geometry complementary to that of the pin 1122. Further translation of the actuation shaft 1212** in the proximal or distal direction is prevented when the pin reaches the proximal or distal end, respectively, of the slot.

The proximal end of the arm body **1106*p* can include a receiving body 1114. Receiving body 1114 provides for a connection between the arm assembly 1104 and handle 1102. Inner passage 1116 can extend through receiving body 1114 and be concentrically aligned with an inner cavity 1103 of the handle 1102 to form a continuous bore extending from the distal end of the arm body 1106*d* to the proximal opening of the handle 1102. Receiving body 1114 may be generally cylindrical in shape with a receiving body recess. The receiving body 1114 may be open at a proximal end and may be attached to arm shaft 1106*s* at a distal end. The receiving body recess can receive a distal projection 1117 of the handle 1102. The receiving body may have a shoulder 1115 at a proximal end. The shoulder 1115 can have a smooth outer surface, while an outer surface of the receiving body can be faceted such that it may, for example, be easily engaged with a tool or may easily and stably be gripped by a user. A ring 1118 can be placed between a proximal facing side of the shoulder 1115 and a distally facing shoulder of handle 1102, with projection 1117** extending therethrough.

Handle 1102 can be generally cylindrical in shape. The handle can be formed such that a user may easily hold and rotate handle 1102 to operate the connector 1100. As shown in the exemplary embodiment of FIGS. 11A-11C, handle 1102 may have faceted sides. One or more openings can be formed in the sidewall of the handle, which can advantageously allow sterilizing solutions, cleaning agents, or other flowable materials to access an interior of the handle. The illustrated handle includes a plurality of elongate slits that are open to inner cavity 1103 and spaced about the circumference of the handle. The handle can include features to facilitate gripping and application of torque thereto such as textured surfaces, faceted surfaces, knurling, grooved surfaces, etc. The handle cavity 1103 can be axially aligned with inner passage 1116 and can receive a proximal end **1112*p* of actuation shaft 1112. A proximal end of the handle 1102 may be open, while a distal end of the handle 1102 can have projection 1117 extending therefrom. The distally facing shoulder of handle 1102 can serve as a transition between the projection 1117 and handle 1102. The projection 1117 may have a narrower diameter than the handle. The projection can have an interior axial channel or recess with an inner diameter of substantially the same size of the inner passage 1116. The actuation shaft 1112 can extend through the axial channel of the projection and into the axial cavity 1103** of the handle.

A washer 1121 and a nut 1119 can engage the proximal end of the actuation shaft 1112*p* received within the handle body cavity 1103. The proximal end of the actuation shaft can have exterior threads that can threadably engage with interior threads of the nut. The proximal end of the actuation shaft 1112*p* can have a reduced diameter such that a shoulder is formed on the actuation shaft. The shoulder can serve as a stop, restricting further distal movement of the nut 1119 along the actuation shaft. The washer 1121 and nut 1119 may be placed onto the proximal end of the actuation shaft once the actuation shaft is inserted into the grip and extends into the handle cavity. The washer and nut may be inserted via the open end of the handle onto the proximal end of the actuation shaft. The handle can be configured such that rotation of the handle results in simultaneous rotation of the nut with respect to the threaded proximal portion of the actuation shaft. Rotation of the handle 1102 in a first direction can draw the actuation shaft 1112 proximally along the A6 axis. Rotation of the handle 1102 in a second direction can cause the actuation shaft to move distally along the axis A6.

The distal end 1106*d* of arm body 1106 may be substantially U-shaped having first and second parallel spaced apart arms extending distally from the arm shaft. A recess between the spaced apart arms can be sized to receive an engagement feature 1110 of the actuation shaft 1112, described in further detail below. The first and second parallel spaced apart arms can have distal-facing surfaces 1123 that extend perpendicular to the axis A6 and can act as a stop for the engagement feature 1110.

With continued reference to FIG. 11C, actuation shaft 1112 can include an elongate, generally-cylindrical body having proximal end 1112*p* and distal end 1112*d*. The actuation shaft can be sized to fit within the inner passage 1116 of arm body 1106. As described above, actuation shaft 1112 can extend through the inner passage 1116 and through the axial channel of the distal projection 1117 such that the proximal end 1112*p* of the actuation shaft can be received in the handle cavity 1103. Recess 1113 can be located along the body of the actuation shaft configured to engage the actuation shaft 1112 with pin 1122. Recess 1113 and pin 1122 can have complementary geometry such that the pin can be securely held by an interference fit within recess 1113. The recess 1113 is preferably located such that when the actuation shaft is received within the arm body, the recess aligns with a slot 1120 formed in the arm shaft 1106*s*.

Pin 1122 can be inserted into recess 1113 through slot 1120 when the actuation shaft 1112 is received within interior passage 1116. A compression spring 1124 can be received in passage 1116 such that the spring is coaxially located between the arm body 1106 and the actuation shaft 1112. The compression spring 1124 can bias the actuation shaft 1112 in a proximal direction. For example, in one embodiment a distal end of the compression spring 1124 can be secured by the pin 1122 and a proximal end of the compression spring can be secured to a fixed point on the interior of the receiving body 1114. Thus, compression spring 1124 can expand distally in a tensioned state when the actuation shaft 1112 is moved distally along axis A6 and can bias the actuation shaft 1124 proximally. In other embodiments the spring can be arranged differently, e.g., to be in compression rather than tension, with the same effect of biasing the actuation shaft 112 proximally.

The distal end 1112*d* of the actuation shaft can include an engagement feature 1110. In a preferred embodiment, the engagement feature is a hook-like extension of the actuation shaft 1112. The engagement feature 1110 is preferably oriented at an angle with respect to the longitudinal axis of the actuation shaft 1112. When the actuation shaft is seated in a resting position within the arm 1106, engagement feature 1110 may extend, at least in part, beyond the distal end of the arm body 1106*d*. The compression spring 1124 biases the actuation shaft proximally to a position in which the engagement feature 1110 extends only minimally beyond the distal end of the arm body 1106*d*. In this closed position, the engagement feature 1110 cannot receive an engagement mechanism of an attachment feature 1108. The actuation shaft may be extended distally to an open position with application of a force on the distal end of the actuation shaft. The actuation shaft can translate distally along axis A6 relative to the body 1106 such that the engagement feature 1110 extends fully beyond arm body distal end 1106*d* and can engage with an engagement mechanism of an attachment feature, as described in detail below. Once an attachment feature is engaged with the actuation shaft via engagement feature 1110, the distal force on the actuation shaft can be released such that the actuation shaft and the engaged attachment feature are drawn proximally towards the arm assembly 1106. In a preferred embodiment, an engaged attachment feature can abut distal-facing end surfaces 1123 of the spaced apart arms of arm body distal end 1106*d*.

Figure 11D:
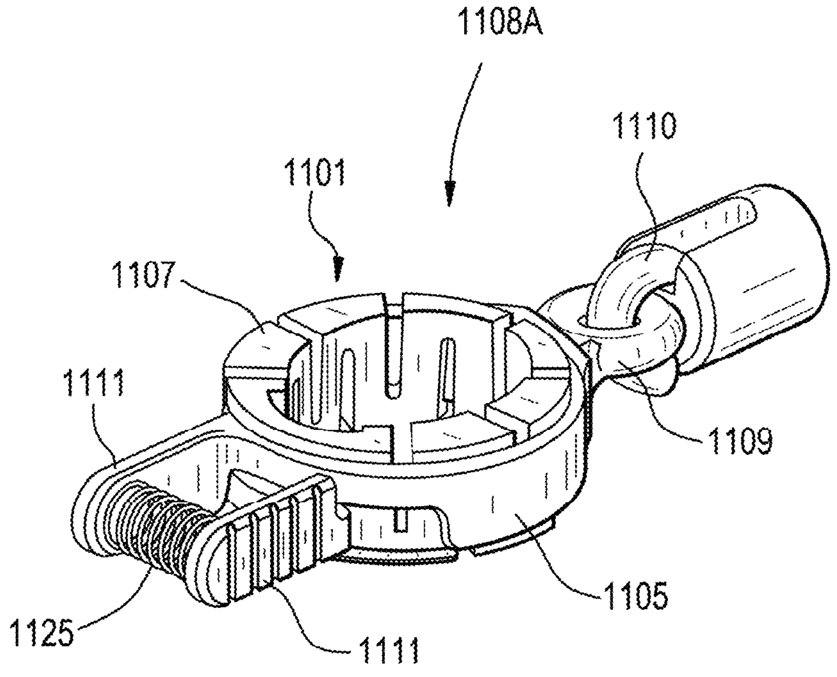
FIG. 11D is a perspective view of another attachment feature that can be used in the connectors herein.

FIG. 11D shows an exemplary embodiment of a double ring clamp attachment feature 1108A. The attachment feature 1108A can define a central opening 1101 through which an object, e.g., a surgical access device, can be received. A first ring, 1105, and a second ring 1107 can define the central opening 1101. The attachment feature 1108A can be positioned in a closed state, in which the attachment feature is locked with respect to an object disposed with the central opening to resist or prevent relative movement between the attachment feature 1108A and the object. The attachment feature 1108A can be positioned in an open state, in which an object can be inserted or removed from the central opening 1101. In the open state, an object located within the central opening can be moved in one or more degrees of freedom with respect to the attachment feature 1108A. The first and second rings 1105, 1107 can be made from material to allow radial expansion and contraction. The second ring 1107 can be made from a material more clastic than that of the first ring 1105. Second ring 1107 can be placed coaxially within the first ring 1105. An inner surface of the second ring can be in direct contact with an object placed therein. Second ring 1107 can have one or more cutouts or recesses formed along a vertical axis to allow for flexibility of the second ring to expand when a tensile force is applied.

The first ring 1105 can include an attachment feature engagement portion 1109. As shown in the embodiment of FIG. 11D, the engagement portion 1109 can be a ring that projects from an exterior surface of the first ring 1105. The engagement portion 1109 of the attachment feature 1108A can engage with engagement feature 1110 of the arm assembly 1104 to facilitate a secure attachment between the arm assembly 1104 and the attachment feature 1108A. First ring 1105 can include first and second extension tabs 1111 with a spring 1125 extending therebetween. Extension tabs 1111 can extend from an exterior surface of the first ring 1105. The first ring 1105 can be formed from a single component, such that extension tabs 1111 are unitary with the body of first ring 1105. As such, when a compressive force is applied to extension tabs 1111, a ring portion of first ring 1105 expands radially outward in tension. Extension tabs 1111 may have surface features to aid in a user grip of the extension tabs to facilitate application and removal of a compressive force. Compression spring 1125 can connect free standing distal ends of first and second extension tabs such that applying a compressive force to the distal end of the extension tabs compresses the spring.

As the first ring 1105 expands away from its resting state, second ring 1107 is drawn radially outward as well thereby enlarging the size of the central opening 1101. In this manner, the attachment feature 1108A is put into an open position. Upon removal of the compressive force from the distal ends of the extension tabs 1111, the spring 1125 can bias the tabs back to their resting position. This releases tension from the first ring, and the resilient material properties of the first ring and the second ring can cause both the first ring and the second ring to move radially inward towards the resting position. The return of the first and second rings 1105, 1107 to the resting positing is effective to secure an object within the central opening with respect to the attachment feature 1108A. In this manner, the attachment feature 1108A is brought into its "closed" or locked position. As illustrated in FIG. 11D, extension tabs 1111 can be located 180 degrees from the engagement portion 1109. It will be appreciated that there can be any of a variety of orientations between the engagement feature 1109 and the extension tabs 1111 of the first ring.

Figures 11E, 11F:
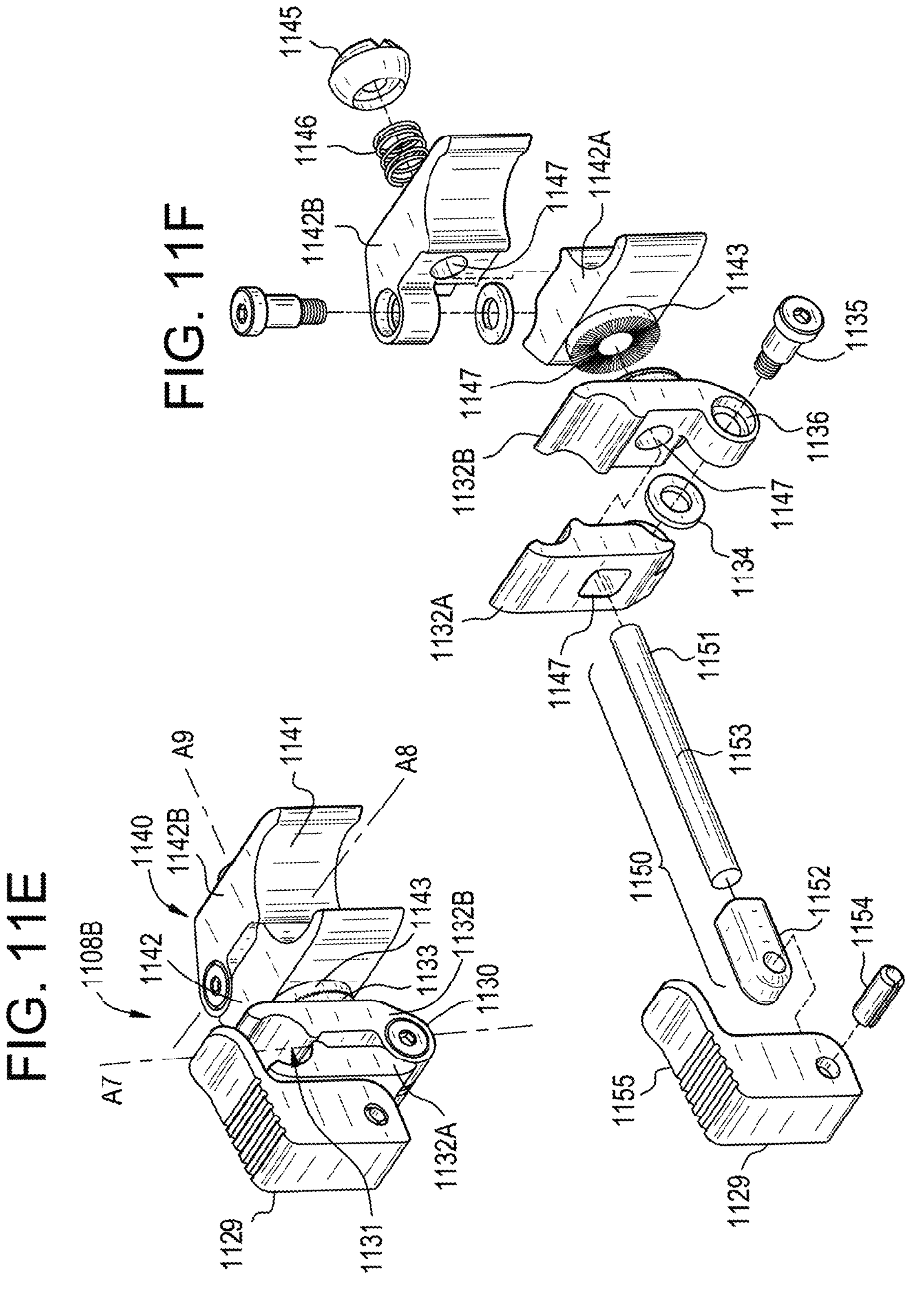
FIG. 11E is a perspective view of another attachment feature that can be used in the connectors herein.
FIG. 11F is an exploded view of the attachment feature of FIG. 11E.

FIG. 11E and FIG. 11F show another exemplary embodiment of an attachment feature in the form of cam lever clamp assembly 1108B. The cam lever clamp assembly can include a cam lever assembly 1129, first body 1130 and a second body 1140, the first body having proximal and distal ends that define a proximal-distal axis A7 extending therebetween and the second body having proximal and distal ends that define a proximal-distal axis A8 extending therebetween. A hinge pin 1150 can extend longitudinally from a distal portion of the cam lever body 1129 along a central axis A9. Hinge pin 1150 can adjustably couple the first body and the second body, such that the first and second bodies 1130, 1140 can rotate relative to one another about axis A9.

As can be seen in FIG. 11E, the first body 1130 and the second body 1140 may be oriented such that axis A7 extends in a substantially vertical direction while axis A8 extends in a substantially horizontal direction in the same plane. In such a configuration, the first body 1130 and the second body 1140 are rotated 90 degrees with respect to each other. One having ordinary skill in the art will appreciate that this is merely an exemplary orientation. Axes A7 and A8 may be oriented in a different configuration as a function of the relative rotation and positioning of first and second bodies. Axis A9 remains normal to a plane defined by axes Ab and A8, irrespective of first and second body orientation.

The first body 1130 can include a first receiving recess 1131, first and second arms 1132A, 1132B, and an outer bearing surface 1133. Arms 1132A and 1132B can extend parallel to each other in a vertical direction along axis A7. The first receiving recess 1131 may be defined between proximal ends of the first and second arms, such that a receiving axis of first receiving recess 1131 extends perpendicular to axis A7 of the first body. First arm 1132A and second arm 1132B can be secured to each other at a distal point of each arm. As shown in the exploded view of FIG. 11F, arms 1132A, 1132B can be held together by a washer 1134 and a screw 1135 engaging a through-hole 1136 located in the distal portion of the first arm and a through-hole located in the distal portion of the second arm (not shown). Washer 1134 can be placed between the through-hole of the first arm and the through hole of the second arm such that the washer is between the first arm and the second arm when the screw is inserted. It will be appreciated that other known joining means may be used to hold first arm 1132A and second arm 1132B securely together.

The first receiving recess 1131 can be configured to securely receive an object therein. In a preferred embodiment, first receiving recess 1131 may be sized to receive an arm shaft 1106*s* of arm assembly 1104. The first receiving recess can be open in a proximal direction, such that a rod or other object can be inserted into the recess by moving the rod or object distally into receiving recess 1131, or moving the receiving recess 1131 proximally with respect to the rod or object. Alternatively, a rod or other object can be translated along a longitudinal axis of the first receiving recess to place the rod or object into the first receiving recess.

With reference to FIG. 11E, cam lever body 1129 can have a proximal end with a lever portion 1155 and a distal end configured to secure the cam lever body 1129 to first and second bodies 1130, 1140. The lever 1155 can extend in a transverse direction over the first receiving recess to selectively lock the recess. The cam lever body 1129, may be secured to the first and second bodies 1130, 1140, by way of hinge pin 1150. A free end 1151 of the hinge pin 1150 can extend longitudinally from a base 1152. The base 1152 can be inserted into cam lever body 1129 such that through holes in the base 1152 and cam lever body 1129 align. A connector pin 1154 can be inserted into the through holes of base 1152 and cam lever body 1129 to secure the base 1152 within a recess of cam lever body 1129. The connector pin 1154 forms a hinge axis for actuation of the cam lever 1129. An upwards (in the direction of the figure, it should be noted that the required direction can change based on an orientation of the component) force on the lever 1155 rotates the cam lever lock 1129 in an upwards direction, thereby opening the first receiving recess 1131. Conversely, a downwards force on the lever 1155 hinges the cam lever lock 1129 to block the first receiving recess 1131 and lock the first body 1130 with respect to a rod or an object arm received in the first receiving passage 1131. The cam lever body 1129 can be placed in an open or a closed position. In the open position, the first receiving recess 1131 is unobstructed such that a rod or object may be inserted or removed. In the closed position, as shown in FIG. 11E, the cam lever 1155 can block the first receiving recess and secure a rod or object within the first receiving recess. Preferably, as shown in FIG. 11A, the cam lever 1129 can secure the arm shaft 1106*s* in the first receiving recess 1131.

As shown in FIG. 11F, the hinge pin assembly 1150 may be two separate components, a shaft 1153 and base 1152. Shaft 1153 may be permanently inserted into an axial bore of the base 1152 such that shaft 1153 extends longitudinally from the base. Alternatively, it will be appreciated that the hinge pin assembly can be formed as a single unitary component.

The hinge pin 1150 may extend from a first end of the base 1152. A second end of the base can received within the body of the cam lever 1129, and preferably can have features to facilitate a smooth insertion such as chamfered edges.

The first body 1130 can include an outer bearing surface 1133 configured to contact and bear against a corresponding bearing surface 1143 of the second body 1140. The respective bearing surfaces 1133, 1143 of the bodies 1130, 1140 can bear against one another to lock relative rotation between the bodies. In the embodiment shown in FIGS.

11E-11F, the first bearing surface 1133 can be located on an exterior surface of arm 1132B which can align with second bearing surface 1143 of the second body located on an exterior surface of arm 1142A. One or both of the bearing surfaces 1133, 1143 can include surface features for enhancing grip between the surfaces. For example, one or both surfaces can include teeth, grooves, roughening, surface textures or coatings, etc. In a preferred embodiment as shown in FIG. 11E, each bearing surface 1133, 1143 can include a plurality of teeth that extend radially outward from the rotation axis A9. The teeth can selectively interlock to maintain the bodies 1130, 1140 in one of a plurality of discrete rotational positions relative to one another. It will be appreciated, however, that various other arrangements can be used instead or in addition to the illustrated embodiment. For example, the bearing surfaces 1133, 1143 can include or can be defined by complementary male and female structures of the first and second bodies 1130, 1140.

The second body 1140 can be identical or substantially identical to the first body, 1130, or can have any of the features or variations described above with respect to the first body 1130. Second body 1140 can include a second receiving recess 1141, first and second arms 1142A, 1142B, and an outer bearing surface 1143. The second receiving recess may be defined at least in part by arms 1142A and 1142B. Arms 1142A and 1142B may extend along the second body axis A8. The second receiving recess 1141 may be defined between proximal ends of the first and second arms. A receiving axis of the second receiving recess 1141 may run perpendicular to the plane in which arms 1142A, 1142B extend. First arm 1142A and second arm 1142B can be joined together at a distal end opposite the second receiving recess 1141. In one embodiment, the first and second arms 1142A, 1142B can be held together by a washer and screw, in the same manner as described above with respect to the first body 1130.

Hinge pin 1150 can extend beyond exterior surface of arm 1142B to engage with a fastener such that first body, second body, and clamp lever body can be secured together. The free end 1151 of the hinge pin can engage with fastener 1145 to restrict axial motion of the first and the second bodies along A9. Each of the arms—1132A, 1132B, 1142A, and 1142B—can include an opening 1147 to receive hinge pin 1150. Openings 1147 can be of the same or different sizes. For example, openings 1147 may all be circular. In the exemplary embodiment of FIG. 11F, an opening 1147 of first arm 1132A can have a geometry complementary to base portion 1152 such that the base 1152 may be received by the opening when attachment feature 1108B is assembled. In one embodiment, base 1152 and opening 1147 of first arm 1132A may be generally rectangular in shape and may have chamfered edges.

A compression spring 1146 can be placed between the exterior surface of arm 1142B and the fastener 1145 to facilitate adjustment of the fastener. Rotation of the fastener in a first direction can be effective to urge the first and second bodies 1130, 1140 against one another. Rotation of the fastener in a second direction can be effective to release the connection of the first and second bodies such that the first and second bodies may move relative to one another. In one embodiment a user can engage a driver or other tool with the fastener 1145 to rotate the fastener. It will be appreciated that the illustrated fastener is exemplary, and various other fastener features can be used instead or in addition.

An exemplary method of using connector 1100 is also disclosed. The connector 1100 can be assembled for use in a surgical procedure such that the connector is configured to connect a first object, e.g., a surgical access device, and a second object, e.g., a support. A first attachment feature can be secured to a distal end of the arm assembly 1104. In one embodiment, the first attachment feature may be double ring clamp 1108A. An actuation shaft engagement feature 1110 can be extended distally from the arm body 1106 such that the engagement feature and a portion of the actuation shaft extend along axis A6 beyond the distal end of arm body 1106. For example, a user can grasp the distal end of the actuation shaft and move the actuation shaft distally along A6 away from the arm body 1106. An engagement feature of the first attachment feature, e.g., the engagement portion 1109 of the double ring clamp 1108A, can be received by the actuation shaft engagement feature, e.g., the engagement feature 1110, to hold the first attachment feature 1108A thereon. The actuation shaft 1112 can then be returned to its resting position such that only a distal end of the actuation shaft extends distally beyond the arm body 1106. For example, the user may release the actuation shaft so as to remove the user exerted force holding the actuation shaft in the distally extended position. Upon removal of the distal force from the actuation shaft, compression spring 1124 provided at the proximal end of the actuation shaft can bias the actuation shaft 1112 proximally within the arm assembly 1104 to a resting state. In this resting state the first attachment feature engagement portion 1109 can be held by actuation shaft engagement feature 1110 such that the first attachment engagement portion 1109 contacts distal-facing end surfaces 1123 of arm body distal end 1106*d*.

Figure 11G:
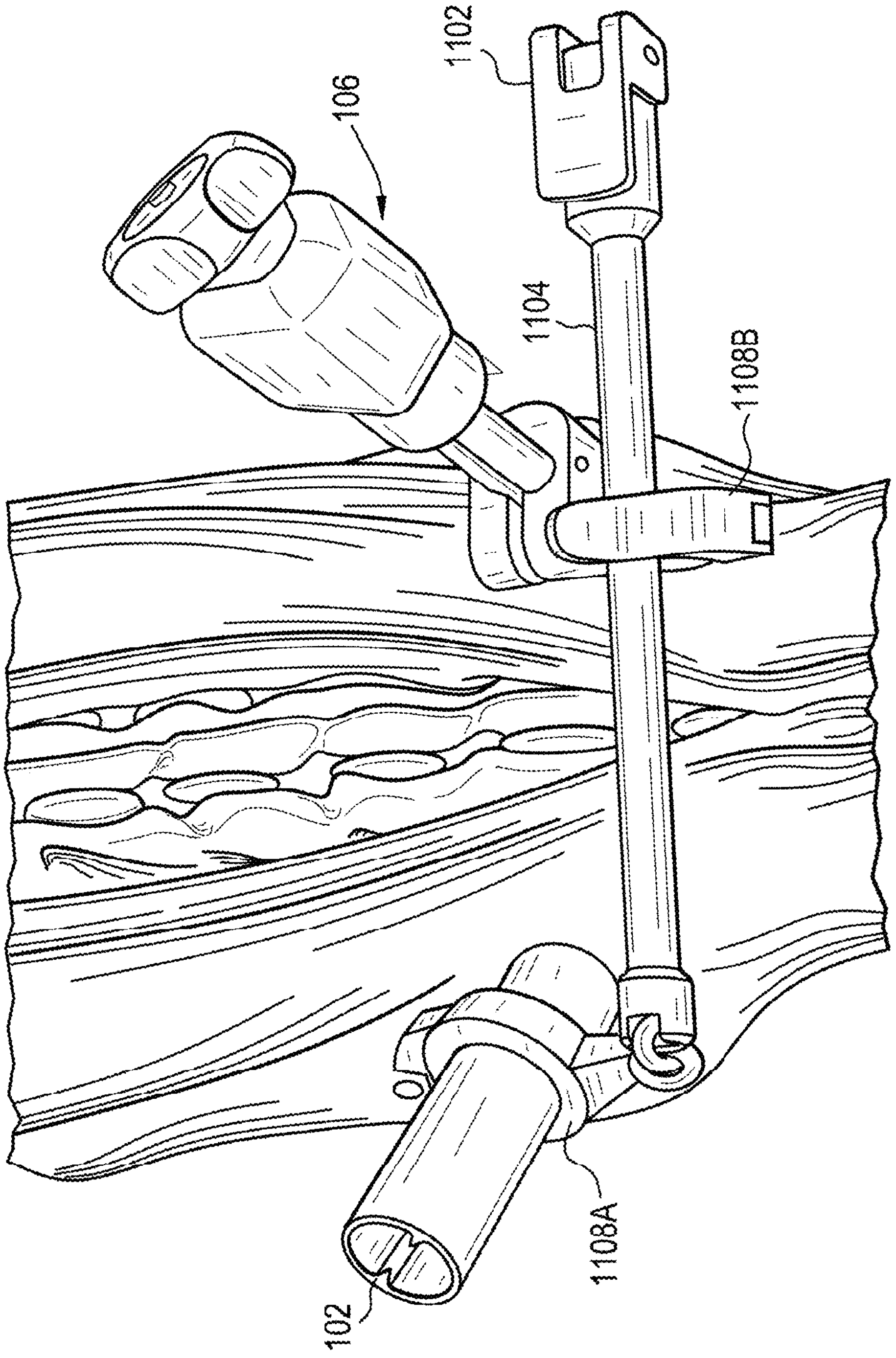
FIG. 11G is a perspective view of a connector in use to support a surgical access device in a spinal surgery.

The arm assembly 1104 can then be tightened such that the engaged first attachment feature 1108A is secured to the arm assembly 1104. To secure the engaged first attachment feature 1108A to the distal end of arm body 1106, actuation shaft 1112 can be drawn more proximally along axis A6. For example, the user can grasp handle 1102 and rotate the handle in a first direction. Rotation of the handle simultaneously rotates nut 1119 such that the nut draws the proximal end of the actuation shaft 1112*p*, threadably engaged with nut 1119, proximally along axis A6. The distal end of the actuation shaft, including engagement feature 1110 and engaged first attachment feature 1108A, translate in the proximal direction along A6, thereby tensioning the first attachment feature 1108A, by way of the engagement portion 1109 contacting the arm body distal end 1106*d*. FIG. 11G shows a modified embodiment of a connector 1100 with a cam lever handle 1182. The cam lever handle 1182 can be operated by a user to translate an actuation shaft proximally and distally along an inner passage of an arm body to achieve similar operation as the connector 1100, described above.

A second attachment feature can be placed on arm assembly 1104. In one embodiment, the second attachment feature can be cam lever clamp 1108B. Prior to attaching the cam lever clamp, first and second bodies 1130, 1140 can be adjusted to a desired rotational position relative to one another. The fastener 1245 can be tightened using an instrument to secure the first and second bodies and restrict further relative rotation. The cam lever clamp 1108B can then be placed in the open position. For example, a user can exert an upwards force on lever 1155 thereby opening first receiving recess 1131. The arm shaft 1106*s* can then be brought within receiving recess 1131. Cam lever clamp 1108B can be placed initially at a desired location or may be placed anywhere along the shaft 1106*s* and be translated axially along the shaft to a desire position at any time when the cam lever clamp 1108B is in the open position. The desired position can be a location such that an object, e.g., a support 106, can be received within the second receiving recess 1141. To secure the cam lever clamp 1108B along the shaft 1106*s*, the cam lever clamp can be placed in the closed position, for example, by a user exerted downwards force on lever 1155 to place the lever 1144 transversely across first receiving recess.

The assembled connector 1100 can then be used to connect a first and a second object. FIG. 11G shows an embodiment using connector 1100 to connect a surgical access device 102 and a support 106 at a surgical procedure sight. For example, the first attachment feature 1108A may engage a surgical access device 102 in the following manner. First ring extension tabs 1111 can be compressed such that the first ring 1105 expands radially outward. The surgical access device 102 can then be received within the central opening 1101. With the surgical access device 102 received within the central opening 11101, the extension tabs 1111 can be released to return the first ring 1105 radially inward to its resting state thereby tightening the engagement of the first and second rings 1105, 1107 around surgical access device 102. The second attachment feature 1108B can then receive a second object, e.g., support 106, in second receiving recess 1141. It will be appreciated that axial adjustment of the cam lever clamp 1108B along the shaft 1106*s* can be made at any time by opening the cam lever clamp, translating the cam lever clamp along arm shaft 1106*s*, and closing the clamp. In this manner connector 1100 can be used to secure a first and a second object.

Figure 12A:
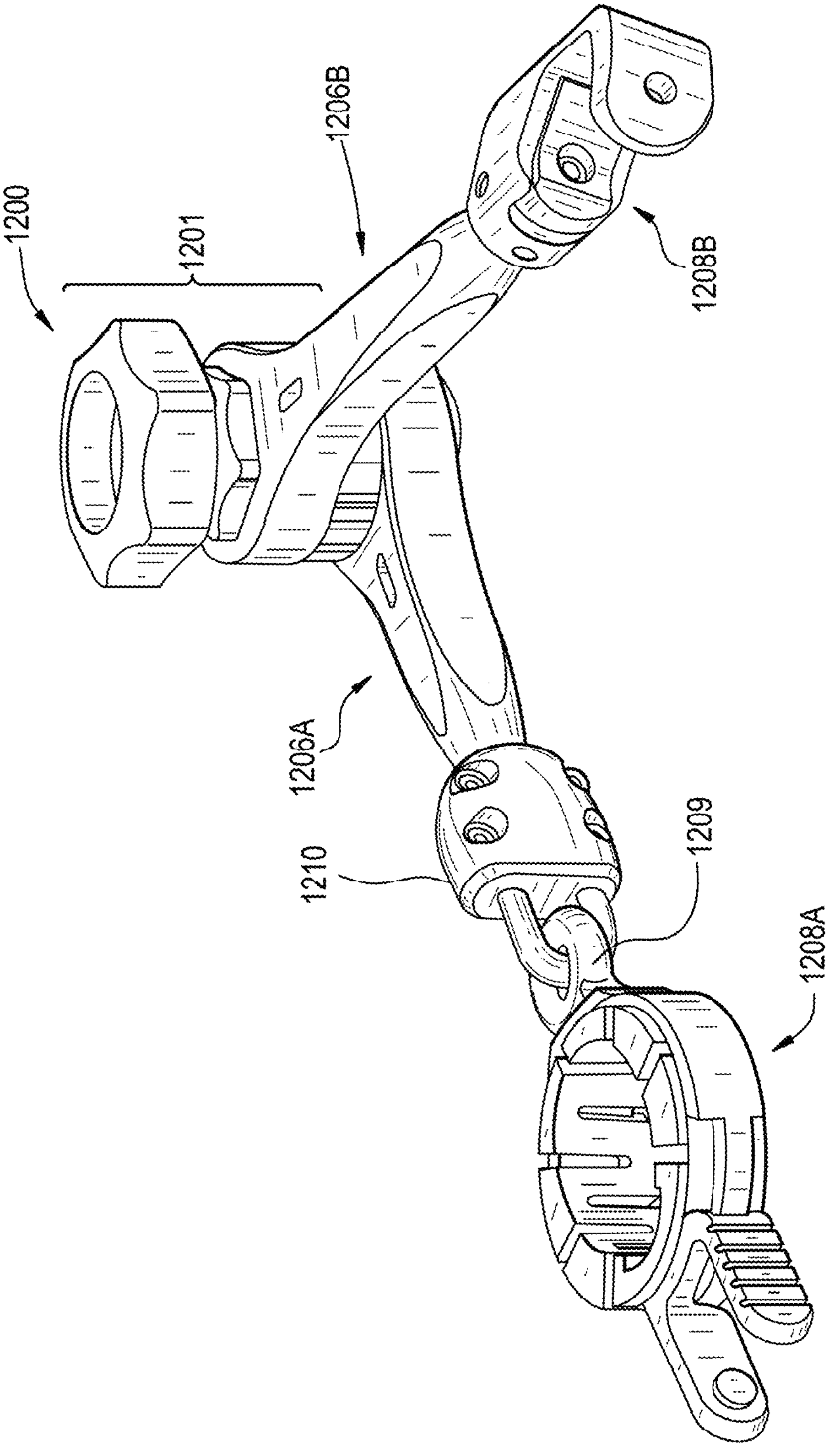
FIG. 12A is a perspective view of another embodiment of a connector.
Figure 12B:
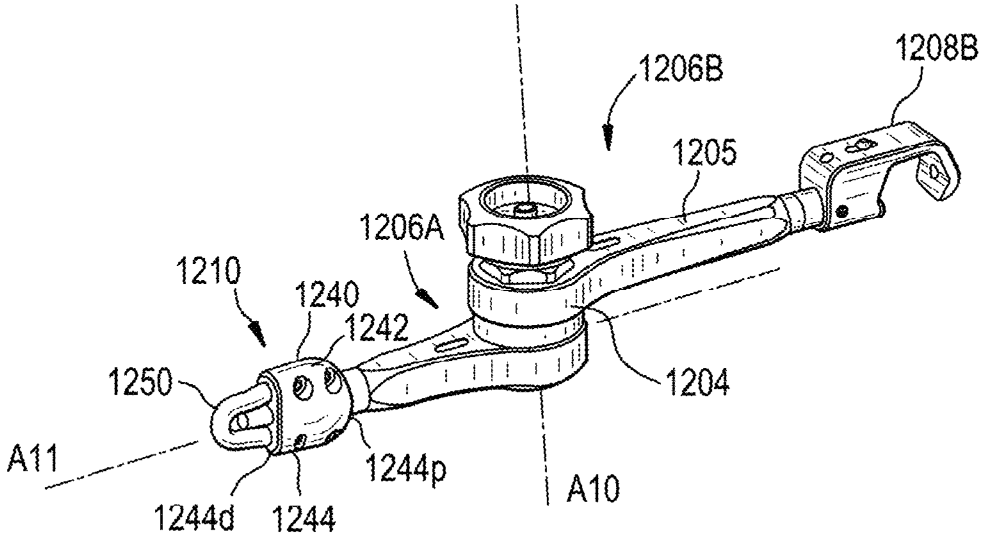
FIG. 12B is another perspective view of the connector of FIG. 12A.
Figure 12C:
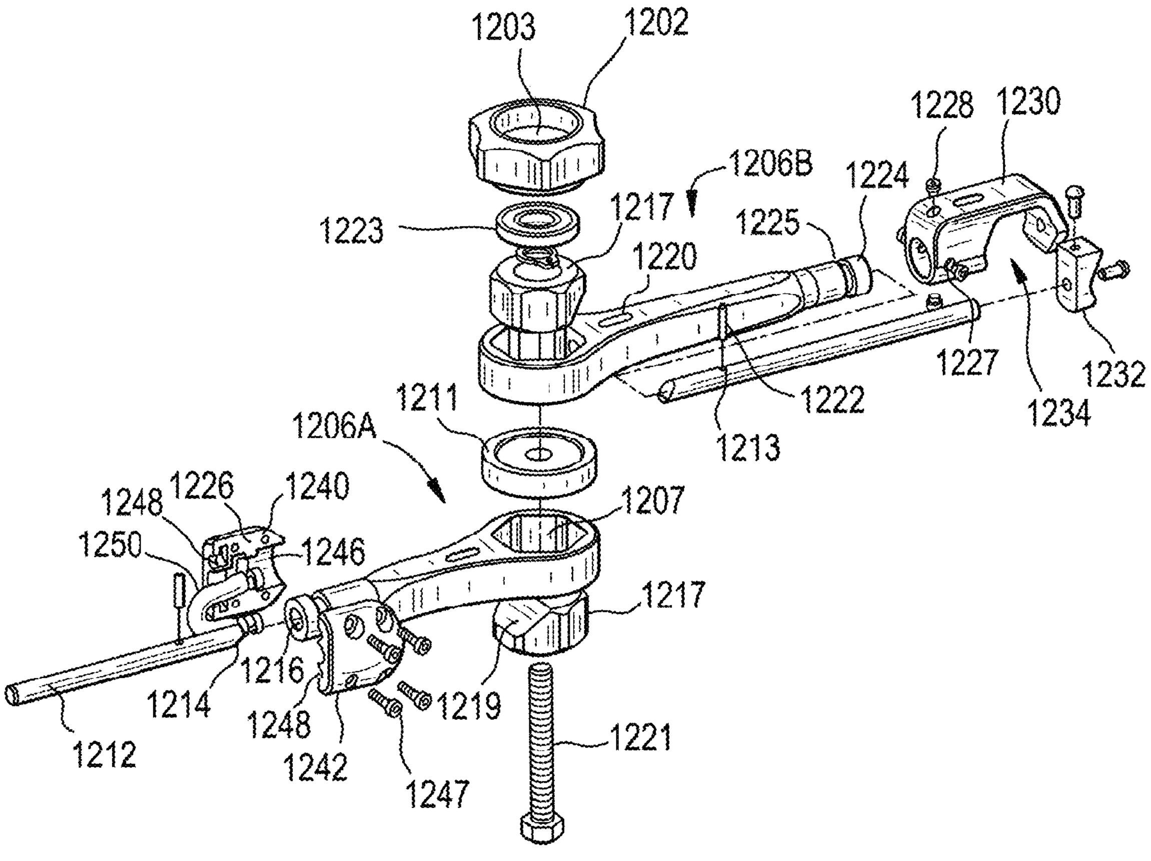
FIG. 12C is an exploded view of the perspective view shown in FIG. 12B.

FIGS. 12A-12C illustrate another exemplary connector 1200 that can be used to connect a first object to a second object. For example, the connector 1200 can be used to connect first and second surgical instruments. By way of further example, connector 1200 can be used in the system 100 described above, e.g., to connect surgical access device 102 to support 106. The support structure may include a pedicle post, bone anchor screw extension tabs, a part of a patient's anatomy, for example a patient's skin, an operating table etc. An exemplary use may include, e.g., anchoring a port to a patient's skin and may further include stabilizing the port by connecting the port to a support structure. Except as indicated below and will be readily appreciated by a person having ordinary skill in the art in view of the present disclosure, the structure and operation of the connector 1200 is substantially the same as that of the connector 800 described above.

Connector 1200 can include one or more rigid arms 1206, which can be rotatable with respect to each other and rotatable relative to a central axis A10 of the connector. FIG. 12A illustrates an embodiment of assembled connector 1200. Connector 1200 can include a first arm 1206A, a second arm 1206B, and an actuation assembly 1201. Each arm 1206A, 1206B can have a proximal portion configured to receive and engage with the actuation assembly 1201, and a distal portion to facilitate attachment to an object. For example, an arm may have an attachment feature directly placed on a distal end of the arm. Alternatively, an engagement feature can be placed directly on a distal end of the arm, the engagement feature connecting to an attachment feature to couple the attachment feature to the arm. In one embodiment, first arm 1206A can include an engagement feature 1210 which can connect an attachment feature to arm 1206A. In a preferred embodiment, the attachment feature can be a double ring clamp 1208A. In one embodiment, second arm 1206B can have an attachment feature directly placed on a distal end. In a preferred embodiment the attachment feature can be a side-loading jaw 1208B.

As shown in FIG. 12B, construction of each arm 1206A, 1206B can be substantially similar. Each arm 1206 can include a first tubular portion 1204 that extends along a central connector axis A10 and a second tubular portion 1205 that extends along a longitudinal axis of the arm A11. It will be appreciated that the first tubular portion 1204 and the second tubular portion 1205 may be a single unitary component, or may be formed of several components joined together in a manner known in the art. Arms 1206A, 1206B may be of equal size. Alternatively, the one or more arms may have differing dimensions.

FIG. 12C shows a detailed exploded view of connector 1200. Each arm 1206A, 1206B can define an inner passage 1216 in which an actuation shaft 1212 can be slidably disposed such that the actuation shaft can translate along the longitudinal axis A11 of the arm. The inner passage 1216 can extend through the first tubular portion 1204 and the second tubular portion 1205 such that the inner passage 1216 communicatively connects with an opening 1207 in the first tubular portion 1204 with a distal face of arm 1206. The actuation shaft can have a proximal end with a ramped exterior surface 1214. The actuation shaft can be placed within the arm 1206 such that the ramped exterior surface 1214 is disposed in the inner passage 1216 of the first tubular 1204 and extends into central opening 1207.

First tubular portion 1204 and central opening 1207 can be axially aligned with the central axis A10 of the connector. Central opening 1207 can be configured such that a bushing 1217 can be coaxially received within the opening. In one embodiment the geometry of the opening is complementary to the geometry of the bushing. As shown in FIG. 12C, the opening 1207 may have a hexagonally shaped perimeter to accommodate a bushing 1217 with a hexagonal contour, thereby preventing rotation of the bushing 1217 relative to the arm 1206. It will be appreciated that the bushing and the opening can have any of a variety of geometries, and can have a non-circular geometry to restrict rotation of the bushing within the first opening. Bushing 1217 can have a central channel or lumen extending therethrough, sized to receive a shaft 1221. The bushing can include a ramped exterior surface 1219. The bushing 1217 can be placed in central opening 1207 such that the ramped exterior surface 1219 aligns with an opening of the inner passage 1216. The ramped exterior surface 1219 can contact the ramped surface 1214 of the proximal end of actuation shaft 1212 when the actuation shaft 1212 is inserted into passage 1216. The ramped exterior surface 1219 of the bushing 1217 and the ramped exterior surface 1214 of the actuation shaft 1212 can be complementary such that a translation of the bushing 1217 along axis A10 can result in movement of the actuation shaft 1212 along the longitudinal axis A4 of the arm.

In an assembled connector configuration, arms 1206A, 1206B can be aligned such that respective openings 1207 and the corresponding coaxially received bushing 1217 of each arm are centered about the axis A10. In one embodiment, arm 1206B can be placed proximal along axis A10 with respect to first arm 1206A. A ring 1211 can be placed between the first tubular portion 1204 of arm 1206A and the first tubular portion 1204 if arm 1206B. Ring 1211 can promote easy and independent rotation of the one or more arms relative to each other. A handle 1202 is located at a proximal end of the connector 1200 along the axis A10. The handle 1202 can have an interior recess 1203 extending axially therethrough. The interior recess 1203 of the handle can have interior threads and can be sized to threadably receive a proximal end of the shaft member 1221. The handle may be configured such that a user can easily rotate the handle using a single hand. A ball bearing connector 1223 may be placed between a distal-facing end of the handle and a proximal facing end of a proximal bushing 1217 to facilitate easy rotation of the handle relative to the bushing. A retaining ring can be inserted into the axial channel of the proximal bushing to aid in securing the ball bearing connector.

The various components of connector 1200 described above can form an actuation assembly 1201. Actuation assembly 1201 can simultaneously lock relative rotation of arms 1206A, 1206B and secure an object at the distal end of each arm. The actuation assembly 1201 can include the handle 1202, bushing 1217 in association with the actuation shaft 1212 of each arm 1206A, 1206B, and shaft 1221. The shaft 1221 can extend axially through the central lumen of each bushing 1217 to the handle 1202, operatively connecting arms 1206A, 1206B with the handle 1202. In one embodiment, the shaft 1221 may have external threads. In some embodiments, shaft 1221 can be a bolt. The proximal end of shaft 1221 can be received in handle 1202 such that shaft 1221 rotates with rotation of handle 1202.

In the illustrated embodiment of FIGS. 12A-12C, rotation of the handle by a user in a first direction results in proximal, upwards, movement of the shaft 1221 along the axis A10. This movement results in an upwards force on bushing 1217, causing the exterior ramped surface 1219 of the bushing to move in a proximal direction. As bushing 1217 moves proximally, the exterior ramped surface 1214 of the actuation rod slides along the exterior ramped surface 1219 of bushing 1217. This can cause the actuation shaft 1212 to translate distally along arm axis A11. Proximal translation of the shaft 1221 compresses the first tubular portions 1204 of the arms 1206A, 1206B towards one another to lock relative rotation between arms 1206A, 1206B about the axis A10. It will be appreciated that the shaft 1221 and one or more bushings 1217 can be formed independently, as shown in the embodiment of FIGS. 12A-12C, or can be a single unitary component such that the shaft is rotatably fixed relative to the bushings. Actuation rod 1212 can include a recess 1213 configured to receive a pin 1222 through a slot 1220 formed in the arm 1206. The pin 1222 can translate within slot 1220 as actuation shaft 1212 translates along inner passage 1216. The slot 1220 can restrict translation of the pin 1222 and the associated actuation shaft 1212, from translating beyond a desired position in a proximal or distal direction.

Distal end of arm 1206 can be configured to securely attach to a proximal end of an engagement feature, e.g., engagement feature 1210, or an attachment feature, e.g., side-loading jaw 1208B. A flange 1224 can be formed at the distal end of arm 1206 to form a proximal facing shoulder and a circular groove 1225. The actuation shaft 1212 can extend distally beyond the flange 1224. An attachment feature or an engagement feature can be secured onto the distal end of arm 1206 in a variety of ways through interaction with the circular groove 1225. For example, engagement feature 1210 can have internal projections 1226 that are sized to fit within circular groove 1225. With projections 1226 aligned in the circular groove 1225, the engagement feature can be secured onto distal end of the arm 1206, for example, with one or more screws extending from a first side of the engagement feature into a second side of the engagement feature. By way of further example, an attachment feature 1208B can include an axial channel extending from a proximal face of the attachment feature 1208B. Through holes 1227 can be located in a circumferential manner around a proximal portion of the axial channel such that when a distal end of arm 1206 is inserted into the axial channel, through holes 1227 can be aligned with circumferential groove 1225 of the distal end of arm 1206. A set screw 1228 can be inserted in the one or more through holes 1227 and tightened to sit within groove 1225, thereby securing the distal end of arm 1206 to the attachment feature.

An exemplary embodiment of an attachment feature 1208 is shown in FIG. 12C as side loading jaw 1208B. Side-loading jaw can be attached to the distal end of arm 1206B as described above. Side loading jaw 1208B can include a sleeve 1230 and a movable jaw 1232 that collectively define a receiving recess 1234. The receiving recess 1234 can be open in a lateral direction such that an object can be introduced into the recess 1234 by moving the object perpendicular or substantially perpendicular to the longitudinal axis A11. A distal end of the actuation shaft 1212 can be secured to a proximal facing surface of the movable jaw 1234 with, for example, a set screw. A slot can be formed on an exterior surface of sleeve 1230 such that a screw or pin can be inserted into the slot to engage with a surface of the movable sleeve 1232. Translation of the movable sleeve 1232 can be restricted by the screw or pin and slot in a similar manner as described above with respect to the actuation shaft 1212 and the arm 1206. When the actuation shaft 1212 is translated distally within the inner passage 1216 of the arm 1206, the distal end of actuation shaft 1212 can urge the movable jaw 1232 distally to reduce the size of receiving recess 1234 and secure an instrument placed in the receiving recess 1234 between the movable jaw 1232 and a distal end of the sleeve 1230. Conversely, when the actuation shaft 1212 is drawn proximally along axis A11, the movable jaw 1232 can move proximally to increase the size of receiving recess 1234 and release an instrument from between the jaw 1232 and the sleeve 1230.

As discussed above, an engagement feature 1210 can be used with a connector system 1200 to permanently engage an attachment feature 1208 with an arm 1206. With continued reference to FIG. 12B and FIG. 12C, engagement feature 1210 can have a first and second side 1240, 1242 which can be joined together to form engagement feature body 1244. Body 1244 can have a proximal end 1244*p* and a distal end 1244*d* with an axial channel 1246 extending therebetween. Axial channel 1246 can be formed by interior surfaces of the first and second sides 1240, 1242 when the sides are secured together. The interior surfaces of the first and second sides 1240, 1242 can include identical or substantially identical recesses such that when the first and second sides are secured together axial channels are formed within the engagement feature body 1244. An interior surface of the first side 1240 can have an axial recess shaped to receive distal end of arm 1206 and associated actuation shaft 1212. For example, interior surface of the first body can include an axial channel 1246 extending therethrough with a projection 1226 extending laterally into the channel, the projection configured to engage circular groove 1225 of the arm 1206. Recesses 1248 can be formed above and below the axial channel 1246 at the distal end of first side 1240. Recesses 1248 can be formed to match a geometry of an engagement hook 1250. Engagement hook 1250 can be substantially U-shaped, with two parallel arms that may be seated within engagement feature 1210. Proximal ends of recesses 1248 and the two parallel arms of engagement hook 1250 can both have a flanged portion at their respective proximal ends to ensure that during translation of the engagement hook, the engagement hook 1250 remains within the recesses 1248 of engagement feature 1210. The interior surface of the second side 1242 can be substantially the same as the first side 1240.

The distal end of arm 1206 with actuation shaft 1212 received therein can be placed into the axial channel 1246 of the first engagement side 1240 such that the lateral projection 1226 is received within the circular groove 1225. The engagement hook 1250 can be slid through an engagement portion of an attachment feature, e.g. an engagement portion 1209 of a double ring clamp 1208A. The engagement hook 1250 coupled with the engaged attachment feature 1208A can be placed in the first side 1240 such that the two parallel arms of the engagement hook 1250 sit within recesses 1248. The second side, which has substantially the same interior geometry as the first side, can then be aligned with the first side over the distal end of arm 1206 and the engagement hook 1250. The second side 1242 can be secured to the first side 1240 using set screws 1247 that can be inserted into through holes in the second side and received by aligned recesses on the interior surface of the first side 1240. When assembled, actuation shaft 1212 can slidably extend distally from the engagement body 1244 to exert an axial force against the engagement portion, e.g. engagement portion 1209, of the attachment feature held by hook 1250 to tightly tension the attachment feature against the engagement hook 1250 and secure the attachment feature to arm 1206.

In an exemplary method of use, a connector 1200 of the type shown in FIG. 12A can be used to connect first and second objects. Double ring clamp 1208A can receive an object, e.g., a surgical access device, in the same manner as described above with reference to double ring clamp 1108A. With the first object received within double ring clamp 1208A, arms 1206A, 1206B can be rotated with respect to each other to a desired position. In one embodiment, the desired position is one such that the second attachment feature, e.g., side-loading clamp 1208B, can receive a second object, e.g., support 106, within receiving recess 1234. After placing the arms at the desired positions, handle 1202 can be rotated to simultaneously lock (1) the attachment feature, e.g., double ring clamp 1208A, securely to the first arm 1206A, (2) the second object, e.g., support 106, within the attachment feature, e.g., cam lever clamp 1208B, of the second arm 1206B, and (3) the angular position of the first and second arms 1206A, 1206B about the axis A10.

Figure 13A:
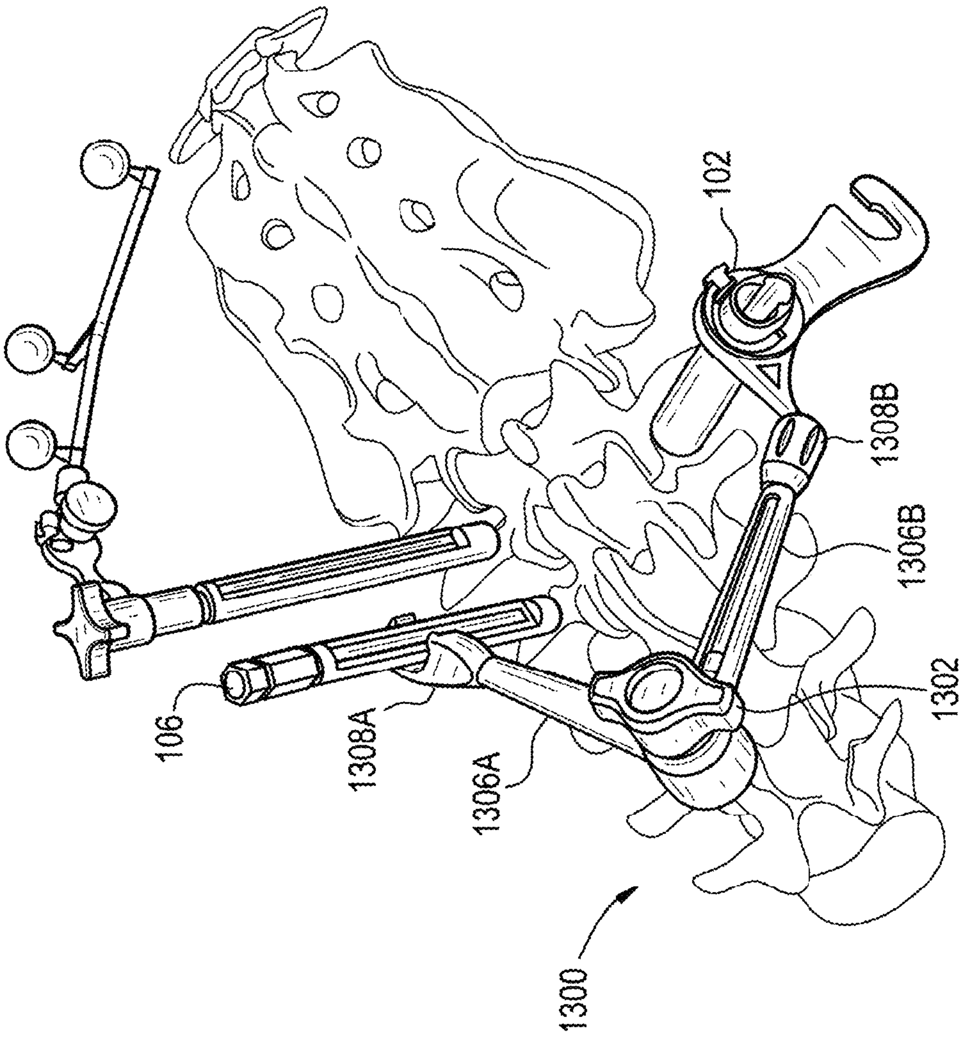
FIG. 13A is a perspective view of another embodiment of a connector in use to support a surgical access device in a spinal surgery.
Figure 13B:
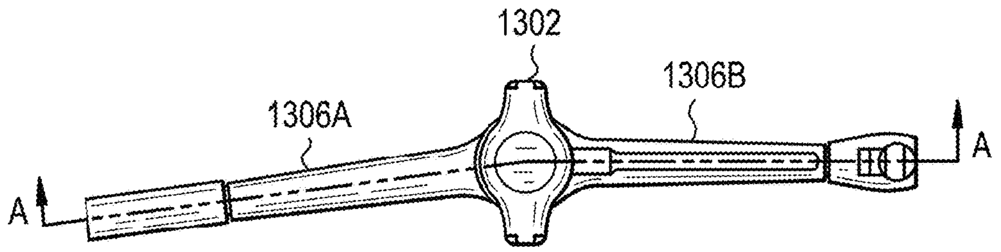
FIG. 13B is a top view of the connector of FIG. 13A.
Figure 13C:
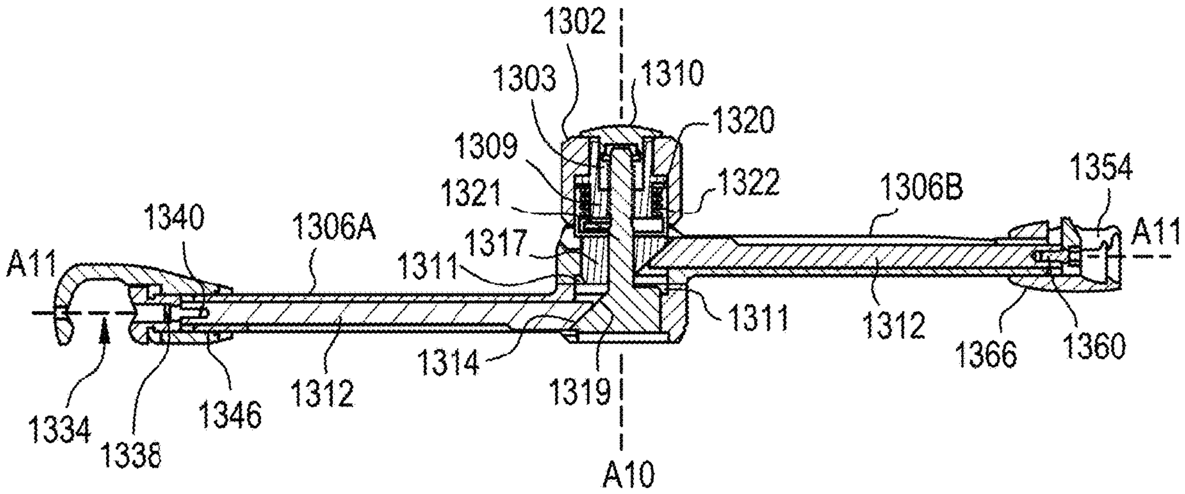
FIG. 13C is a cross sectional view of the view of the connector in FIG. 13B.
Figure 13D:
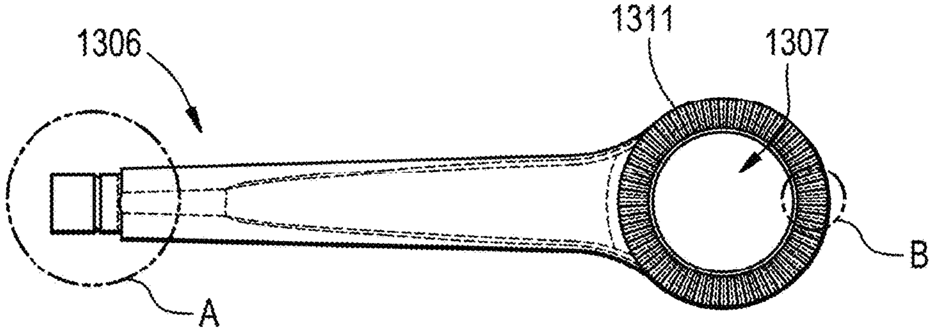
FIG. 13D is a top view of an arm of the connector of FIG. 13A.
Figure 13E:
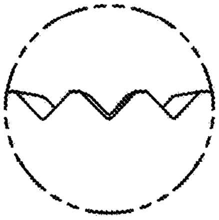
FIG. 13E is a view of a bearing surface of the arm of FIG. 13D.
Figure 13F:
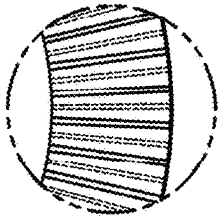
FIG. 13F is a detailed view of a bearing surface of the arm of FIG. 13D.
Figure 13G:
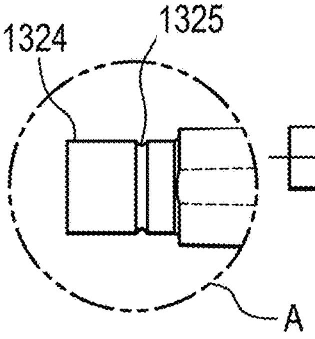
FIG. 13G is a view of a distal end of the arm of FIG. 13D.
Figure 13H:
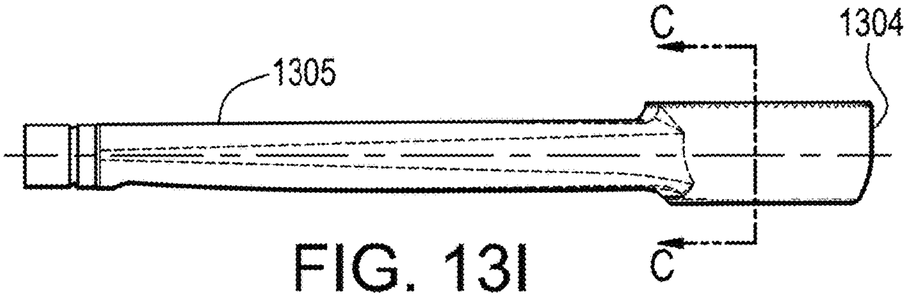
FIG. 13H is another view of an arm of the connector of FIG. 13A.
Figure 13I:
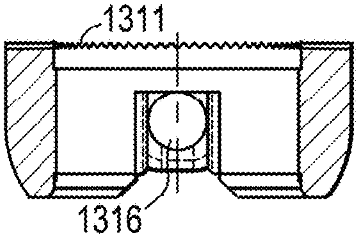
FIG. 13I is a cross sectional view of the arm of FIG. 13H.
Figure 13J:
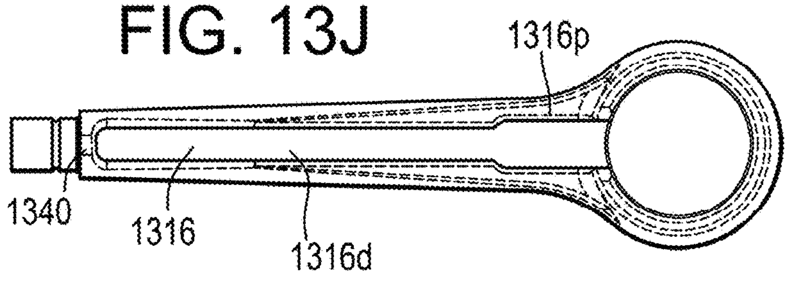
FIG. 13J is another view of an arm of the connector of FIG. 13A.
Figure 13K:
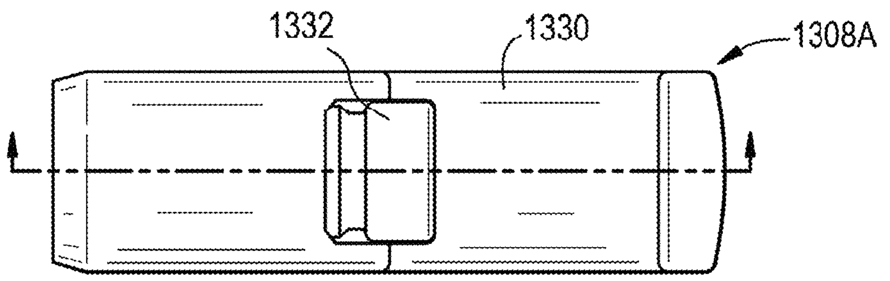
FIG. 13K is a view of another attachment feature that can be used in the connectors herein.
Figure 13L:
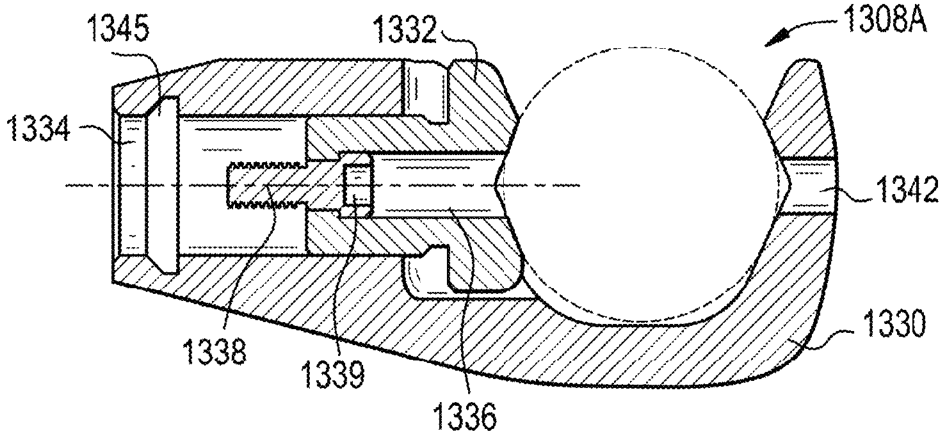
FIG. 13L is a cross sectional view of the attachment feature of FIG. 13K.
Figure 13M:
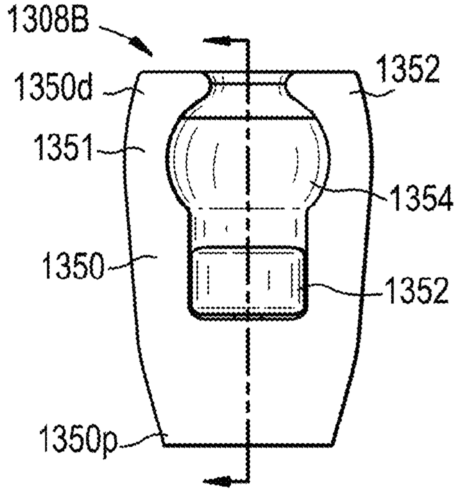
FIG. 13M is a view of another attachment feature that can be used in the connectors herein.
Figure 13N:
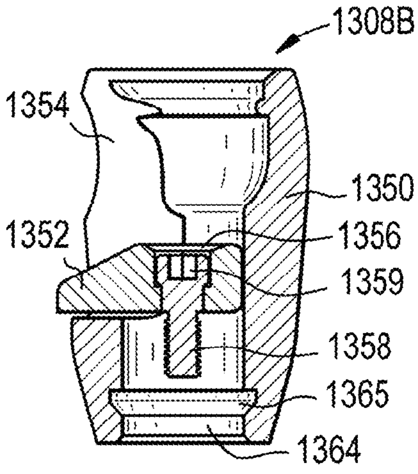
FIG. 13N is a cross sectional view of the attachment feature of FIG. 13M.

FIGS. 13A-13N illustrate another exemplary connector 1300 that can be used to connect a first object to a second object. For example, the connector 1300 can be used to connect first and second surgical instruments. By way of further example, the connector 1300 can be used in the system 100 described above, e.g., to connect access device 102 to support 106. For example, connector 1300 can be used to anchor a port to a patient's skin. Except as indicated below and as will be readily appreciated by a person having ordinary skill in the art in view of the present disclosure, the structure and operation of the connector 1300 is substantially the same as that of the connector 1200 described above.

FIG. 13A shows an exemplary system using connector 1300 in a spinal surgical procedure. Connector 1300 can include a handle 1302 and one or more arms 1306 in connection with an attachment feature 1308. In a preferred embodiment, connector 1300 can include a first arm 1306A with a first attachment feature 1308A, and a second arm 1306B with a second attachment feature 1308B. By way of non-limiting example, the first attachment feature 1308A can engage support 106, e.g., a pedicle post, and the second attachment feature 1308B can engage a surgical access device 102, e.g., a surgical port. First and second arms 1306A, 1306B can be rotatable relative to each other and can be rotatable relative to central axis A10 of the connector.

Arm 1306 can be identical or substantially identical to arm 1206, or can have any of the features or variations described above with respect to the arm 1206. Accordingly, only a brief description of arm 1306 is provided here for the sake of brevity. FIGS. 13D-13J show arm 1306 in greater detail. Arm 1306 can have a first tubular portion 1304 and a second tubular portion 1305. The first tubular portion can have a central opening 1307. In one embodiment, the first tubular portion can include a ring shaped bearing surface 1311 surrounding central opening 1307. The bearing surface 1311 can include at least one surface feature for enhancing grip with an adjacent surface. For example, bearing surface 1311 can include teeth, grooves, roughening, surface textures or coatings, etc. In an exemplary embodiment shown in FIG. 13E, bearing surface 1311 includes a plurality of teeth. When a first bearing surface 1311 contacts a second bearing surface 1311 teeth of the respective bearing surfaces can selectively interlock to maintain their respective arms 1306 in one of a plurality of discrete rotational positions relative to one another. FIG. 13G shows a detailed view of a distal end of arm 1306, which can be configured to securely engage with another object. The distal end of arm 1306 can include a flange 1324 and a circular groove 1325. Similar to the distal end of arm 1206, the flange and circular groove can aid in engagement between the arm 1306 and an external feature. FIG. 13I shows a cross sectional view of the first tubular portion 1304 of arm 1306. An inner passage 1316 can extend longitudinally through arm 1306. With reference to FIGS. 131 and 13J, a proximal end of passage 1316 can extend through first tubular portion 1304 and have an open face into central opening 1307. Passage 1316 can extend distally though the second tubular portion 1305 to a terminal end opening in a distal face of flange 1324. An inner surface of the passage 1316 can taper from a proximal portion of the passage 1316*p* to a distal portion of the passage 1316*d*, such that the proximal portion 1316*p* can have a larger diameter than a distal portion 1316*d*.

FIG. 13C shows a detailed view of connector 1300. Connector 1300 can include a control shaft 1321 extending axially along A10 and having at least one ramped exterior surface 1319. Ramped exterior surface 1319 can be formed integrally with control shaft 1321 or on one or more bushings 1317 through which the control shaft 1321 extends. In one exemplary embodiment, connector 1300 can have one ramped exterior surface 1319 formed at a distal end of control shaft 1321, and one ramped exterior surface 1319 formed on a free standing bushing 1317 through which the control shaft 1321 extends. The exterior ramped surface formed on the control shaft 1321 can be received in a central opening of first arm 1306A. The free standing bushing 1317 with exterior ramped surface 1319 can be received in a central opening of second arm 1306B. Exterior ramped surfaces 1319 can be in contact with an exterior ramped surface 1314 of actuation rod 1312, such that exterior ramped surface 1314 can slidably translate along exterior ramped surface 1319.

A distal end of control shaft 1321 can be seated in the central opening 1307 of first arm 1306A and extend along central axis A10, passing through bushing 1317 of the second arm 1306B, such that a proximal end of the control shaft is received in the handle cavity 1303. The proximal end of control shaft 1321 can preferably have external threads configured to threadably engage with internal threads of an inner handle component 1309. As will be described below, this configuration can facilitate translation of the control shaft along axis A10.

A proximal face of bushing 1317 can contact a distal end of a compression member 1320. Compression member 1320 can be a U-shaped body axially received within handle 1302. The compression member 1320 can retain a compression spring 1322. The compression spring coaxially surrounds a distal portion of inner handle component 1309. A proximal face of compression spring 1322 can abut a distal face of a flange formed on inner component 1309. Compression member 1320 and compression spring 1322 can exert a spring force on bushing 1317 in a distal direction such that when bushing 1317 reaches a proximal position, the compression member 1320 and compression spring 1322 act to urge the bushing 1317 distally along axis. The distal motion of bushing 1317 can cause actuation shaft 1312 of second arm 1306B to move radially outward from axis A10 and translate distally along longitudinal axis A11 of arm 1306B.

An exemplary method of operating connector 1300 is described herein. Rotation of handle 1302 in a first direction can draw the control shaft 1321 proximally into handle cavity 1303 along axis A10. Proximal movement of the control shaft 1321 can be bounded by proximal handle component 1310. Exterior ramped surface 1319 formed on control shaft 1321 is drawn proximally with the movement of the control shaft. The ramped exterior surface 1314 at proximal end of actuation shaft 1312 slides along the exterior ramped surface 1319, causing the actuation shaft 1312 to move radially outward from central axis A10 along inner passage 1316. As the control shaft 1321 and integrally formed exterior ramped surface 1319 move in an upwards direction, the free standing bushing 1317 abuts compression member 1320. Bushing 1317 is urged distally by compression member 1320, which can cause the ramped exterior surface 1314 of actuation shaft 1312 to slide along exterior ramped surface 1319 and translate the actuation shaft 1312 radially outward from central axis A10 along the interior passage 1316 of arm 1306B. As actuation shaft 1312 of each arm 1306A, 1306B translates distally within their respective inner passage 1316, the actuation shaft 1312 urges respective attachment features 1308A, 1308B into a locked state. As will be described in detail below, the locked state of attachment features 1308A, 1308B restricts relative motion between the attachment feature 1308A, 1308B and an object received in a receiving recess 1334, 1354 of the respective attachment features 1308A, 1308B. Rotating the handle 1302 in the first direction can lock relative motion between first arm 1306A and second arm 1306B. As the control shaft 1321 is drawn proximally along A10, the first tubular portions of arms 1306A, 1306B compress such that their respective bearing surfaces 1311 engage to lock the relative position of arms 1306A, 1306B.

FIG. 13K and FIG. 13L illustrate a side-loading jaw attachment feature 1308A. The attachment feature 1308A can include a receiving recess 1334 formed by a sleeve 1330 and a movable jaw 1332. Sleeve 1330 can have an axial opening 1344 for receiving a member to which side-loading jaw attachment feature 1308A can be secured. In one embodiment shown in FIG. 13C, axial opening 1344 may be configured to receive a distal end of an arm 1306 of connector 1300. A cutout 1345 for receiving a pin 1346 may be formed at opposite sides of the axial opening 1344. As can be seen in FIG. 13C, pin 1346 may be placed in circular groove 1325 at the distal end of the arm 1306. The connection of the sleeve 1330 to the arm 1306 by way of the pin 1346 being seated in the cutout 1345 and circular groove 1325, respectively, allows for rotation of the sleeve relative to the arm to achieve a desired positioning prior to securing the movable jaw 1332 to the arm 1306. The movable jaw 1332 can be seated at a distal end of axial opening 1344 such that the movable jaw can be engaged with the distal end of actuation shaft 1312 and translate in tandem with the actuation shaft 1312 along axial opening 1344.

Movable jaw 1332 can have an axial opening 1336 through which a fastener 1338 can be inserted to engage with a threaded recess 1340 in the distal end of actuation shaft 1312. The sleeve 1330 can have an axial opening 1342 that can align with axial opening 1336 of the movable jaw. The fastener 1338 can have a recess 1339 to facilitate engagement with a driver instrument. Fastener 1338 can be axially inserted through the opening of the sleeve 1342 and the opening of the movable jaw 1336 into the threaded recess 1340. FIG. 13C illustrates the fastener 1338 engaged within recess 1340. As the actuation shaft translates in a distal direction, the movable jaw can translate distally to reduce the size of receiving recess 1334 and secure an object held therein. Conversely, as the actuation shaft translates in a proximal direction, the movable jaw can translate proximally to increase the size of receiving recess 1334 and release an object held therein.

FIGS. 13M-13N illustrate a ball and socket clamp attachment feature 1308B. Ball and socket clamp 1308B can be formed from a sleeve 1350 having a proximal and distal end 1350*p*, 1350*d* and a movable jaw 1352. The movable jaw 1352 is configured to move distally along a longitudinal axis of the sleeve 1350 to lock an object received within receiving recess 1354 of the clamp 1308B. As shown in FIG. 13M, sleeve 1350 can have two distally extending spaced apart arms 1351, 1352. An opening to the receiving recess 1354 can be formed between opposing inner surfaces of the arms 1351, 1352. The inner surface of each arm 1351, 1352 can have a straight proximal portion and an arcuate distal portion. The inner surface of each arm 1351, 1352 can be identically shaped to mirror one another. The opening to receiving recess can be defined by the inner surface of each arm 1351, 1352 such that a proximal portion of the opening is substantially rectangular in shape and a distal portion of the opening is substantially circular in shape. A distal end of arms 1351, 1352 can have a laterally extending projection such that a distance between the distal end of arms 1351, 1352 is smaller than a distance between the arcuate portions of arms 1351, 1352.

The ball and socket clamp 1308B can attach to a distal end of an arm 1306 and an actuation shaft 1312. Sleeve 1350, having an axial recess 1364 with cutouts 1365, can attach to a distal end of an arm 1306 in the same manner as described above with respect to attachment 1308A. After the arm 1306 is inserted into the sleeve 1350, a movable jaw 1352 having an axial opening 1356 and a fastener 1358, can be threadably engaged with a threaded recess 1340 in the distal end of actuation shaft 1312.

In operation, an object can be inserted into receiving recess 1354 via the opening between spaced apart arms 1351, 1352 with the movable jaw 1352 in a proximal position, e.g., an attached actuation shaft 1312 is in a proximal position within an arm 1306. With the object received in receiving recess 1354, the movable jaw 1352 can translate distally in association with the actuation shaft 1312 to urge the object within the receiving recess 1354 to a distal end of sleeve 1350. As the object moves distally, the object can abut the lateral projections of arms 1351, 1352. An axial force from the movable jaw 1352 can lock the object against the lateral projections and within the receiving recess 1354. The object can be released from the clamp 1308B as the movable jaw 1352, in association with the actuation shaft 1312, translates proximally along the longitudinal axis away from the distal end of sleeve 1350, thereby removing the distally exerted force on the object.

Figure 14A:
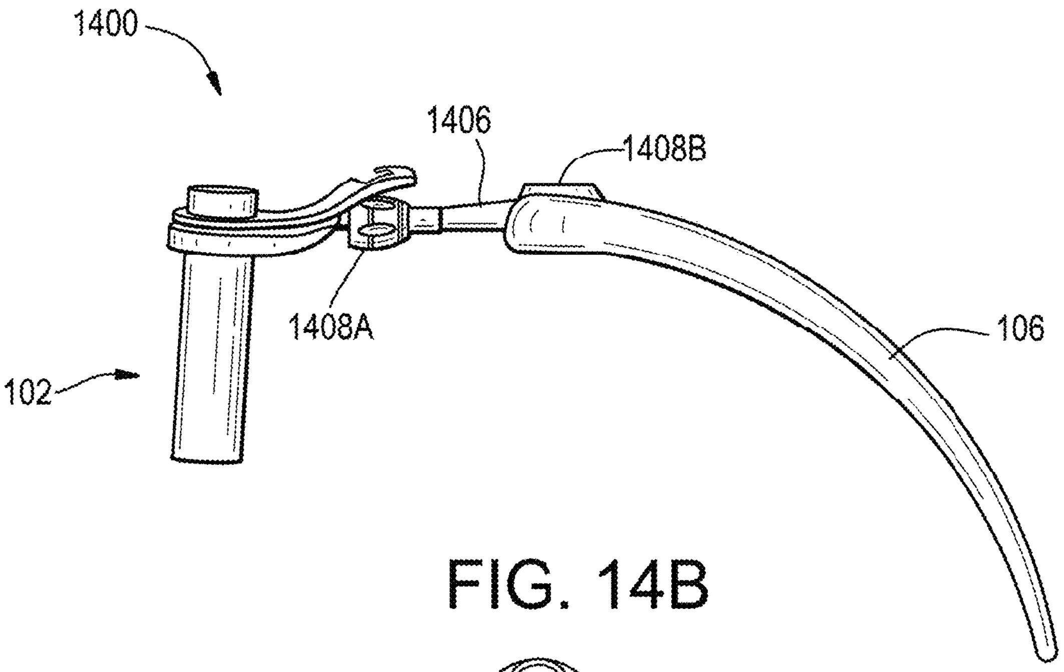
FIG. 14A is a schematic perspective view of another embodiment of a connector in use to support an access device.
Figure 14B:
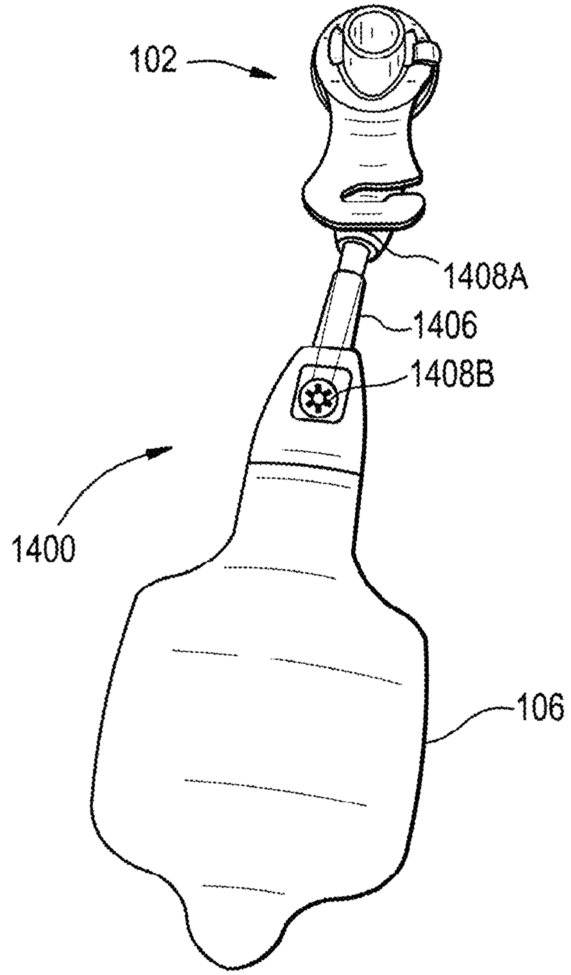
FIG. 14B is another schematic perspective view of the connector in use to support an access device of FIG. 14A.

In an alternative embodiment, as shown in FIG. 14, a connector system 1400 can comprise a single arm 1406. Arm 1406 can be constructed similar to the arms disclosed herein, the arm having an attachment feature 1408A at a distal end configured to engage with a first object. In a preferred embodiment, attachment feature 1408A can engage with a surgical access device 102. The surgical access device attachment feature 1408A may, by way of non-limiting example, be a ball joint attachment. Attachment feature 1408A may be any of the disclosed attachment features or engagement features disclosed herein. A proximal end of arm 1406 can include a second attachment feature 1408B configured to engage with a second object. In a preferred embodiment, attachment feature 1408B can engage with a support 106. The support 106 can be an adhesive patch configured to be attached to a patient. Arm 1406 can be made from a conformable material such that arm 1406 can be manipulated to achieve a desired orientation of the first object and the second object, secured within the first attachment feature 1408A and the second attachment feature 1408B, respectively.

It will be appreciated that the various connectors and the various connector elements disclosed herein can be used with any of the attachment features or engagement features disclosed herein to connect a first object to a second object.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A surgical instrument, comprising:

a first rigid arm having a first tubular portion that extends from a proximal end to a distal end along a longitudinal axis of the first rigid arm, the proximal end of the first tubular portion having a first ring shaped bearing surface that defines a first central opening;

a first attachment feature disposed on the distal end of the first rigid arm, the first attachment feature being configured to engage a first object;

a second rigid arm having a second tubular portion that extends from a proximal end to a distal end along a longitudinal axis of the second rigid arm, the proximal end of the second tubular portion having a second ring shaped bearing surface that defines a second central opening;

a second attachment feature disposed on the distal end of the second rigid arm, the second attachment feature being configured to engage a second object; and an actuation assembly that extends through the first central opening and the second central opening along a central longitudinal axis of the first and second central openings, the actuation assembly being configured to rotate in a first direction to lock the first and second objects at the distal end of each the first and second rigid arm and to rotate in a second direction to release the first and second objects at the distal end of each the first and second rigid arm.

2. The instrument of claim 1, wherein at least one of the first tubular portion or the second tubular portion defines an inner passage in communication with the first central opening or the second central opening and has an actuation shaft disposed therein, the actuation shaft being configured to translate along the longitudinal axis of the first rigid arm or the second rigid arm in which the at least one of the first tubular portion or the second tubular portion is defined.

3. The instrument of claim 2, wherein the actuation assembly comprises a handle, a bushing, and a shaft, the shaft being configured to be extend through the bushing and the first and second ring shaped bearing surfaces to be received in the handle such that the shaft rotates with rotation of the handle.

4. The instrument of claim 3, wherein the first central opening and the second central opening is complementary to a geometry of the bushing.

5. The instrument of claim 4, wherein a translation of the bushing along the central longitudinal axis of the first and second central openings moves the shaft along the central longitudinal axis of the first rigid arm or the central longitudinal axis of the second rigid arm.

6. The instrument of claim 3, wherein the shaft is configured to move towards the handle along the central longitudinal axis of the first and second central openings to lock the relative positions of the first rigid arm and the second rigid arm in response to the rotation of the handle in the first direction.

7. The instrument of claim 2, wherein the first attachment feature engages the first object via a side-loading jaw feature and the second attachment feature engages the second object via a ball and socket clamp feature.

8. The instrument of claim 7, wherein the first attachment feature further comprises a receiving recess formed by a sleeve and a movable jaw to engage the first object, the sleeve being configured to rotate relative to the first rigid arm to achieve a desired position of the sleeve to the first rigid arm prior to securing the movable jaw to the first rigid arm.

9. The instrument of claim 8, wherein the sleeve further comprises an axial opening to receive the first rigid arm therein, the movable jaw being configured to be seated at a distal end of the axial opening such that the movable jaw is engaged with the distal end of the actuation shaft and translates in tandem with the actuation shaft along the axial opening to engage the first object.

10. The instrument of claim 9, wherein the actuation shaft is configured to translate distally along the longitudinal axis of the first rigid arm to translate the movable jaw distally to reduce a size of the receiving recess to lock the first object when the actuation assembly is rotated in the first direction and is configured to translate proximally along the longitudinal axis of the first rigid arm to translate the movable jaw proximally to increase a size of the receiving recess to release the first object when the actuation assembly is rotated in the second direction.

11. The instrument of claim 7, wherein the second attachment feature further comprises a sleeve defined by a pair of distally extending spaced apart arms and a movable jaw to engage the second object, the movable jaw being configured to moved distally along an axis of the sleeve to lock the second object within the receiving recess.

12. The instrument of claim 11, wherein the actuation shaft is configured to translate distally along the longitudinal axis of the second rigid arm to translate the movable jaw distally to urge the second object within the receiving recess to a distal end of the sleeve to abut one or more of the lateral projection s of the arms to lock the second object within the receiving recess when the actuation assembly is rotated in the first direction and is configured to translate proximally along the longitudinal axis of the second rigid arm to translate the movable jaw proximally to reduce a distally exerted force onto the second object when the actuation assembly is rotated in the second direction.

13. The instrument of claim 1, wherein the first and second rigid arms are configured to rotate relative to one another.

14. The instrument of claim 13, wherein the first and second rigid arms are configured to be disposed at an angle in a range of about 0 degrees to about 180 degrees relative to one another.

15. The instrument of claim 1, wherein the first ring shaped bearing surface and the second ring shaped bearing surface are configured to be rotatable about a central axis of the actuation assembly.

16. The instrument of claim 1, wherein the first and second ring shaped bearing surface comprise a plurality of teeth configured to selectively interlock to maintain the first arm and the second arm in one of a plurality of discrete rotational positions relative to one another.

17. The instrument of claim 1, wherein the first object is one or more of a support, a pedicle post, a pedicle screw, a monoaxial screw head, an elongation of a monoaxial or polyaxial screw head, a bone anchor screw extension tab, a skin of a patient, or an operating table, and the second object is a surgical access device.

18. The instrument of claim 1, further comprising a ring disposed between the first tubular portion and the second tubular portion.

19. The instrument of claim 1, wherein the actuation assembly is configured to simultaneously lock the first and second objects at the distal ends of each the first and second rigid arm.

20. The instrument of claim 1, wherein at least one of the first attachment feature or the second attachment feature further comprises a flange and a groove configured to engage the first or the second object.

* * * * *